(12) United States Patent
Fujiwara

(10) Patent No.: US 10,054,853 B2
(45) Date of Patent: *Aug. 21, 2018

(54) MONOMER, POLYMER, RESIST COMPOSITION, AND PATTERNING PROCESS

(71) Applicant: Shin-Etsu Chemical Co., Ltd., Tokyo (JP)

(72) Inventor: Takayuki Fujiwara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,210

(22) Filed: Apr. 10, 2017

(65) Prior Publication Data

US 2017/0299963 A1   Oct. 19, 2017

(30) Foreign Application Priority Data

Apr. 14, 2016 (JP) ................. 2016-080899

(51) Int. Cl.
*G03F 7/004* (2006.01)
*G03F 7/039* (2006.01)
(Continued)

(52) U.S. Cl.
CPC .......... *G03F 7/0392* (2013.01); *C07C 307/02* (2013.01); *C07C 311/49* (2013.01);
(Continued)

(58) Field of Classification Search
CPC ...... G03F 7/004; G03F 7/0045; G03F 7/0046; G03F 7/0382; G03F 7/0392; G03F 7/11;
(Continued)

(56) References Cited

U.S. PATENT DOCUMENTS 7,511,169 B2   3/2009   Ohsawa et al.
7,875,746 B2   1/2011   Wada
(Continued)

FOREIGN PATENT DOCUMENTS

EP   0 473 547 A1   3/1992
EP   1 635 218 A2   3/2006
(Continued)

OTHER PUBLICATIONS

Machine translation of JP 2014-167579 (no date).*
(Continued)

*Primary Examiner* — Amanda C Walke
(74) *Attorney, Agent, or Firm* — Westerman, Hattori, Daniels & Adrian, LLP

(57) ABSTRACT

A monomer having an onium salt structure represented by formula (1) gives a polymer which is fully compatible with resist components. A resist composition comprising the polymer has advantages including reduced acid diffusion, high sensitivity, high resolution, a good balance of lithography properties, and less defects, and is quite effective for precise micropatterning.

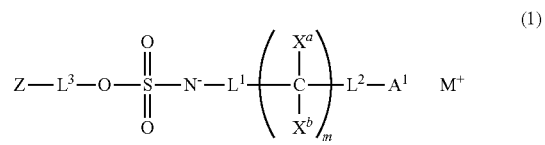

(1)

21 Claims, 1 Drawing Sheet

(51) Int. Cl.

| | |
|---|---|
| *C07C 381/12* | (2006.01) |
| *C07C 311/49* | (2006.01) |
| *C07D 307/00* | (2006.01) |
| *C07C 307/02* | (2006.01) |
| *C08F 220/18* | (2006.01) |
| *G03F 7/038* | (2006.01) |
| *G03F 7/16* | (2006.01) |
| *G03F 7/20* | (2006.01) |
| *G03F 7/38* | (2006.01) |
| *G03F 7/32* | (2006.01) |
| *G03F 7/11* | (2006.01) |
| *C08F 220/20* | (2006.01) |
| *C08F 220/38* | (2006.01) |

(52) U.S. Cl.
CPC .......... *C07C 381/12* (2013.01); *C07D 307/00* (2013.01); *C08F 220/18* (2013.01); *G03F 7/0045* (2013.01); *G03F 7/0046* (2013.01); *G03F 7/0382* (2013.01); *G03F 7/11* (2013.01); *G03F 7/162* (2013.01); *G03F 7/168* (2013.01); *G03F 7/2006* (2013.01); *G03F 7/2041* (2013.01); *G03F 7/322* (2013.01); *G03F 7/325* (2013.01); *G03F 7/38* (2013.01); *C07C 2603/74* (2017.05); *C08F 220/20* (2013.01); *C08F 2220/1866* (2013.01); *C08F 2220/387* (2013.01)

(58) Field of Classification Search
CPC ........ G03F 7/162; G03F 7/168; G03F 7/2006; G03F 7/2041; G03F 7/322; G03F 7/325; G03F 7/38; H01L 21/0274; C07C 311/49; C07C 381/12; C08F 220/18
USPC .... 430/270.1, 394, 311, 322, 325, 329, 330; 564/80
See application file for complete search history.

(56) References Cited

U.S. PATENT DOCUMENTS

| | | | |
|---|---|---|---|
| 7,919,226 B2 | 4/2011 | Ohsawa et al. | |
| 8,034,547 B2 | 10/2011 | Tsubaki et al. | |
| 8,057,985 B2 | 11/2011 | Ohashi et al. | |
| 8,105,748 B2 | 1/2012 | Ohashi et al. | |
| 8,227,183 B2 | 7/2012 | Tsubaki et al. | |
| 8,241,840 B2 | 8/2012 | Tsubaki et al. | |
| 9,709,892 B2 * | 7/2017 | Kataoka ................ C08F 220/28 |
| 9,777,093 B2 * | 10/2017 | Hatakeyama ......... C08F 220/38 |
| 2015/0093709 A1 | 4/2015 | LaBeaume | |
| 2016/0070167 A1 * | 3/2016 | Kataoka .................. G03F 7/038 428/195.1 |
| 2016/0320698 A1 * | 11/2016 | Fujiwara .................. G03F 7/30 |
| 2016/0349612 A1 * | 12/2016 | Fujiwara ............... C08F 220/38 |

FOREIGN PATENT DOCUMENTS

| | | | | |
|---|---|---|---|---|
| EP | 1 635 218 A3 | 3/2007 | | |
| JP | 4-230645 A | 8/1992 | | |
| JP | 2003064259 A * | 3/2003 | .......... H01G 9/2009 |
| JP | 2005-84365 A | 3/2005 | | |
| JP | 2006-84530 A | 3/2006 | | |
| JP | 2006-84660 A | 3/2006 | | |
| JP | 2006-330098 A | 12/2006 | | |
| JP | 2007-145797 A | 6/2007 | | |
| JP | 2008-281974 A | 11/2008 | | |
| JP | 2008-281975 A | 11/2008 | | |
| JP | 2010-8912 A | 1/2010 | | |
| JP | 2010-77404 A | 4/2010 | | |
| JP | 2010-116550 A | 5/2010 | | |
| JP | 4554665 B2 | 9/2010 | | |
| JP | 2012073398 A * | 4/2012 | | |
| JP | 2014-152122 A | 8/2014 | | |
| JP | 2014167579 A * | 9/2014 | .......... G03F 7/0045 |
| KR | 10-2015-0035455 A | 4/2015 | | |
| WO | WO 2014132934 A1 * | 9/2014 | .......... G03F 7/0045 |

OTHER PUBLICATIONS

Machine translation of JP 2012-073398 (no date).*

Tsuda et al., "Journal of Photopolymer Science and Technology", The Technical Association of Photopolymers, 2004, vol. 17, No. 4, pp. 587-601. (18 pages).

Office Action dated Mar. 22, 2018, issued in counterpart Korean Application No. 10-2017-0047213, with English translation (25 pages).

* cited by examiner

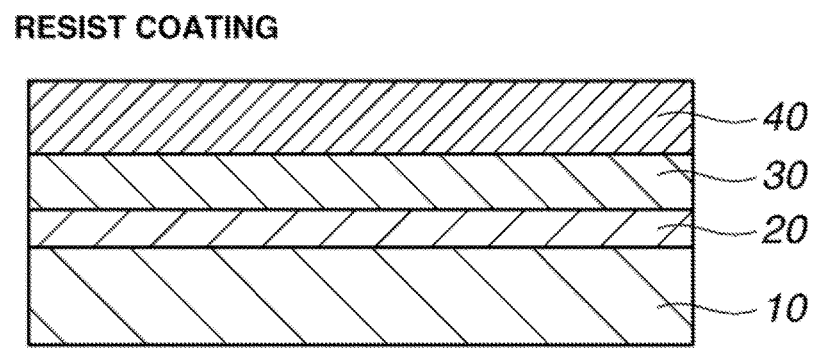
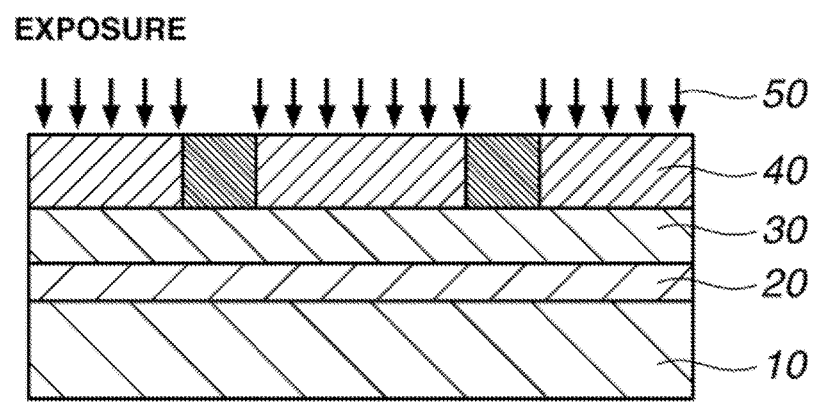
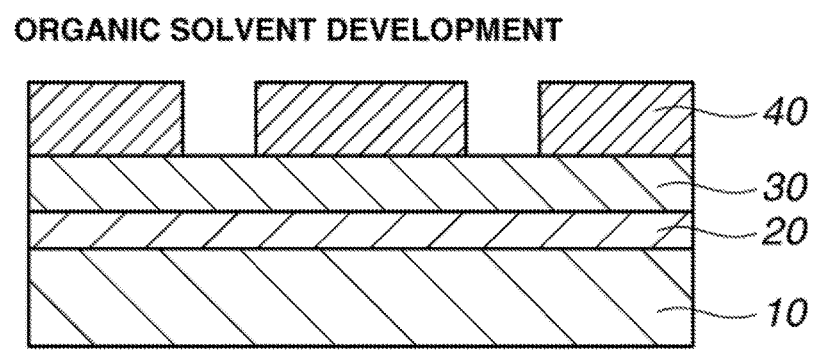

MONOMER, POLYMER, RESIST COMPOSITION, AND PATTERNING PROCESS

CROSS-REFERENCE TO RELATED APPLICATION

This non-provisional application claims priority under 35 U.S.C. § 119(a) on Patent Application No. 2016-080899 filed in Japan on Apr. 14, 2016, the entire contents of which are hereby incorporated by reference.

TECHNICAL FIELD

This invention relates to an onium salt monomer, a polymer thereof, a resist composition comprising the polymer, and a pattern forming process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using an ArF excimer laser as the light source is requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkaline development and organic solvent development is under study. As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 refers to the prior art PAGs capable of generating α,α-difluoroalkanesulfonic acid, such as di(4-t-butylphenyl)-iodonium 1,1-difluoro-2-(1-naphthyl)ethanesulfonate and PAGs capable of generating α,α,β,β-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

It was attempted to suppress acid diffusion by incorporating a bulky substituent or polar group into PAG. Patent Document 4 describes a PAG having 2-acyloxy-1,1,3,3,3-pentafluoropropane-1-sulfonic acid which is fully soluble and stable in resist solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of MEF, pattern profile and sensitivity.

Studies were also made to suppress acid diffusion by incorporating recurring units having a PAG function in a base resin. For instance, Patent Document 5 discloses a polymer obtained from polymerization of an acryloyloxyphenyldiphenylsulfonium salt. Patent Document 6 proposes to incorporate the acryloyloxyphenyldiphenylsulfonium salt into a polyhydroxystyrene resin for improving the LWR of this base resin. However, since the sulfonium salt is bound at its cation side to the polymer, the sulfonic acid generated therefrom upon exposure to high-energy radiation is equivalent to the sulfonic acids generated by conventional PAGs. These proposals are thus unsatisfactory to suppress acid diffusion. On the other hand, Patent Documents 7 and 8 disclose a resist composition comprising a polymer of fluorinated backbone obtained from polymerization of a sulfonium salt. Some improvements in LWR are achieved. However, when further miniaturization, specifically the formation of finer size patterns complying with 32-nm and finer node devices of the next generation is taken into account, the lithography properties including LWR are still unsatisfactory.

As resist patterns with high resolution are currently required, not only lithography characteristics including pattern profile, contrast, MEEF and roughness are necessary, but improvements in (surface) defects of resist patterns as developed become more requisite. The surface defects refer to all faults which are detected when the resist pattern as developed is observed from just above by a surface flaw detector (trade name KLA by KLA-Tencoor Co., Ltd.). Such faults include scum, foam, debris, and bridges between resist pattern features after development. These defects form because PAG or other resist components have low solubility in casting solvent and leave undissolved residues after developer immersion.

As the PAG which has a high compatibility and causes least defects, there are known compounds containing an anion having an acid generating site of imide acid (imidic acid) or methide acid structure. Patent Documents 9 to 12 describe PAGs of imide or methide acid type. However, the PAGs described therein allow for noticeable acid diffusion. Their lithography performance is unsatisfactory to the current requirement to form resist patterns at high resolution.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP-A 2007-145797
Patent Document 5: JP-A H04-230645
Patent Document 6: JP-A 2005-084365
Patent Document 7: JP-A 2010-116550
Patent Document 8: JP-A 2010-077404
Patent Document 9: JP-A 2010-008912
Patent Document 10: JP-A 2006-084660
Patent Document 11: JP-A 2006-084530
Patent Document 12: JP-A 2006-330098 (U.S. Pat. No. 7,875,746)
Non-Patent Document 1: Journal of Photopolymer Science and Technology, Vol. 17, No. 4, p 587 (2004)

DISCLOSURE OF THE INVENTION

The photoacid generator (PAG) produces an acid which must satisfy many requirements including a sufficient acid strength to cleave acid labile groups in a resist material, high sensitivity, stability in the resist material during shelf storage, adequately controlled acid diffusion, low volatility, minimal foreign matter left after development and resist removal, and good degradability in that it is decomposed away after the expiration of its role in lithography without imposing a load to the environment. In the case of ArF immersion lithography, minimal dissolution in water is also desirable. Prior art PAGs fail to satisfy some of these requirements.

An object of the invention is to provide a resist composition capable of forming a chemically amplified resist film which when processed by photolithography using high-energy radiation such as ArF excimer laser, EB or EUV as the light source, offers reduced acid diffusion, high resolution, high sensitivity, a good balance of lithography properties including MEF, LWR, and CDU, and is improved in compatibility and reduced in defect formation; a polymer suited as a base resin in the resist composition; a monomer suited as a starting material for the polymer; and a patterning process using the resist composition.

The inventors have found that the above and other objects are attained by a resist composition comprising a polymer of specific structure as a base resin. This resist composition has the advantages of reduced acid diffusion, high sensitivity and resolution, a good balance of lithography properties, compatibility, and a minimal number of defects, and is quite effective for precise micropatterning.

In one aspect, the invention provides a monomer having the formula (1).

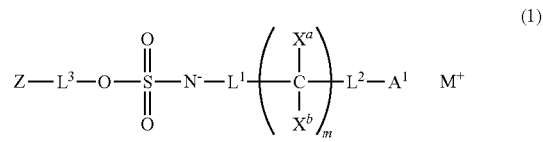

Herein Z is a polymerizable group, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond, $L^3$ is a single bond or a $C_1$-$C_{40}$ straight, branched or cyclic divalent hydrocarbon group which may contain a heteroatom, $A^1$ is hydrogen, halogen or a $C_1$-$C_{20}$ straight, branched or cyclic monovalent hydrocarbon group which may contain a heteroatom, $X^a$ and $X^b$ are each independently hydrogen, fluorine or trifluoromethyl, with the proviso that at least one of $X^a$ and $X^b$ is a substituent group other than hydrogen, m is an integer of 1 to 4, and $M^+$ is an onium cation.

Preferably Z is a group having the formula (2) or (3).

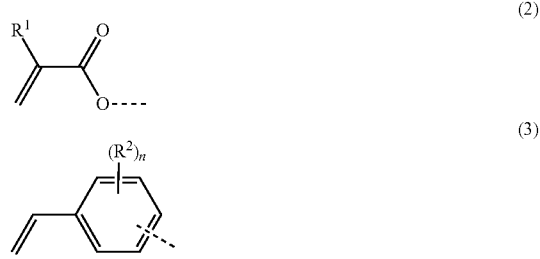

Herein $R^1$ is hydrogen, methyl, fluorine or trifluoromethyl, $R^2$ is a $C_1$-$C_{12}$ straight, branched or cyclic monovalent hydrocarbon group which may contain a heteroatom, where there are present a plurality of $R^2$, they may be the same or different and they may bond together to form a ring with carbon atoms on the benzene ring, n is an integer of 0 to 4, and the broken line designates a valence bond to $L^3$ in formula (1).

Preferably $L^1$ is a sulfonyl bond. Also preferably, $L^2$ is a single bond and $A^1$ is hydrogen, fluorine or trifluoromethyl.

In a second aspect, the invention provides a polymer comprising recurring units derived from the monomer defined above. Specifically, the invention provides a polymer comprising recurring units having the formula (4) or (5).

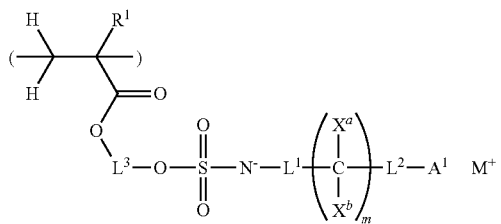

(4)

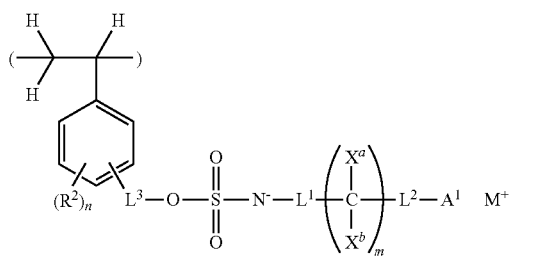

(5)

Herein $R^1$ is hydrogen, methyl, fluorine or trifluoromethyl, $R^2$ is a $C_1$-$C_{12}$ straight, branched or cyclic monovalent hydrocarbon group which may contain a heteroatom, where there are present a plurality of $R^2$, they may be the same or different and they may bond together to form a ring with carbon atoms on the benzene ring, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond, $L^3$ is a single bond or a $C_1$-$C_{40}$ straight, branched or cyclic divalent hydrocarbon group which may contain a heteroatom, $A^1$ is hydrogen, halogen or a $C_1$-$C_{20}$, straight, branched or cyclic monovalent hydrocarbon group which may contain a heteroatom, $X^a$ and $X^b$ are each independently hydrogen, fluorine or trifluoromethyl, with the proviso that at least one of $X^a$ and $X^b$ is fluorine or trifluoromethyl, m is an integer of 1 to 4, n is an integer of 0 to 4, and $M^+$ is an onium cation.

Preferably, $L^1$ is a sulfonyl bond; $L^2$ is a single bond and $A^1$ is hydrogen, fluorine or trifluoromethyl.

In a third aspect, the invention provides a resist composition comprising a base resin containing the polymer defined above and an organic solvent.

Preferably, the polymer further comprises recurring units of at least one type selected from recurring units having the formulae (6) and (7).

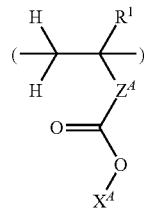

(6)

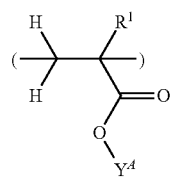

(7)

Herein $R^1$ is as defined above, $Z^A$ is a single bond, phenylene group, naphthylene group or (backbone)-C(=O)-O-$Z'$-, $Z'$ is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

The resist composition may further comprise a photoacid generator other than the compound having the formula (1).

Preferably the photoacid generator has the formula (8) or (9).

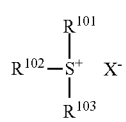

(8)

Herein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, $X^-$ is an anion selected from the formulae (8A) to (8D):

(8A)

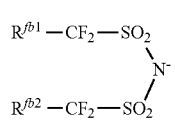

(8B)

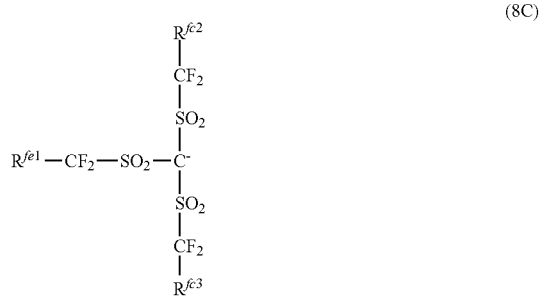

(8C)

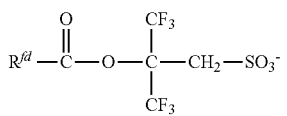

(8D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ straight, branched or cyclic monovalent hydrocarbon group which may contain a heteroatom,

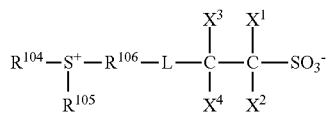

(9)

wherein $R^{104}$ and $R^{105}$ are each independently a $C_1$-$C_{30}$ straight, branched or cyclic monovalent hydrocarbon group which may contain a heteroatom, $R^{106}$ is a $C_1$-$C_{30}$ straight, branched or cyclic divalent hydrocarbon group which may contain a heteroatom, any two of $R^{104}$, $R^{105}$ and $R^{106}$ may bond together to form a ring with the sulfur atom to which they are attached, L is a single bond, ether bond or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl.

The resist composition may further comprise an amine compound.

The resist composition may further comprise a compound having the formula (10) or (11).

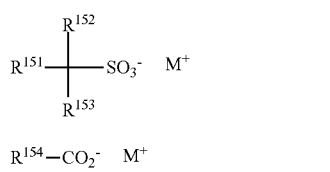

Herein $R^{151}$, $R^{152}$ and $R^{153}$ are each independently hydrogen, halogen exclusive of fluorine, or a $C_1$-$C_{40}$ straight, branched or cyclic monovalent hydrocarbon group which may contain a heteroatom, any two of $R^{151}$, $R^{152}$ and $R^{153}$ may bond together to form a ring with the carbon atom to which they are attached, $R^{154}$ is a $C_1$-$C_{40}$ straight, branched or cyclic monovalent hydrocarbon group which may contain a heteroatom, and $M^+$ is an onium cation.

The resist composition may further comprise a surfactant which is insoluble or substantially insoluble in water and soluble in alkaline developer, and/or a surfactant which is insoluble or substantially insoluble in water and alkaline developer.

In a fourth aspect, the invention provides a pattern forming process comprising the steps of applying the resist composition defined above onto a substrate, prebaking to form a resist film, exposing a selected region of the resist film to KrF excimer laser, ArF excimer laser, EB or EUV, baking, and developing the exposed resist film in a developer.

In one embodiment, the developing step uses an alkaline aqueous solution as the developer, thereby forming a positive pattern in which an exposed region of the resist film is dissolved away and an unexposed region of the resist film is not dissolved.

In another embodiment, the developing step uses an organic solvent as the developer, thereby forming a negative pattern in which an unexposed region of the resist film is dissolved away and an exposed region of the resist film is not dissolved. Preferably the organic solvent is at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens. In this embodiment, the process may further comprise the step of coating a protective film on the resist film prior to the exposure step, wherein immersion lithography is carried out while the liquid is held between the protective film and the projection lens.

Advantageous Effects of Invention

The polymer having an onium salt structure according to the invention is fully compatible with resist components. The resist composition comprising the polymer as base resin has advantages including reduced acid diffusion, high sensitivity, high resolution, and a good balance of lithography properties. When the resist composition is processed by lithography, a pattern with least defects is formed.

BRIEF DESCRIPTION OF THE DRAWINGS

FIGS. 1A, 1B and 1C show in cross-sectional view a patterning process according one embodiment of the invention, FIG. 1A showing a resist film disposed on a substrate, FIG. 1B showing the resist film during exposure, and FIG. 1C showing the resist film during organic solvent development.

DESCRIPTION OF THE PREFERRED EMBODIMENTS

The singular forms "a," "an" and "the" include plural referents unless the context clearly dictates otherwise. The notation (Cn-Cm) means a group containing from n to m carbon atoms per group. In chemical formulae, the broken line denotes a valence bond; Me stands for methyl, Et for ethyl, "Bu for n-butyl, Ac for acetyl, and Ph for phenyl.

The abbreviations have the following meaning.
BB: electron beam
EUV: extreme ultraviolet
PAG: photoaoid generator
PEBs post-exposure bake
MEF: mask error factor
MEEF: mask error enhancement factor
DOF: depth of focus
CDU: critical dimension uniformity
LWR: line width roughness
Monomer The invention provides a monomer having the formula (1).

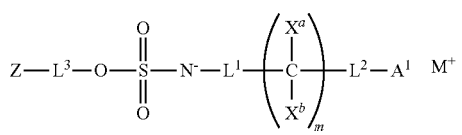

Herein Z is a polymerizable group. The polymerizable group is preferably a group containing a polymerizable carbon-carbon double bond, which is selected from, for example, groups derived from substituted or unsubstituted acrylates such as acrylates (acryloyl group), methaorylates (methacryloyl group), trifluoromethacrylates (trifluoromethacryloyl group), crotonates, maleates, and itaconates, groups derived from cyclic olefins such as norbornene derivatives and tetracyclo[6.2.1.1$^{3,6}$.0$^{2,7}$]dodecene derivatives, and groups derived from multi-substituted styrenes. Of these, groups having the following formula (2) or (3) are preferred for availability of reactants and ease of synthesis.

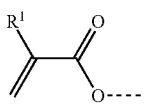

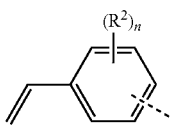

Herein $R^1$ is hydrogen, methyl, fluorine or trifluoromethyl. $R^2$ is a $C_1$-$C_{12}$ straight, branched or cyclic monovalent hydrocarbon group which may contain a heteroatom, n is an integer of 0 to 4. Where there are present a plurality of $R^2$, they may be the same or different and they may bond together to form a ring with carbon atoms on the benzene ring. The broken line designates a valence bond to $L^3$ in formula (1), with the proviso that where $L^3$ is a single bond, the broken line in formula (2) designates a valence bond to S in formula (1).

Examples of the $C_1$-$C_{12}$ straight, branched or cyclic monovalent hydrocarbon group which may contain a heteroatom, represented by $R^2$, include alkyl groups such as methyl, ethyl, propyl, isopropyl, n-butyl, s-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

In formula (1), $L^1$ is a carbonyl bond, sulfonyl bond or sulfinyl bond. Of these, the carbonyl bond (—CO—) and sulfonyl bond (—SO$_2$—) are preferred for ease of synthesis and availability of reactants, with the sulfonyl bond being more preferred in view of the acidity of acid generated after exposure.

In formula (1), $L^2$ is a single bond, ether bond (—O—), carbonyl bond, ester bond (—CO$_2$—), amide bond (—C(=O)NR$_2$—), sulfide bond, sulfinyl bond, sulfonyl bond, sulfonic acid ester bond (—SO$_3$—), sulfinamide bond, sulfonamide bond (—SO$_2$NR$^2$—), carbamate bond or carbonate bond. Of these, the single bond, ether bond, ester bond, amide bond, sulfonic acid ester bond, and sulfonamide bond are preferred, with the single bond, ether bond, ester bond, and amide bond being more preferred.

In formula (1), $L^3$ is a single bond or a $C_1$-$C_{40}$ straight, branched or cyclic divalent hydrocarbon group which may contain a heteroatom. Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

In formula (1), $A^1$ is hydrogen, halogen or a $C_1$-$C_{20}$ straight, branched or cyclic monovalent hydrocarbon group which may contain a heteroatom. Suitable monovalent hydrocarbon groups are as exemplified above for $R^2$.

In formula (1), $X^a$ and $X^b$ are each independently hydrogen, fluorine or trifluoromethyl, with the proviso that at least one of $X^a$ and $X^b$ is a substituent group other than hydrogen, that is, fluorine or trifluoromethyl. Most preferably both $X^a$ and $X^b$ are fluorine.

In formula (1), m is an integer of 1 to 4.

Of the monomers having formula (1), those of the following formulae are preferred.

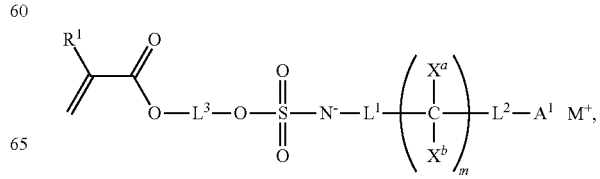

-continued

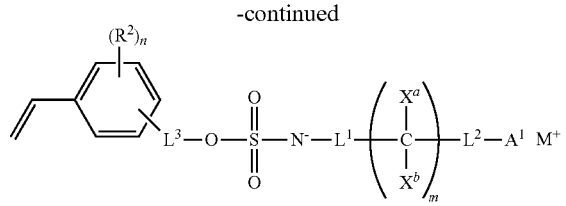

Herein $R^1$, $R^2$, $L^1$, $L^2$, $L^3$, $A^1$, $X^a$, $X^b$, m and n are as defined above, and $M^+$ is described below.

From the standpoint of acidity of generated acid, those of the above formulae wherein $L^1$ is a sulfonyl bond, that is, monomers of the following formulae are preferred.

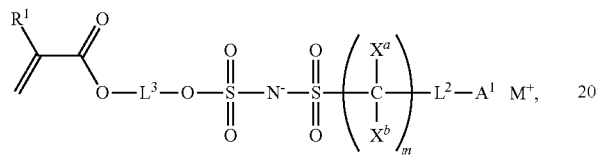

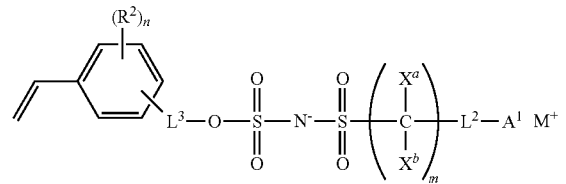

Herein $R^1$, $R^2$, $L^2$, $L^3$, $A^1$, $X^a$, $X^b$, a and n are as defined above, and $M^+$ is described below. It is noted that in the case of m=2 to 4, at least one fluorine atom or trifluoromethyl group should preferably be on α-carbon relative to the sulfonyl bond ($L^1$).

Because of easy and inexpensive synthesis, monomers of the above formulae wherein $L^2$ is a single bond and $A^1$ is hydrogen, fluorine or trifluoromethyl are more preferred. That is, monomers of the following formulae are more preferred.

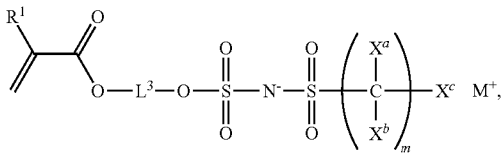

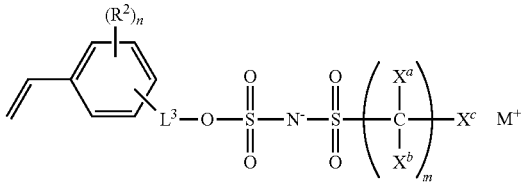

Herein $R^1$, $R^2$, $L^3$, $X^a$, $X^b$, m and n are as defined above, and $M^+$ is described below. $X^c$ is hydrogen, fluorine or trifluoromethyl. At least one of $X^a$, $X^b$ and $X^c$ is a substituent group other than hydrogen. Preferably at least one of $X^a$, $X^b$ and $X^c$ is fluorine. It is noted that in the case of m=2 to 4, at least one fluorine atom or trifluoromethyl group should preferably be on α-carbon relative to the sulfonyl bond ($L^1$). More preferred are those monomers of the above formulae wherein m=1, and $X^a$, $X^b$ and $X^c$ are fluorine, that is, trifluoromethyl is linked to the sulfonyl group ($L^1$).

Examples of the anion moiety of the monomer having formula (1) are shown below, but not limited thereto. Herein $R^1$ is as defined above.

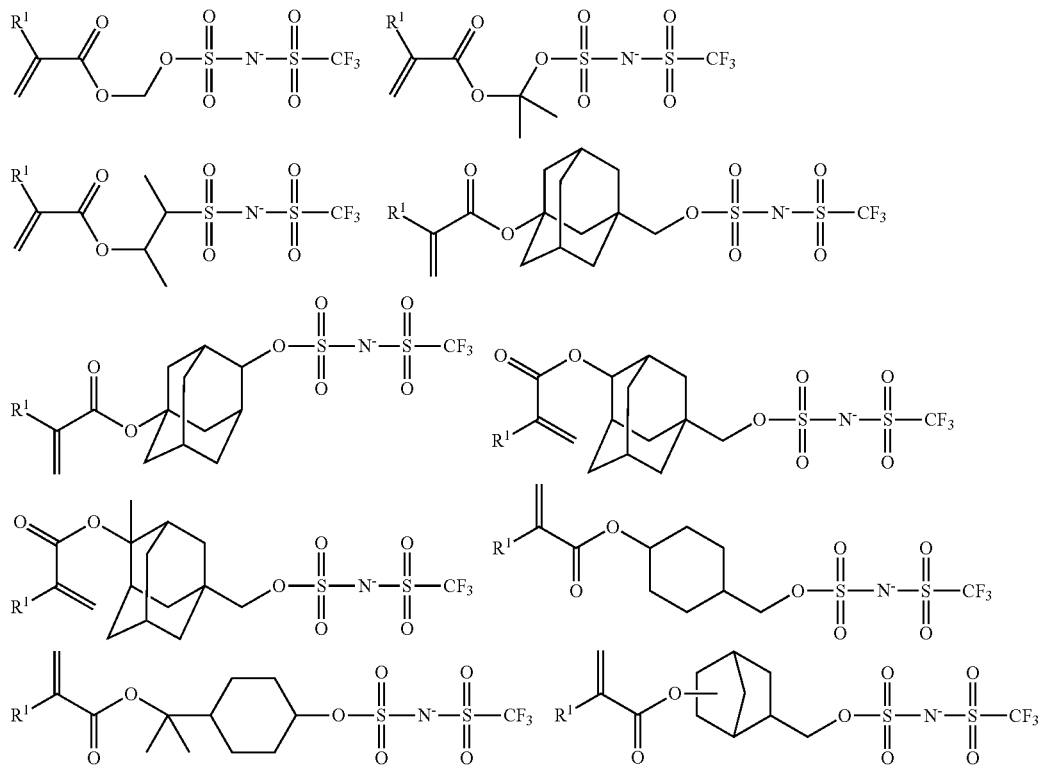

-continued
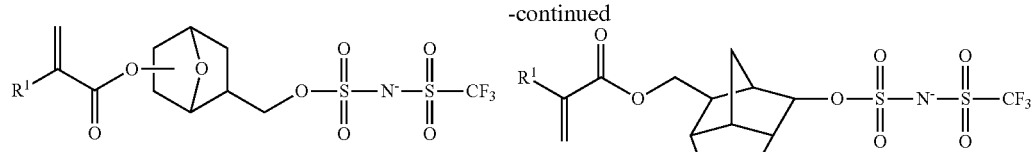
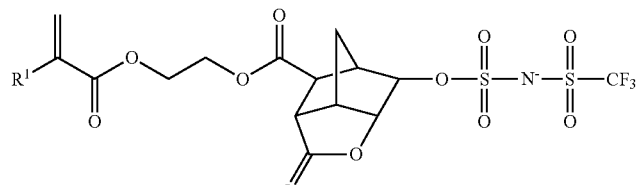
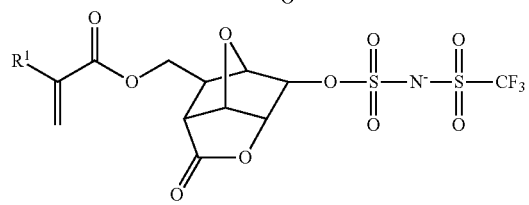
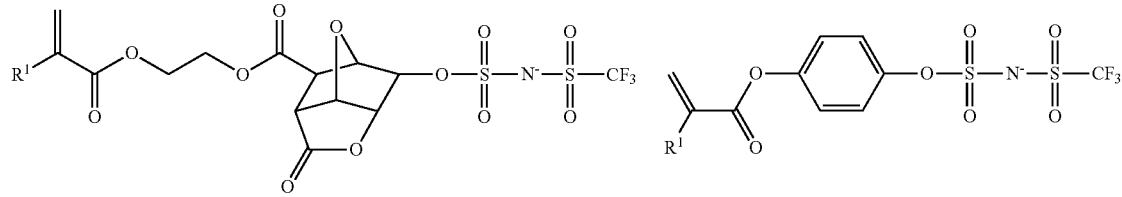
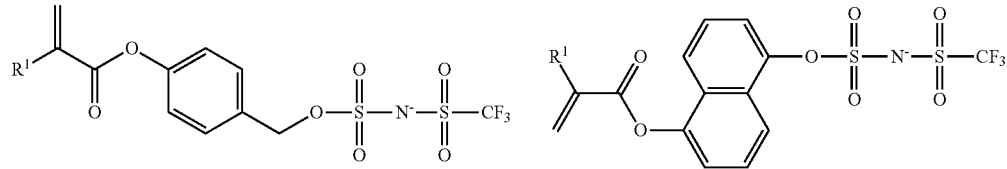
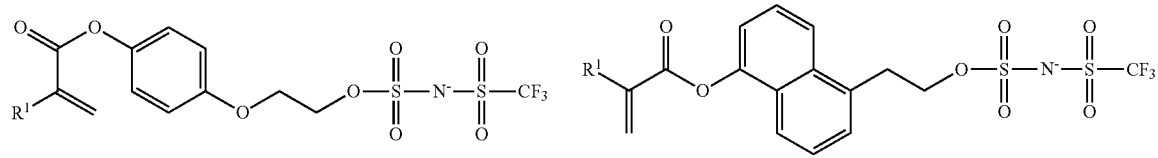
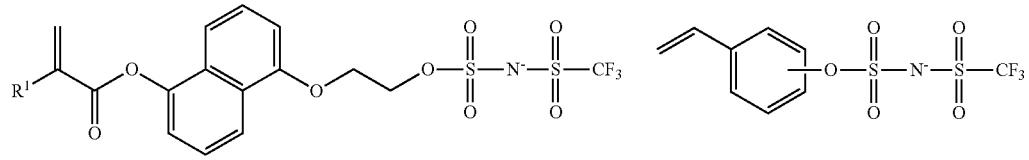
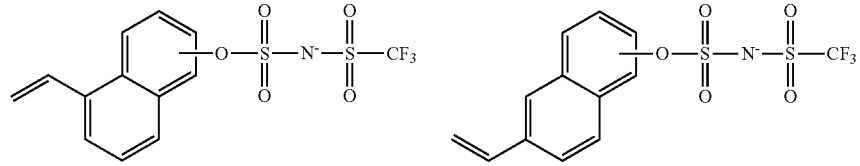
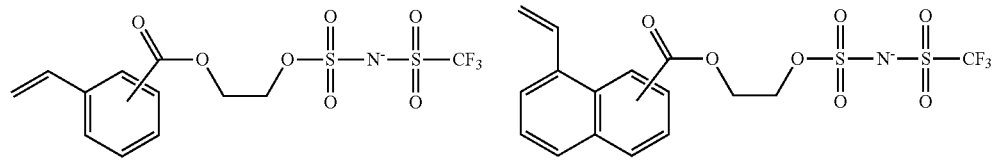
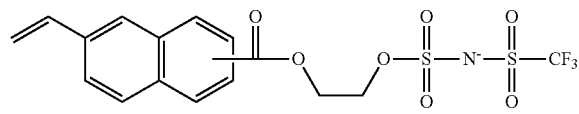

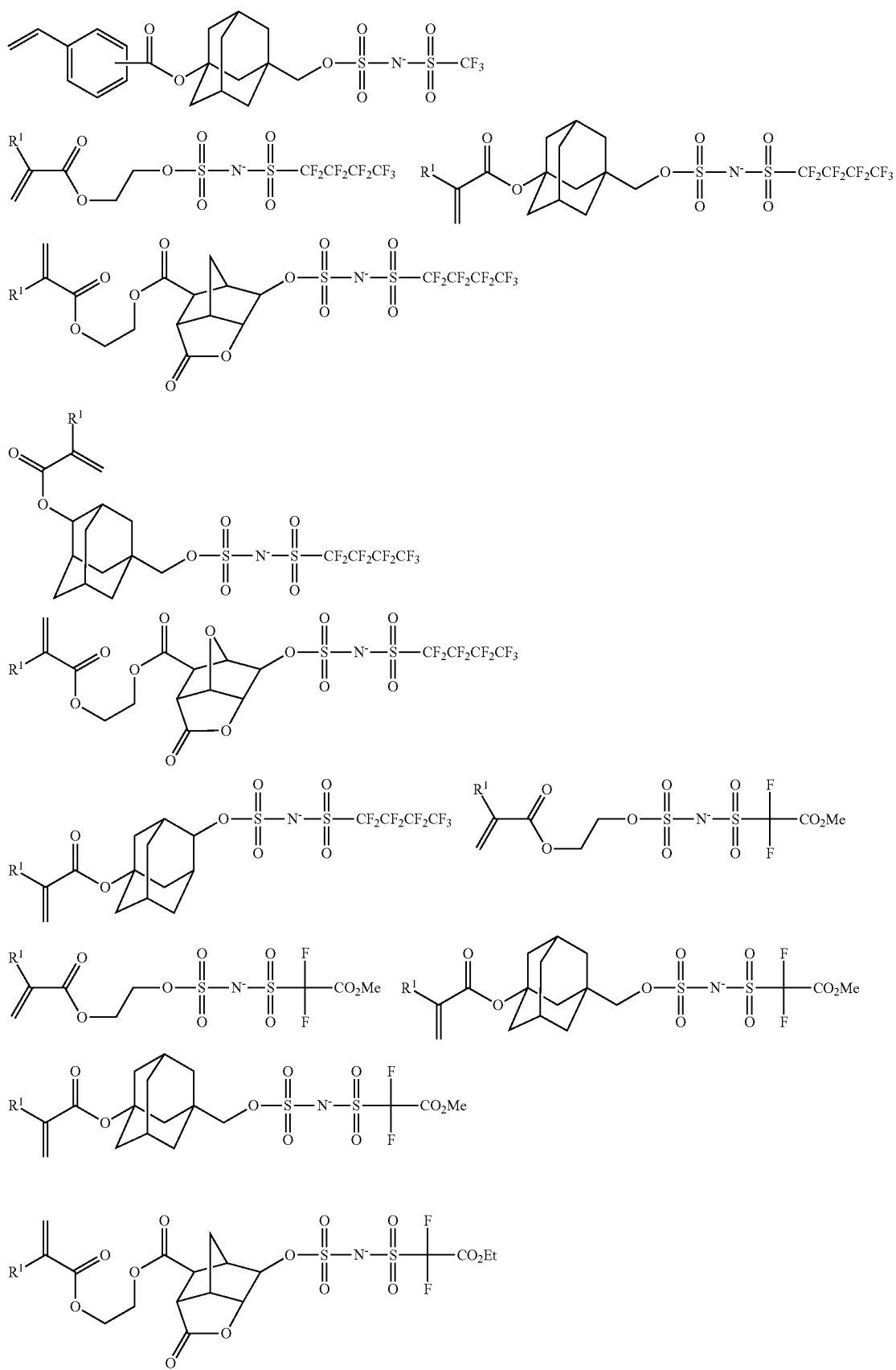

-continued
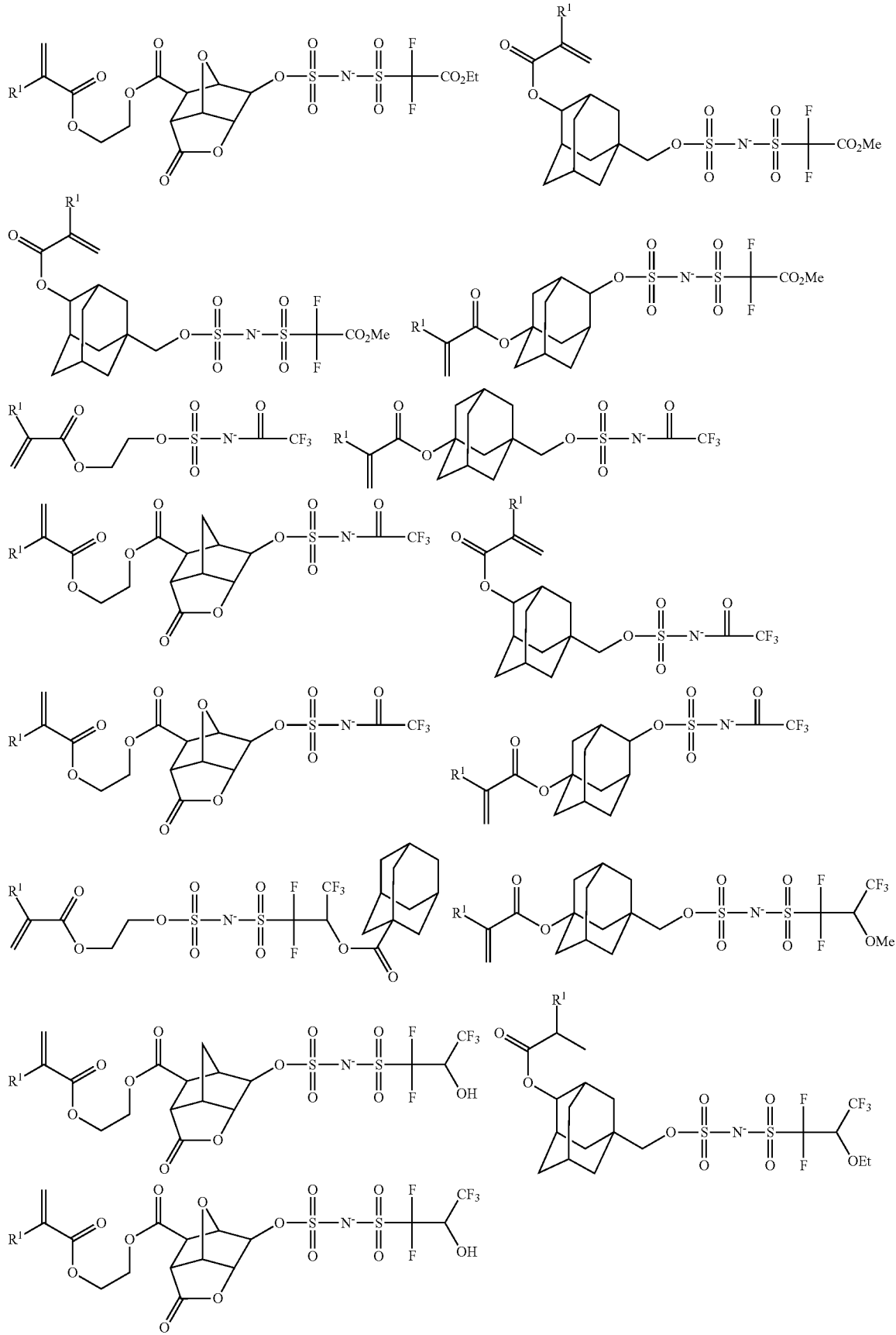

-continued
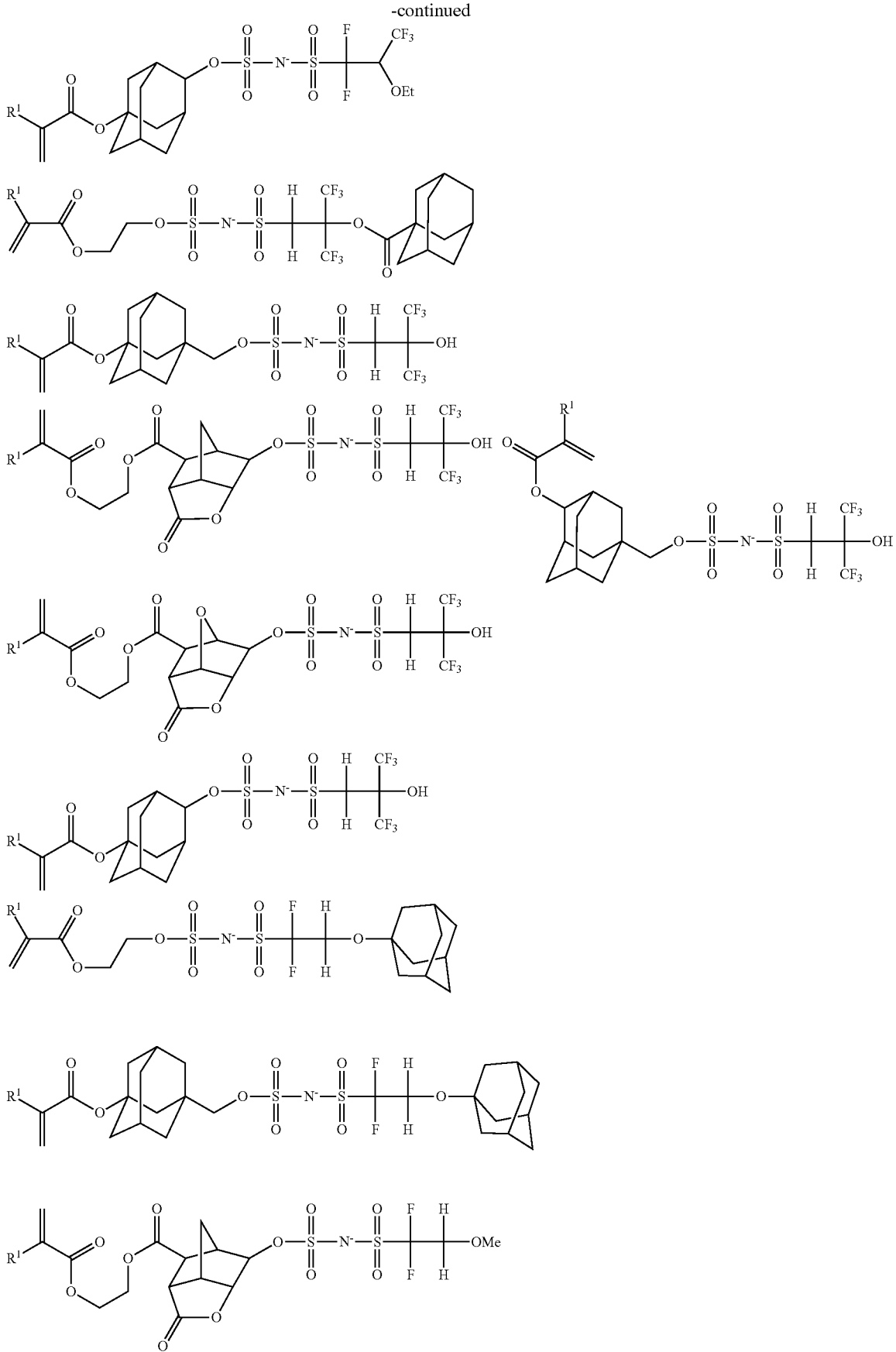

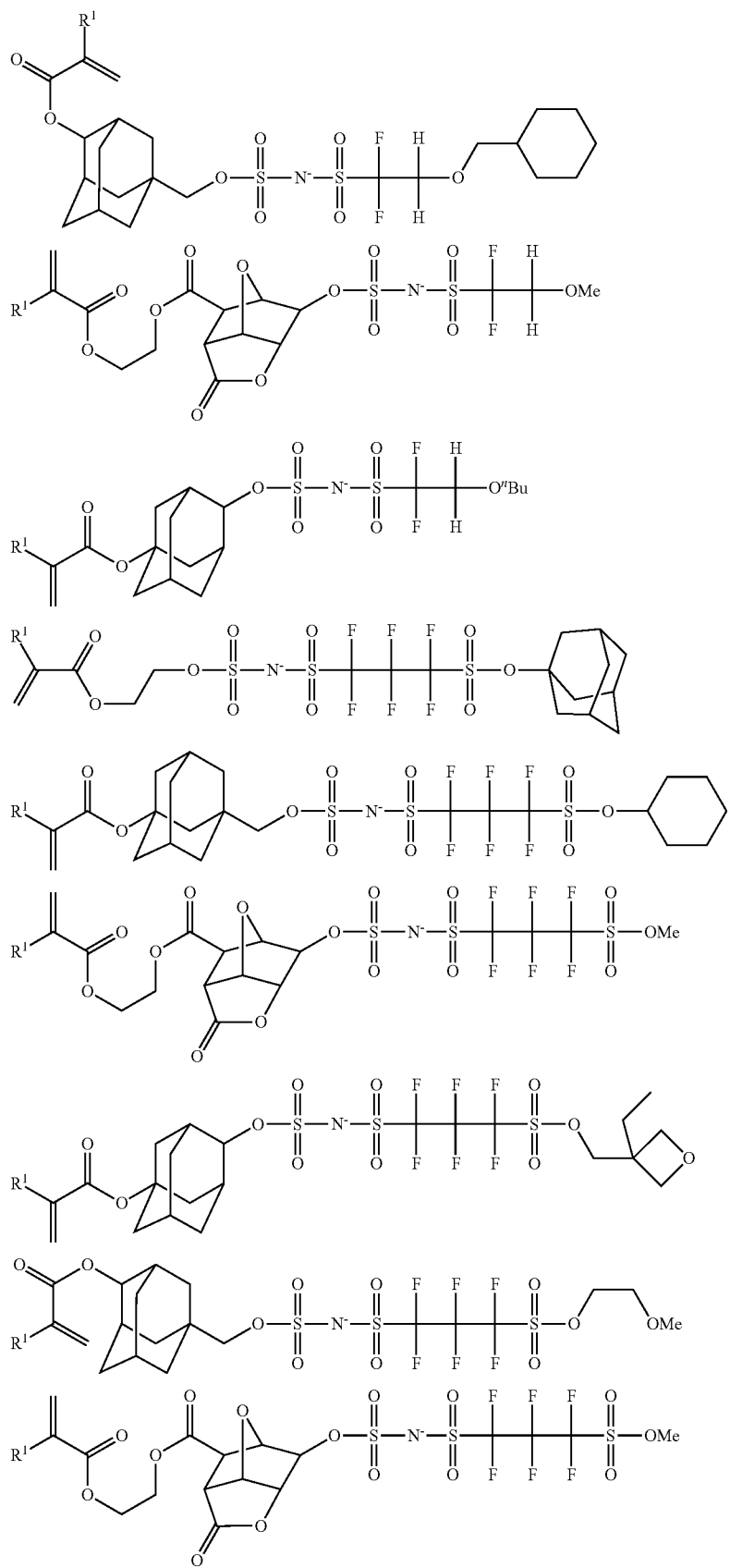

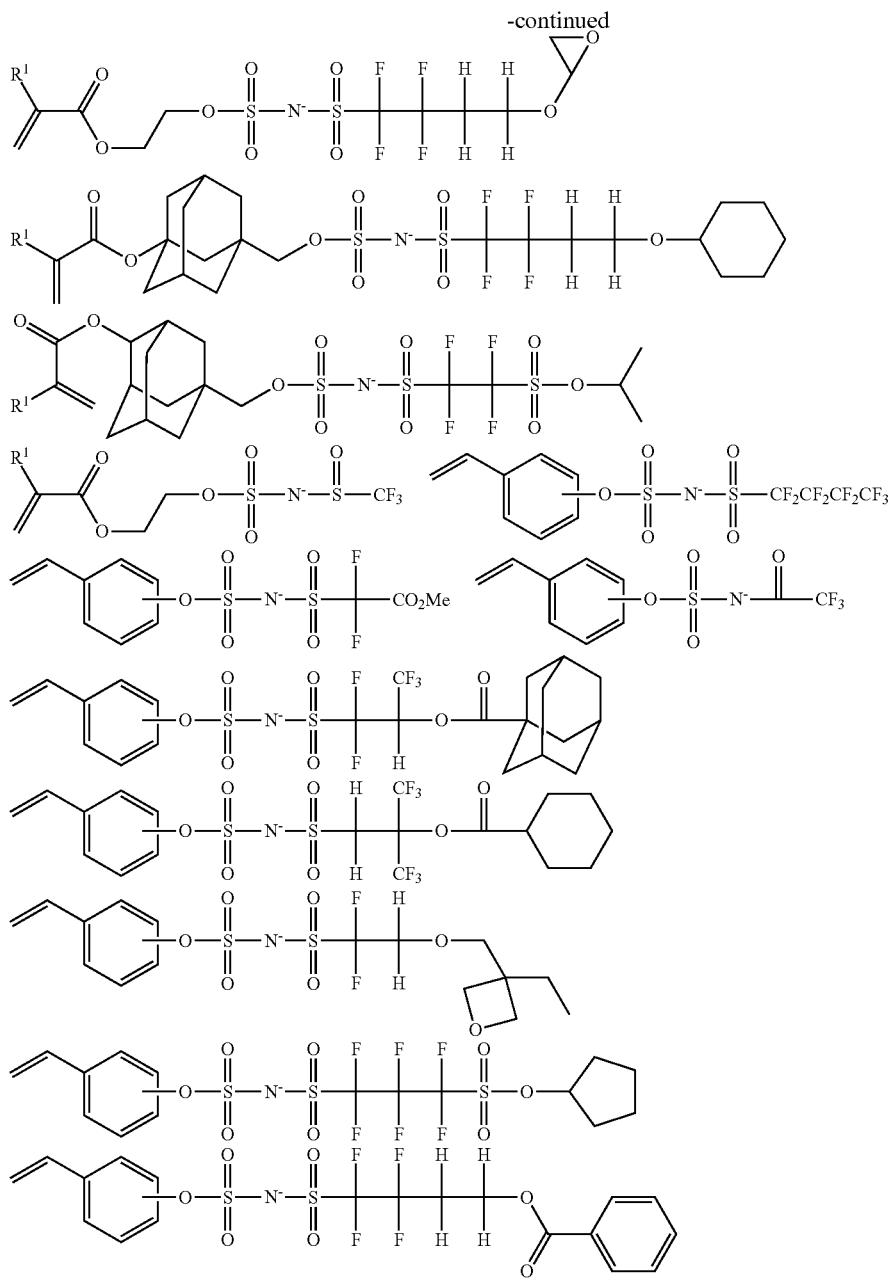

In formula (1), M⁺ is an onium cation. Examples include an oxonium cation ($R_3O^+$), ammonium cation ($R_4N^+$), pyridinium cation ($C_5R_6N^+$), sulfonium cation ($R_3S^+$), phosphonium cation ($R_4P^+$), iodonium cation ($R_2I^+$), and carbonium cation (($C_6R_5)_3C^+$). Inter alia, sulfonium and iodonium cations are preferred, with the sulfonium cation being most preferred.

Herein R is hydrogen or a $C_1$-$C_{30}$ straight, branched or cyclic monovalent hydrocarbon group which may contain a heteroatom, such as alkyl, alkenyl, oxoalkyl, aryl, aralkyl or aryloxoalkyl group. Suitable alkyl groups include methyl, ethyl, propyl, isopropyl, n-butyl, s-butyl, t-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl, thienyl, alkoxyphenyl groups (e.g., 4-hydroxyphenyl, 4-methoxyphenyl, 3-methoxyphenyl, 2-methoxyphenyl, 4-ethoxyphenyl, 4-t-butoxyphenyl, 3-t-butoxyphenyl), alkylphenyl groups (e.g., 2-methylphenyl, 3-methylphenyl, 4-methylphenyl, 4-ethylphenyl, 4-t-butylphenyl, 4-n-butylphenyl, 2,4-dimethylphenyl), alkylnaphthyl groups (e.g., methylnaphthyl, ethylnaphthyl), alkoxynaphthyl groups (e.g., methoxynaphthyl, ethoxynaphthyl, n-propoxynaphthyl, n-butoxynaphthyl), dialkylnaphthyl groups (e.g., dimethylnaphthyl, diethylnaphthyl), and dialkoxynaphthyl groups (e.g., dimethoxynaphthyl, diethoxynaphthyl). Suitable aralkyl groups include benzyl, 1-phenylethyl, and 2-phenylethyl. Suitable aryloxoalkyl groups are 2-aryl-2-oxoethyl groups including 2-phenyl-2-oxoethyl, 2-(1-naphthyl)-2-oxoethyl, 2-(2-naphthyl)-2-oxoethyl. A plurality of R's may bond together to form a ring with the atom to which they are attached and any intervening atom(s). Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

Examples of the iodonium cation include diphenyliodonium, bis(4-methylphenyl)iodonium, bis(4-ethylphenyl)iodonium, bis(4-t-butylphenyl)iodonium, bis(4-(1,1-dimethylpropyl)phenyl)iodonium, 4-methoxyphenylphenyliodonium, 4-t-butoxyphenylphenyliodonium, 4-acryloyloxyphenylphenyliodonium, and 4-methacryloyloxyphenylphenyliodonium, with bis(4-t-butylphenyl)iodonium being preferred.

In the sulfonium cation ($R_3S^+$), any two of three R's may bond together to form a ring with the sulfur atom to which they are attached. Examples of the ring structure are shown below, but not limited thereto.

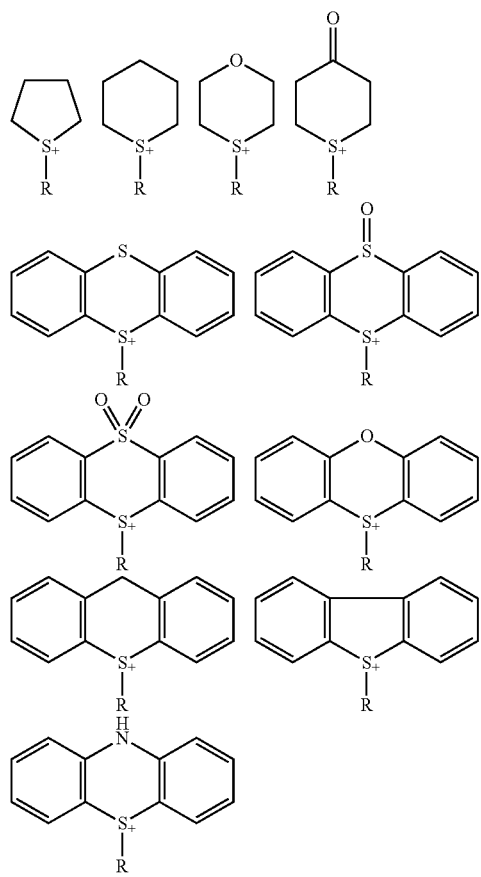

Herein R is as defined above.

Examples of the sulfonium cation are shown below, but not limited thereto.

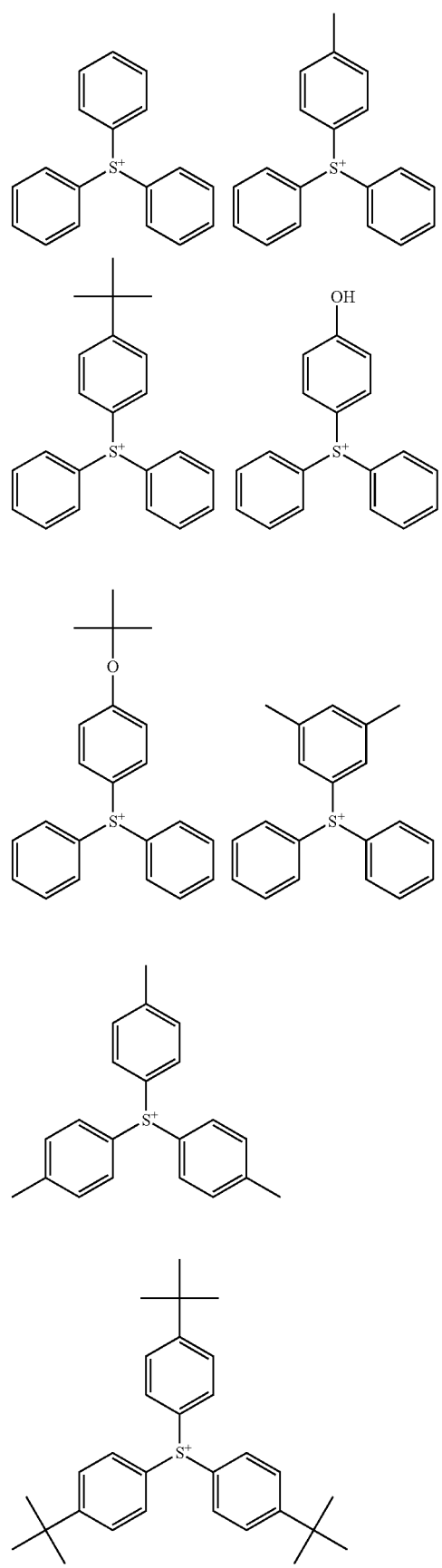

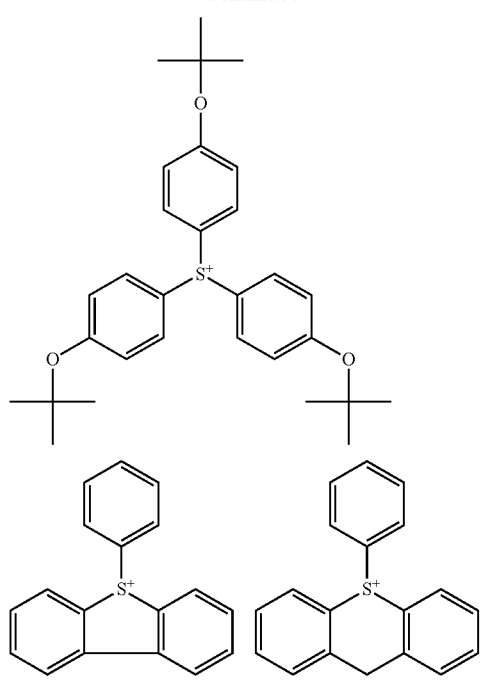
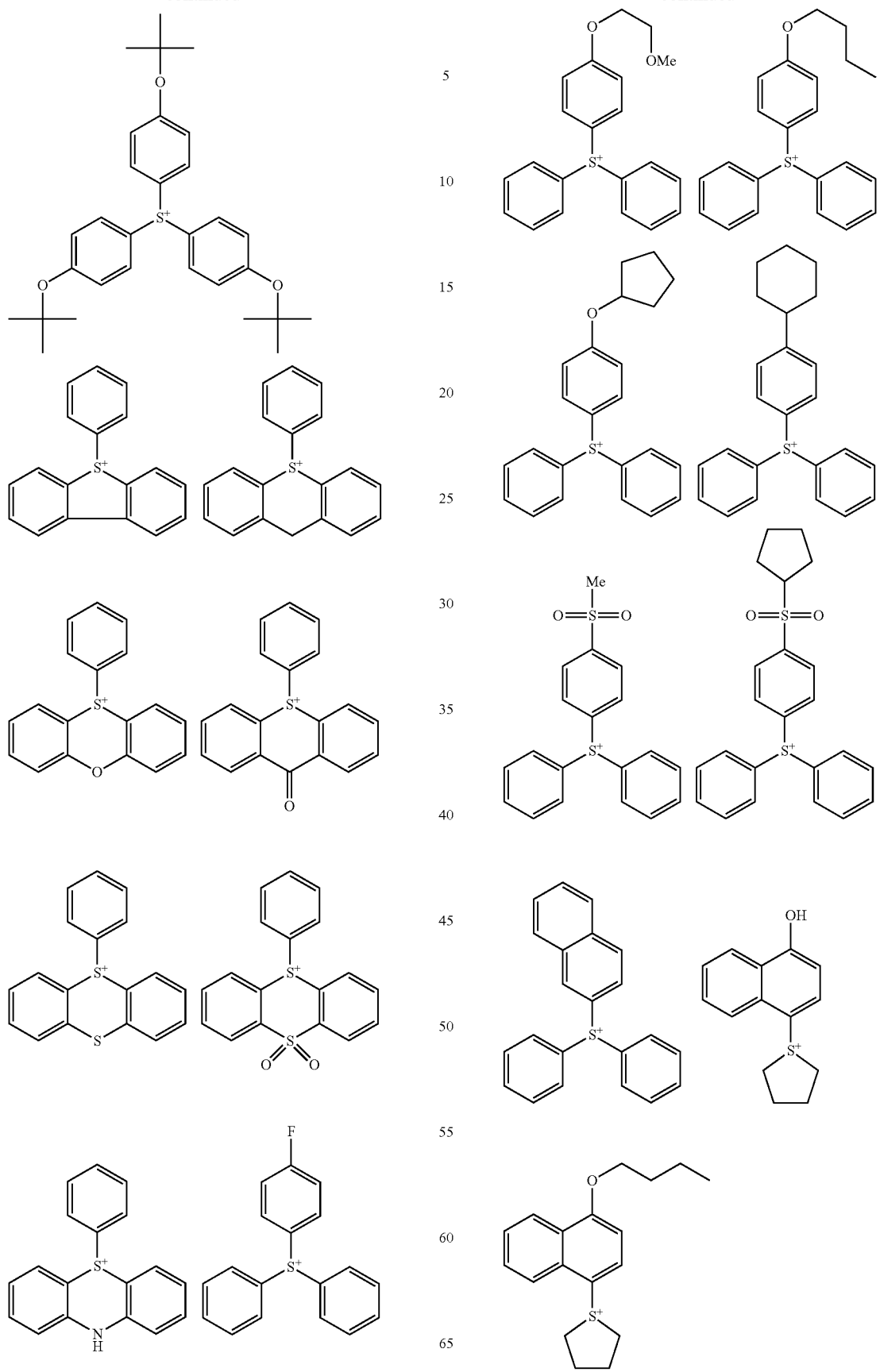

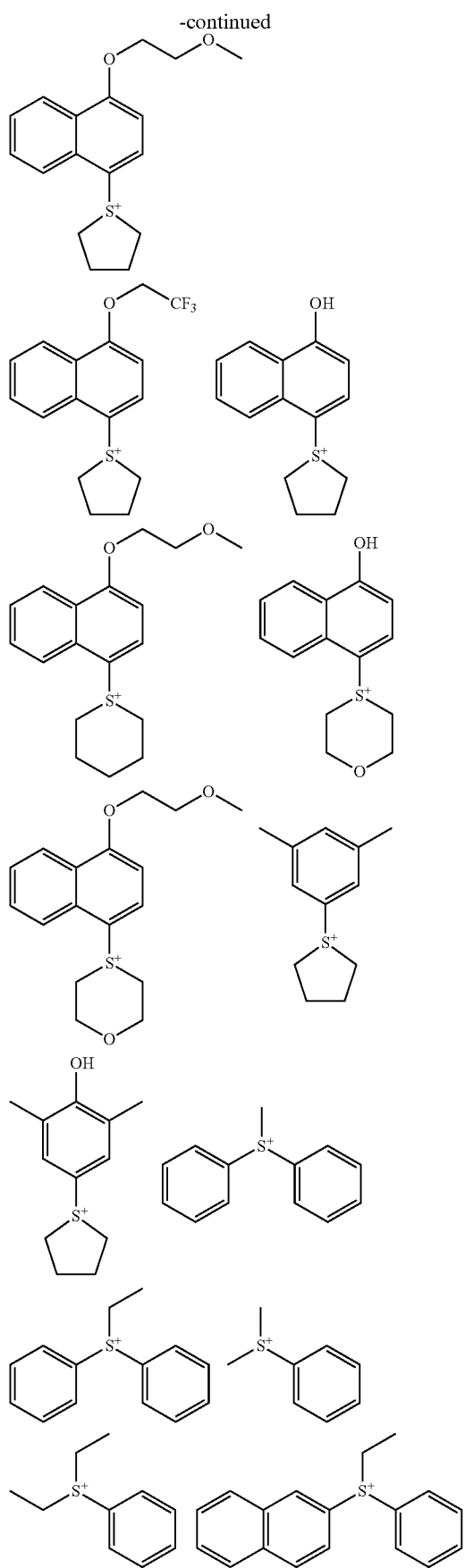
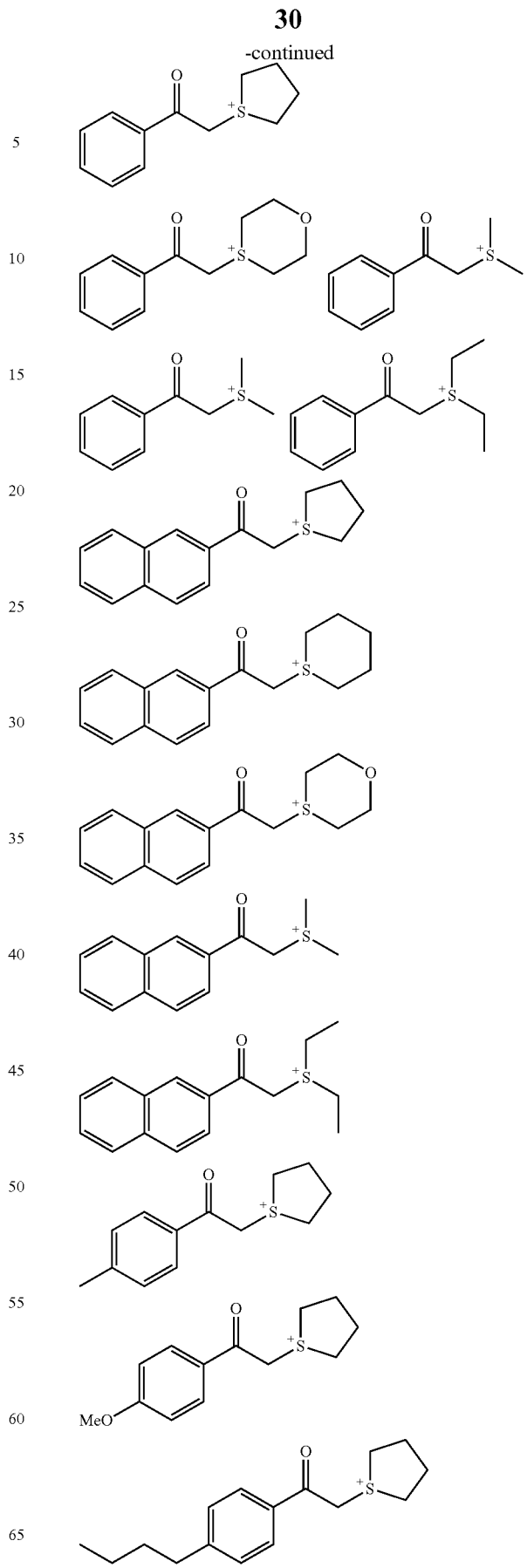

-continued

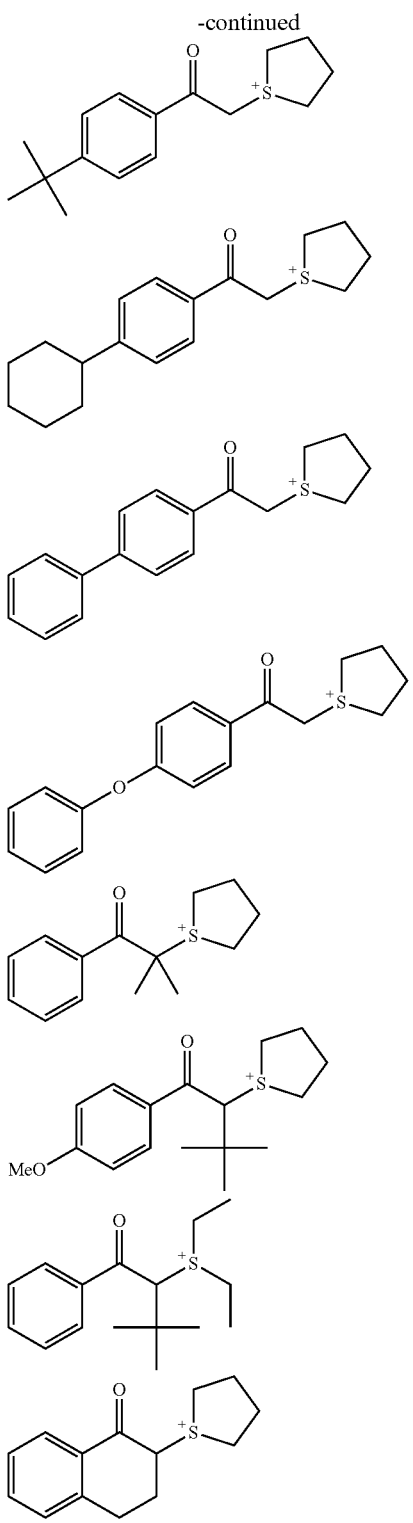

Exemplary structures for the onium salt include arbitrary combinations of anions with cations, both as exemplified above, but are not limited thereto.

The monomer of formula (1) is characterized by a high freedom of structural design because the $L^3$ and $A^1$ moieties of the anion and the cation $M^+$ may be freely designed. An optimum structural design may be made so as to be compliant with variable factors in a particular application includ-ing exposure wavelength, other copolymerized units in the base resin, and a casting solvent in a resist composition.

The inventive monomer may be synthesized according to the following scheme, for example, although the synthesis route is not limited thereto.

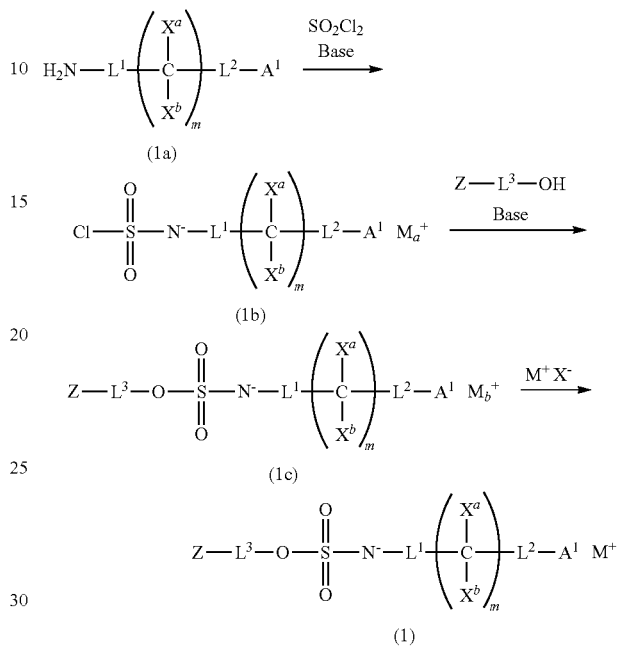

Herein Z, $L^1$, $L^2$, $L^3$, $A^1$, $X^a$, $X^b$, m, and $M^+$ are as defined above, $Ma^+$ and $Mb^+$ each are a cation, and $X^-$ is an anion, First, amide compound (1a) is reacted with sulfuryl chloride under basic conditions to synthesize a sulfuryl chloride derivative (1b) having imide acid structure. At this point, the sulfuryl chloride derivative (1b) may be isolated or passed as such in one-pot to subsequent reaction without isolation.

Examples of the base which can be used herein include amines such as ammonia, triethylamine, pyridine, 4-dimethylaminopyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate; metals such as sodium; metal hydrides such as sodium hydride; metal alkoxides such as sodium methoxide and potassium t-butoxide; organometallic compounds such as butyl lithium and ethylmagnesium bromide; and metal amides such as lithium diisopropylamide, which may be used alone or in admixture. Inter alia, pyridine is preferred from the standpoint of base stability of the intermediate.

An appropriate amount of the base used is 0.5 to 10 moles, more preferably 1.0 to 4.0 moles per mole of amide compound (1a). An appropriate amount of sulfuryl chloride used is 0.5 to 3.0 moles, more preferably 0.8 to 1.5 moles per mole of amide compound (1a). Outside the range, a less amount of the base or sulfuryl chloride may be insufficient to promote reaction whereas an excessive amount may induce side reactions and increase the reactant cost.

A solvent may be used for the reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; aprotic polar solvents such as N,N-dimethylformamide, N,N-dimethylacetamide and dimethyl sulfoxide, which may be used alone or in admixture.

The reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is especially preferred.

Subsequently, sulfuryl chloride derivative (1b) is reacted with an alcohol (Z-L³-OH) under basic conditions to form an imide acid salt (1c).

Examples of the base which can be used herein include amines such as ammonia, triethylamine, pyridine, 4-dimethylaminopyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate; metals such as sodium; metal hydrides such as sodium hydride; metal alkoxides such as sodium methoxide and potassium t-butoxide; organometallic compounds such as butyl lithium and ethylmagnesium bromide; and metal amides such as lithium diisopropylamide, which may be used alone or in admixture.

An appropriate amount of the base used is 0.8 to 10 moles, more preferably 1.0 to 3.0 moles per mole of sulfuryl chloride derivative (1b). An appropriate amount of the alcohol (Z-L³-OH) used is 0.5 to 5.0 moles, more preferably 0.8 to 1.5 moles per mole of sulfuryl chloride derivative (1b). Outside the range, a less amount of the base or alcohol may be insufficient to promote reaction whereas an excessive amount may induce side reactions and increase the reactant cost.

A solvent may be used for the reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; aprotic polar solvents such as N,N-dimethylformamide, N,N-dimethylacetamide and dimethyl sulfoxide, which may be used alone or in admixture.

The reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is especially preferred. As alluded to previously, the reaction course from amide compound (1a) to imide acid salt (1c) may be carried out in one pot. Also the cation may be changed upon reaction from sulfuryl chloride derivative (1b) to imide acid salt (1c) in order to facilitate purification.

Next, the imide acid salt (1c) is subjected to cation exchange using a salt having a desired cation, thereby synthesizing the desired onium salt (1). Ion exchange may be readily carried out by any well-known methods, for example, the method of U.S. Pat. No. 7,511,169 (JP-A 2007-145797).

The structure of the anion moiety may be modified by changing the starting reactants, amide compound (1a) and alcohol (Z-L³-OH). The structure of the cation moiety may be modified by changing the cation used in the last salt exchange step.

Polymer

Another embodiment of the invention is a polymer comprising recurring units derived from the monomer of formula (1). A polymer comprising recurring units having the formula (4) or (5) is preferred.

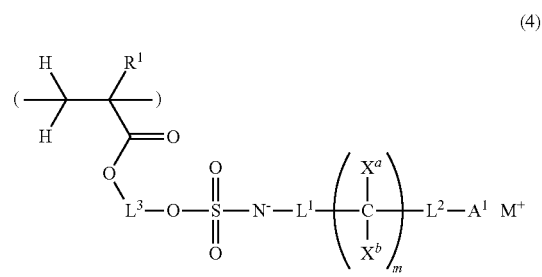

(4)

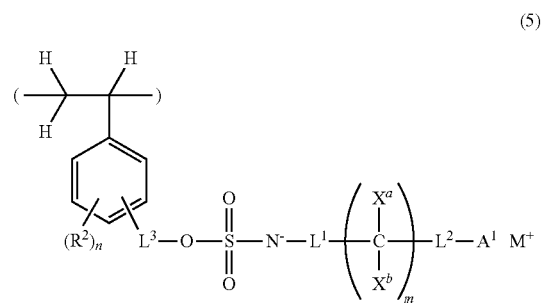

(5)

Herein $L^1$, $L^2$, $L^3$, $A^1$, $X^a$, $X^b$, m, n, $M^+$, $R^1$, and $R^2$ are as defined above.

When the onium cation in the recurring unit of formula (4) or (5) is exposed to high-energy radiation or heat, the polymer changes to a polymer having an imide structure of the formula (4a) or (5a).

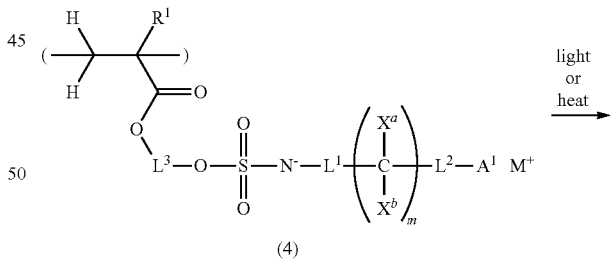

(4)

light or heat →

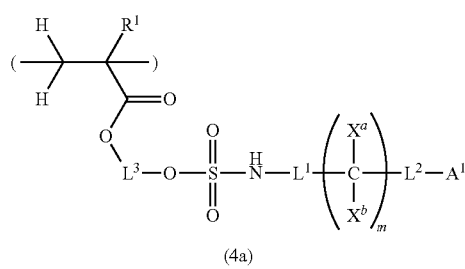

(4a)

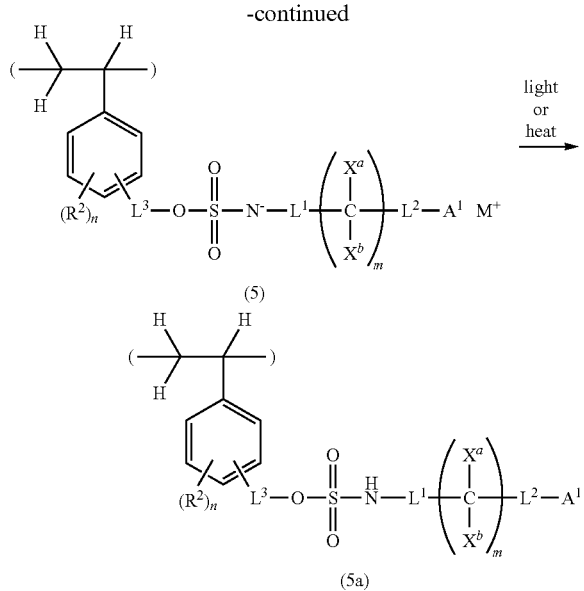

Herein $L^1$, $L^2$, $L^3$, $A^1$, $X^a$, $X^b$, m, n, $M^+$, $R^3$, and $R^2$ are as defined above.

In one example wherein $M^+$ is a sulfonium cation or iodonium cation, the recurring unit (4) or (5) is photo-decomposed into imidic acid (4a) or (5a). In another example wherein $M^+$ is an ammonium cation, the recurring unit (4) or (5) is thermally decomposed into imidic acid (4a) or (5a).

The polymer has a PAG anion moiety incorporated as the recurring unit. This enables to substantially suppress the diffusion of generated acid. Such a concept is known from several patent documents. For example, JP-A 2008-133448, JP-A 2010-077404, JP-A 2007-328060, and JP-A 2011-118310 describe a resist composition comprising a polymer having a PAG with a specific anion structure incorporated as the recurring unit. These resist compositions, however, are inferior in lithography properties including sensitivity, MEF, LWR and CDU to the resist composition comprising the inventive polymer as a base resin. The reason is presumed below.

In the resist composition comprising the polymer comprising recurring units of formula (4) or (5) as the base resin, the unit generates a corresponding imide acid upon light exposure. The imide acid exhibits a pKa value of about −7.0 to −2.0. In particular, it exhibits a pKa value of about −7.0 to −4.0, i.e., a very high acidity when $L^1$ in the formula is a sulfonyl bond. The photo-decomposable recurring unit described in the above-cited patent documents is perfluorosulfonic acid having a fluorine atom (or electron attractive group) at α- or β-position relative to the sulfo group. For example, one of the constitutional units having a photo-decomposable group described in the cited patent documents is triphenylsulfonium 1,1,3,3,3-pentafluoro-2-methacryloyloxypropane-1-sulfonate. This photo-decomposable unit generates an acid having a pKa value of about −3.0 whereas the PAG of the invention generates an imidic acid having an acidity which is stronger than the indicated value by a factor of about 1 to about 10,000. That is, the resist composition comprising the inventive polymer as base resin has a higher sensitivity, leading to an improvement in throughput of the processing system. For the same reason, it is unlikely that the resist composition is reduced in sensitivity when the content of an acid diffusion regulator or quencher is increased. This means that the resist composition may more widely vary in formulation. As a result, a resist composition having a good balance of lithography properties including sensitivity, MEF, LWR, and CDU is available. It is noted that the pKa value is computed using ACD/ChemSketch of Advanced Chemistry Development Inc. (ACD/Labs).

Some of the exemplary imide acid salts described in JP-A 2011-118310 are monomers having an asymmetric imide acid salt structure. These monomers are not of ideal design because a monomer having a high fluorine incorporation rate may be localized in a resist material to degrade lithography properties whereas a fluorine-free monomer has a low acidity and an insufficient sensitivity so that a resist material may have a lower sensitivity.

Also known is a resist composition comprising a polymer containing recurring units derived from a monomer having a polymerizable group in the cation moiety as PAG. Of such polymers, recurring units having an imide acid structure in the anion moiety are also known, and the imide acid generated therefrom undergoes substantial diffusion, leading to degradation of lithography properties.

As compared with a resist composition comprising a polymer in which a PAG having the anion structure described in the cited patent document is incorporated as the recurring unit, the resist composition comprising the polymer containing recurring units derived from the inventive monomer as base resin is improved in compatibility and reduced in defects. The reason is presumed below.

In general, imide and methide acid salts are compatible as compared with perfluoroalkanesulfonic acid salts. The inventive monomer is improved in compatibility because it has an asymmetric structure with respect to the nitrogen atom serving as the imide acid-generating site, which causes disruption to molecular symmetry. As compared with recurring units capable of generating perfluoroalkanesulfonic acid, the recurring units of formula (4) or (5) can be incorporated in a base resin at a high proportion without accompanying defect generation. As a result, the resist can be increased in sensitivity.

Resist Composition

A further embodiment of the invention is a resist composition comprising (A) a base resin containing the inventive polymer, (B) an organic solvent, (C) an additive photoacid generator other than the onium salt having formula (1), (D) a quencher, (E) a surfactant which is insoluble or substantially insoluble in water and soluble in alkaline developer, and/or a surfactant which is insoluble or substantially insoluble in water and alkaline developer (also referred to as hydrophobic resin), and (F) another component(s). Components (C), (D), (E), and (F) are optional, that is, may be added if necessary.

Component A

The base resin (A) included in the resist composition contains the polymer defined above. Preferred is a polymer comprising recurring units having the formula (4) or (5), which is referred to as Polymer A, hereinafter. More preferably, Polymer A further comprises recurring units of at least one type selected from recurring units having the formulae (6) and (7).

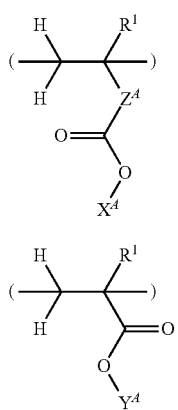

In formulae (6) and (7), $R^1$ is as defined above. $Z^A$ is a single bond, phenylene group, naphthylene group or (backbone)-C(=O)—O—Z'—, wherein Z' is a $C_1$-$C_{10}$ straight, branched or cyclic alkylene group which may contain a hydroxyl radical, ether bond, ester bond or lactone ring, or phenylene group or naphthylene group. $X^A$ is an acid labile group. $Y^A$ is hydrogen or a polar group having at least one structure selected from among hydroxyl, cyano, carbonyl, carboxyl, ether bond, ester bond, sulfonic acid ester bond, carbonate bond, lactone ring, sultone ring and carboxylic anhydride.

Examples of the structure having formula (6) wherein $Z^A$ is a variant are shown below. Notably, $R^1$ and $X^A$ are as defined above.

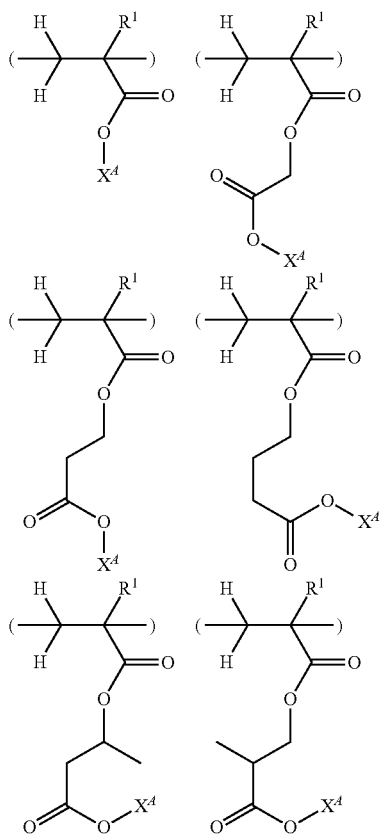
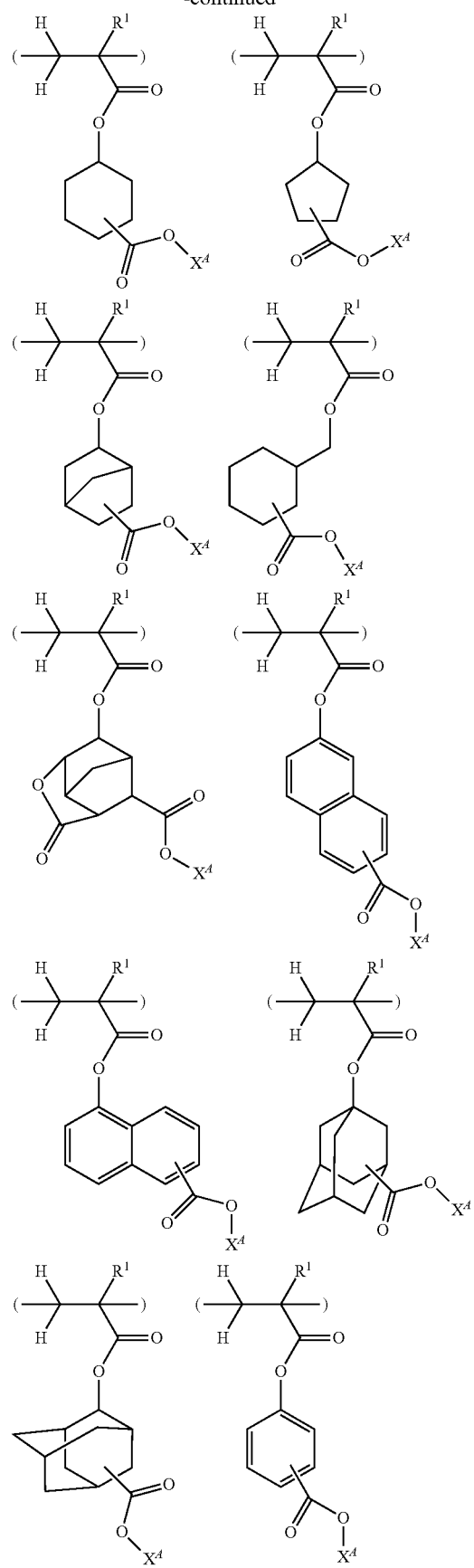

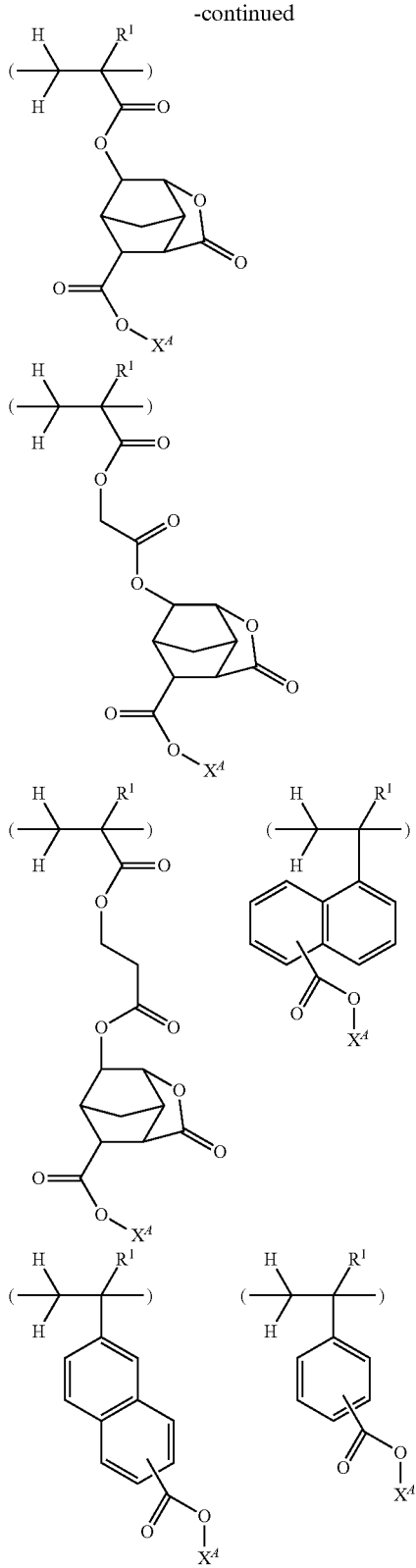

Under the action of acid, a polymer comprising recurring units of formula (6) is decomposed to generate carboxylic acid, turning to be an alkali soluble polymer.

The acid labile group represented by $X^A$ may be selected from a variety of such groups. Examples of the acid labile group include groups of the following formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

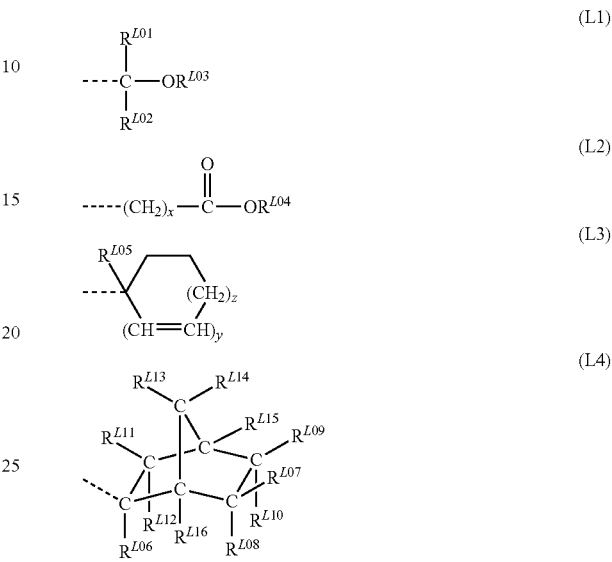

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, s-butyl, t-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which a heteroatom such as oxygen intervenes between carbon atoms. Suitable alkyl groups are as exemplified above for $R^{L01}$ and $R^{L02}$. Illustrative examples of the substituted alkyl groups are shown below.

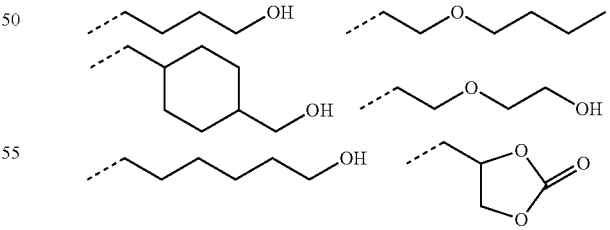

A pair of $R^{L01}$ and $R^{L03}$, $R^{L01}$ and $R^{L03}$, or $R^{L02}$ and $R^{L03}$ may bond together to form a ring with the carbon and oxygen atoms to which they are attached. Ring-forming participants of $R^{L01}$, $R^{L02}$ and $R^{L03}$ represent a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are t-butyl, t-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-t-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, s-butyl, t-butyl, t-pentyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups. Letter y is equal to 0 or 1, z is an integer of 0 to 3, and 2y+z is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Ring-forming participants of $R^{L07}$ to $R^{L16}$ represent a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

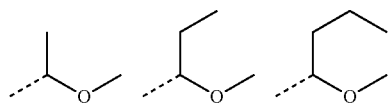

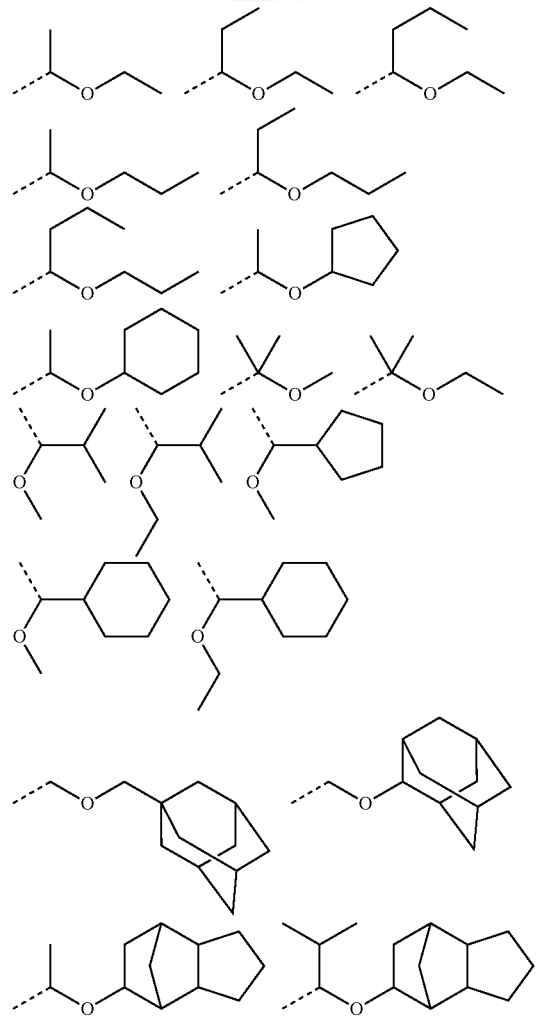

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethyloyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-s-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups having formula (L4), groups having the following formulas (L4-1) to (L4-4) are preferred.

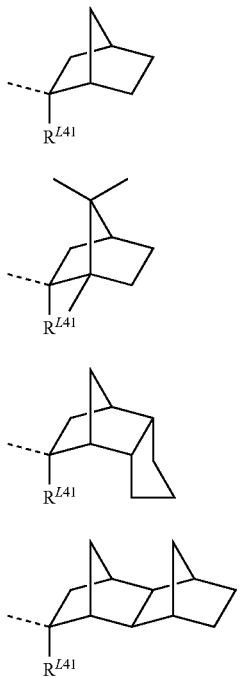

(L4-1)

(L4-2)

(L4-3)

(L4-4)

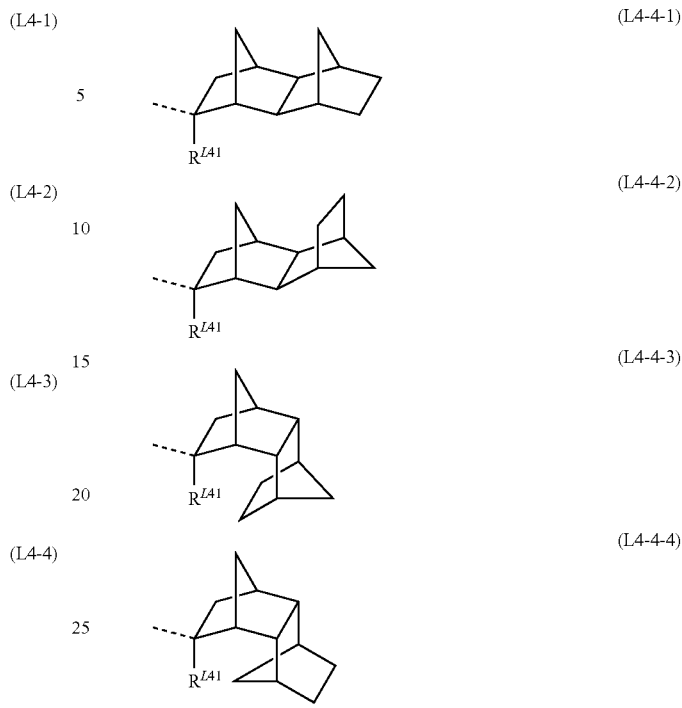

(L4-4-1)

(L4-4-2)

(L4-4-3)

(L4-4-4)

In formulas (L4-1) to (L4-4), the broken line denotes a bonding site and direction. $R^{L41}$ is each independently a monovalent hydrocarbon group, typically a $C_1$-$C_{10}$ straight, branched or cyclic alkyl group, such as methyl, ethyl, propyl, isopropyl, n-butyl, s-butyl, t-butyl, t-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When $X^A$ is an acid labile group of formula (L4), a plurality of stereoisomers may be contained.

For example, the formula (L4-3) represents one or a mixture of two selected from groups having the following formulas (L4-3-1) and (L4-3-2).

Herein $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

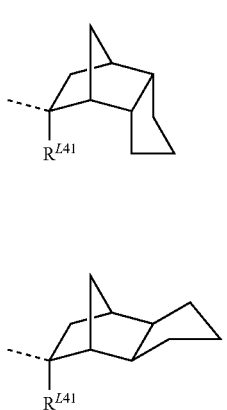

(L4-3-1)

(L4-3-2)

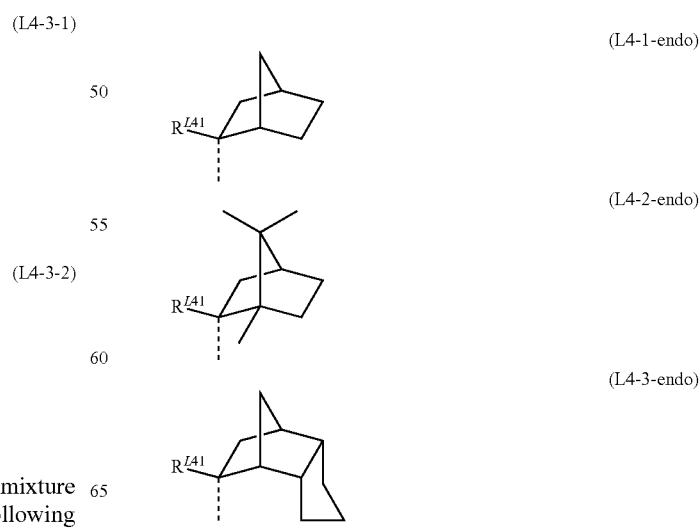

(L4-1-endo)

(L4-2-endo)

(L4-3-endo)

Similarly, the formula (L4-4) represents one or a mixture of two or more selected from groups having the following formulas (L4-4-1) to (L4-4-4).

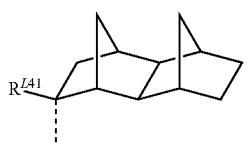

(L4-4-endo)

Herein $R^{L41}$ is as defined above.

Illustrative examples of the acid labile group of formula (L4) are given below, but not limited thereto.

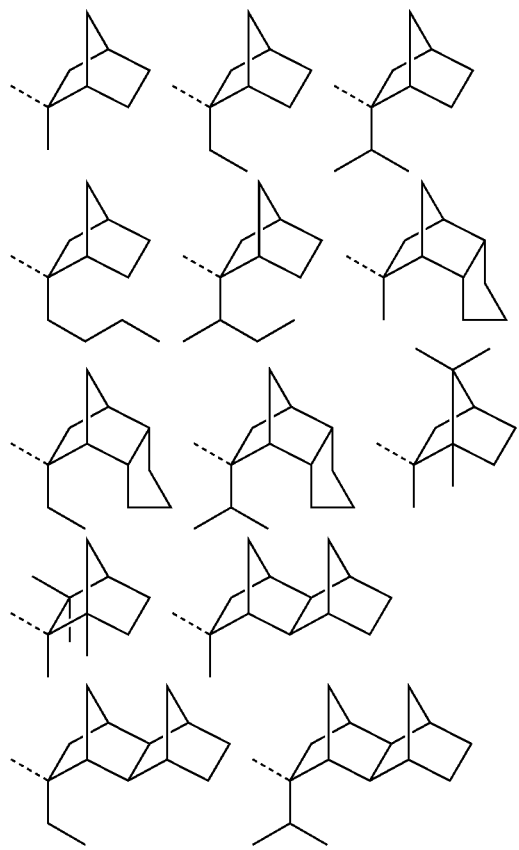

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups, represented by $X^A$, are as exemplified for $R^{LO4}$.

Illustrative examples of the recurring units of formula (6) are given below, but not limited thereto. Herein $R^1$ is as defined above.

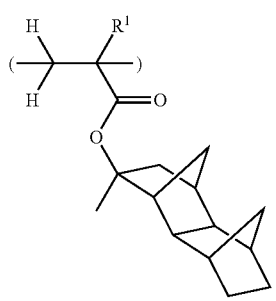

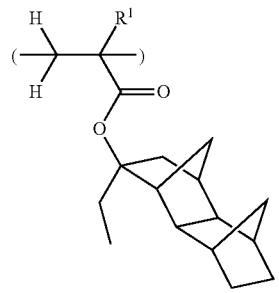

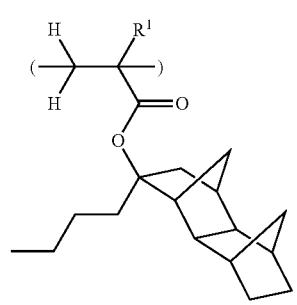

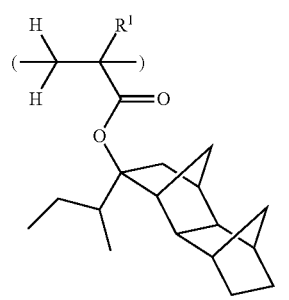

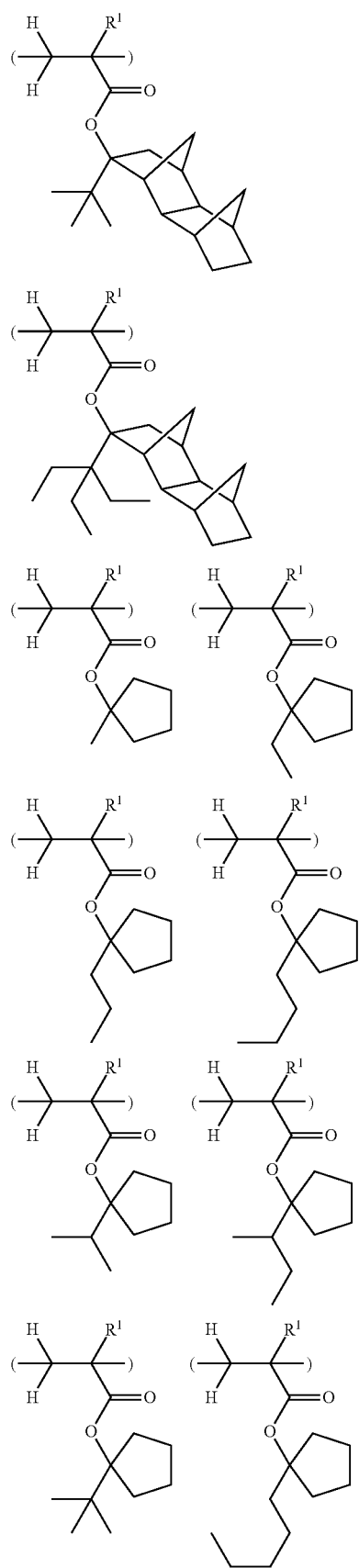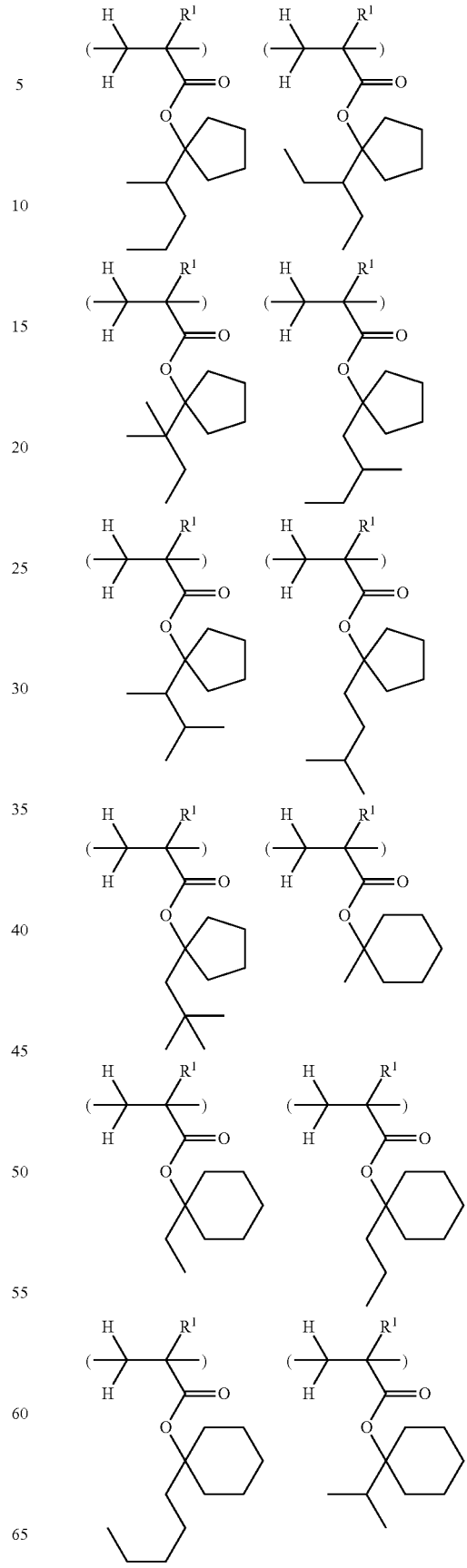

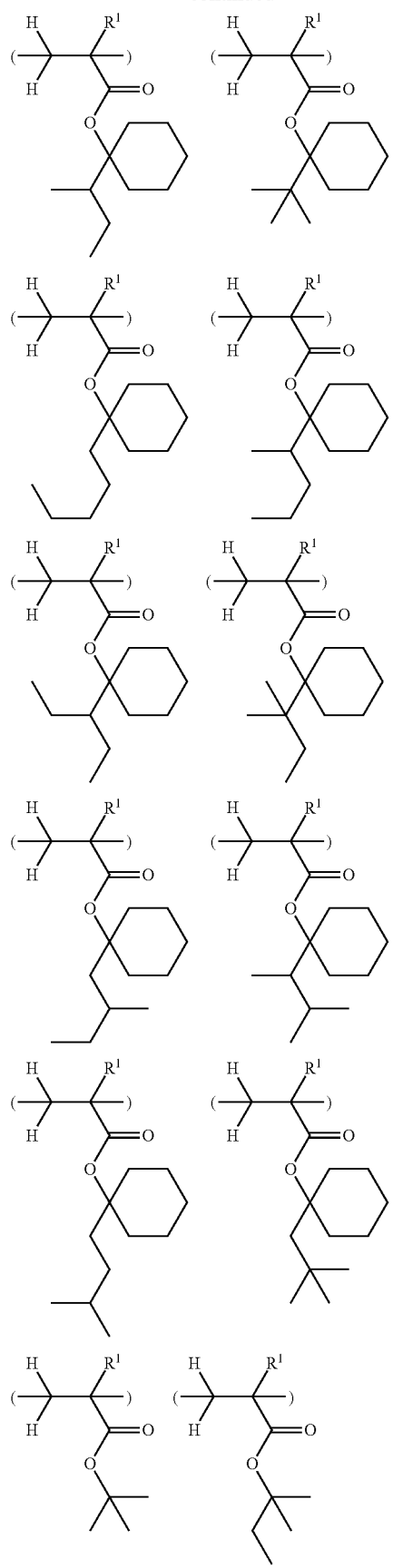
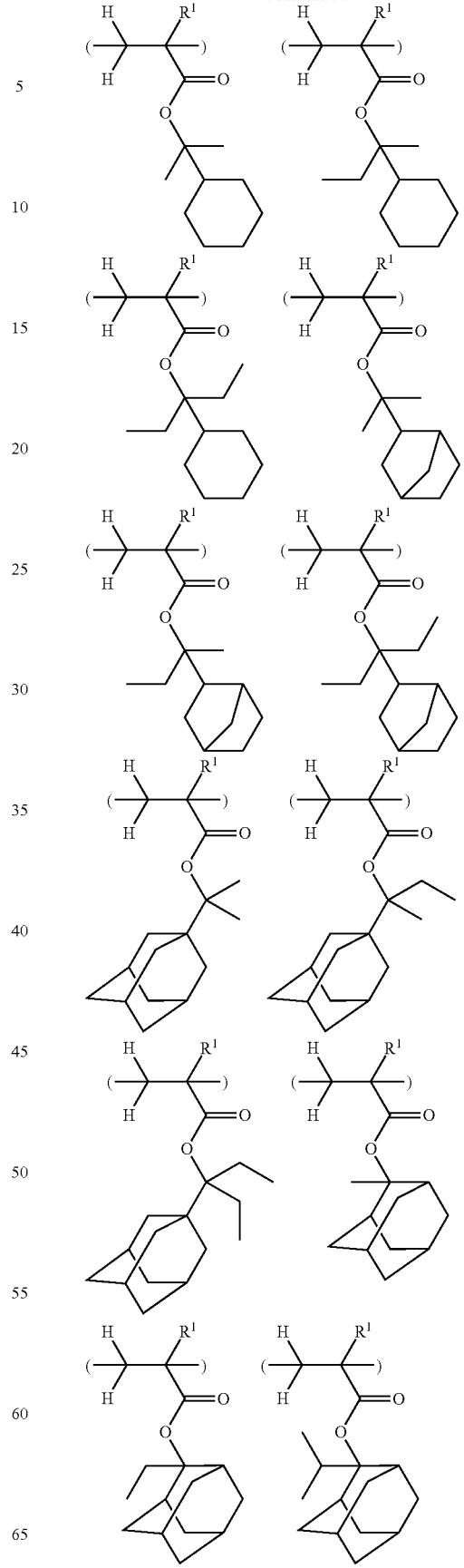

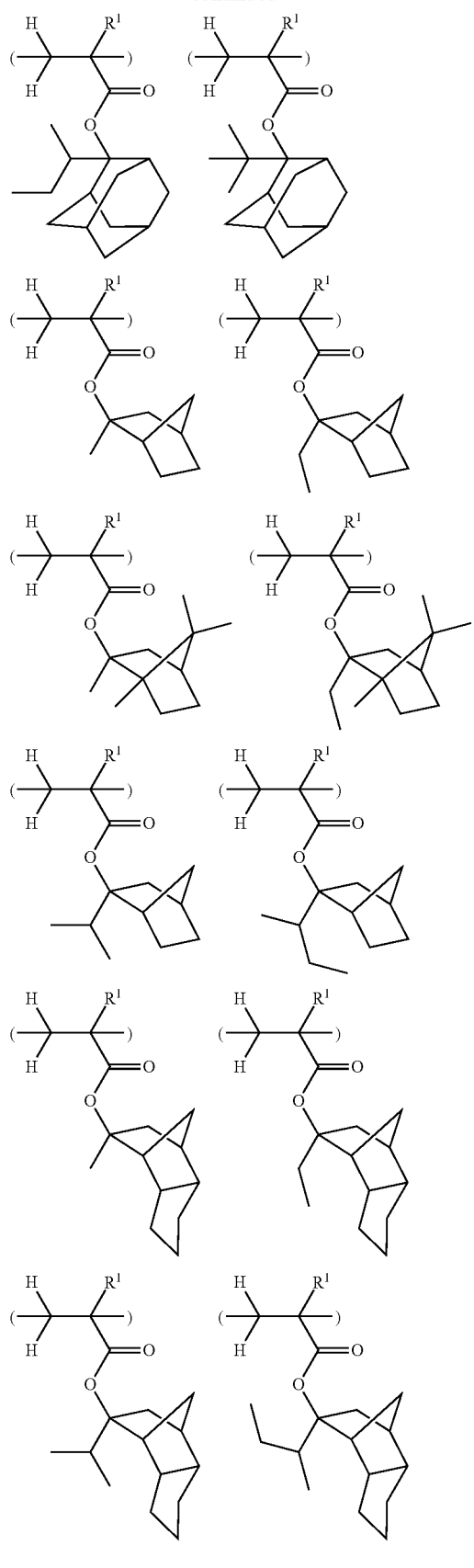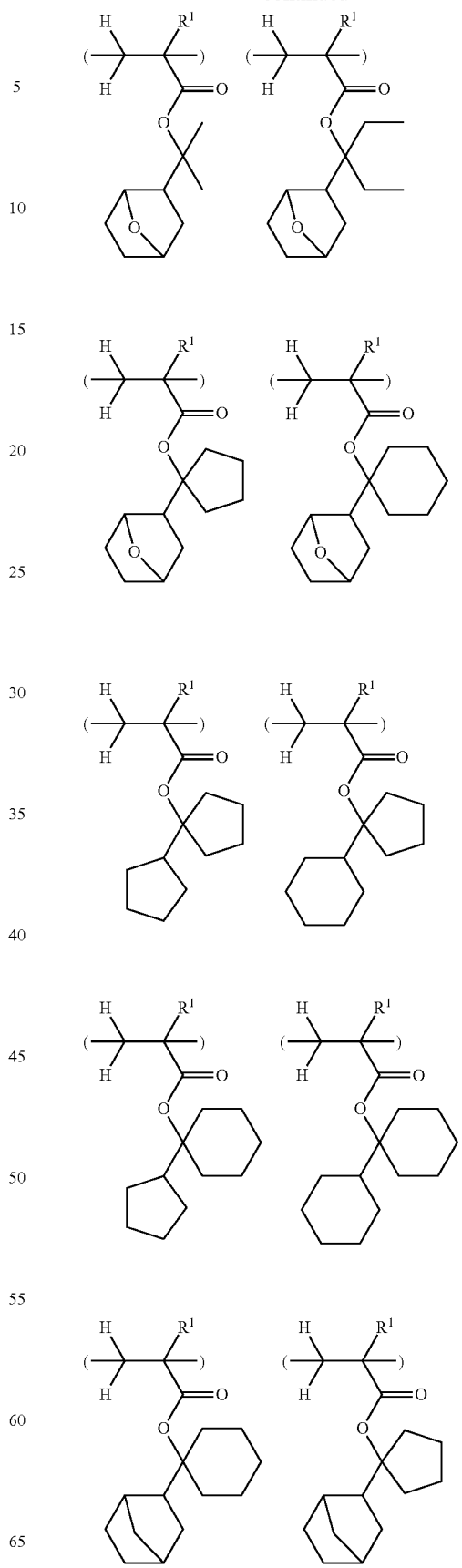

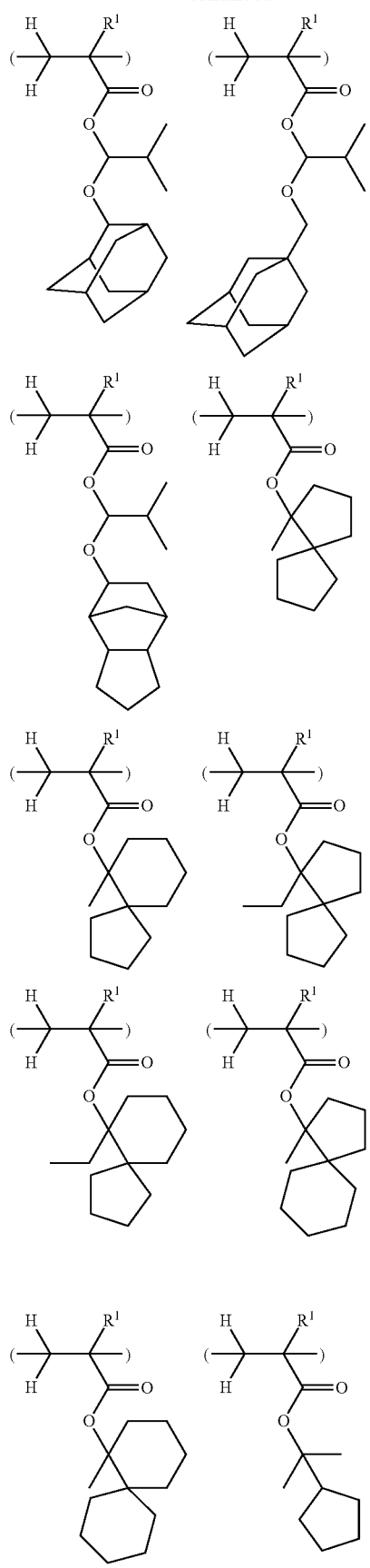
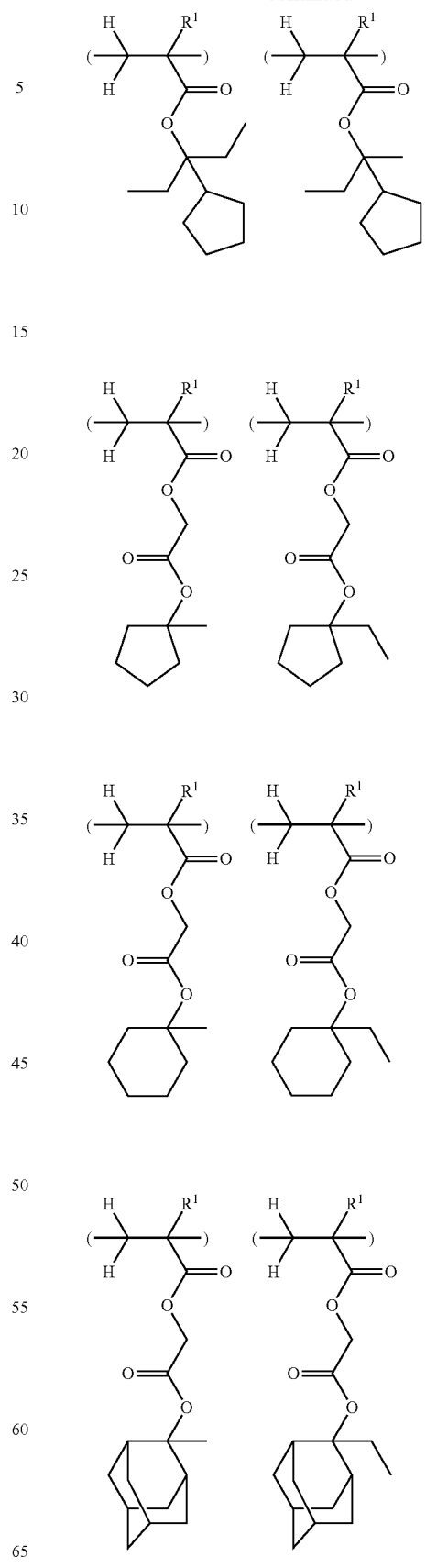

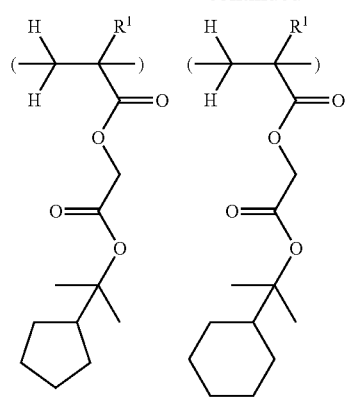
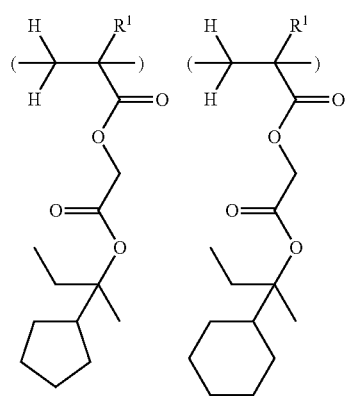
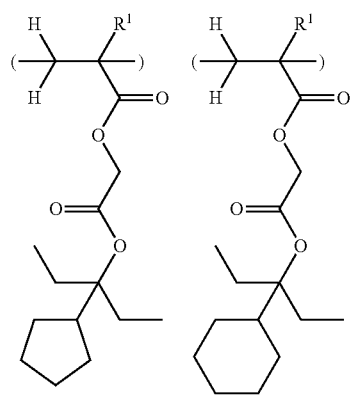
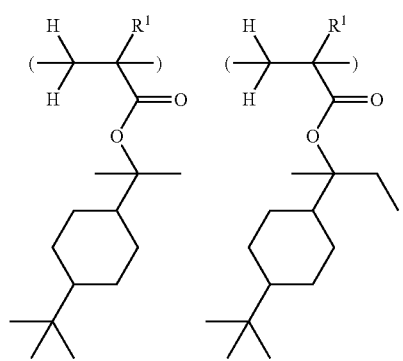
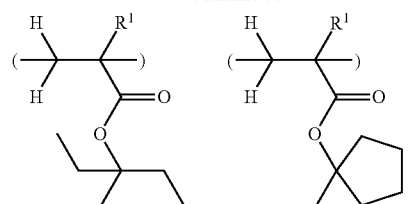
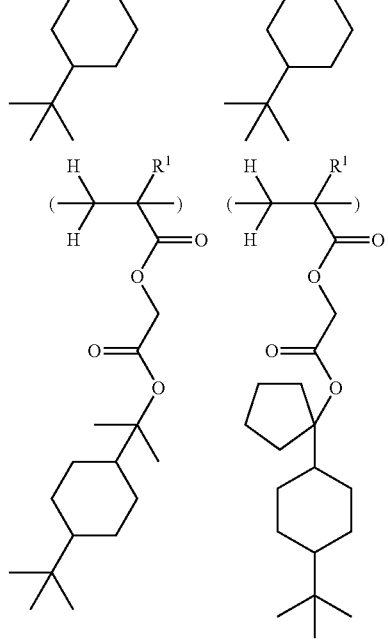
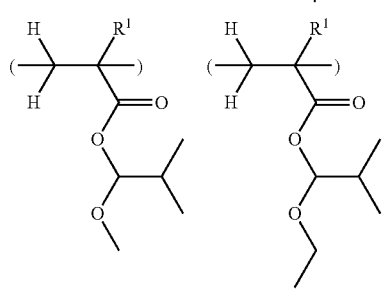
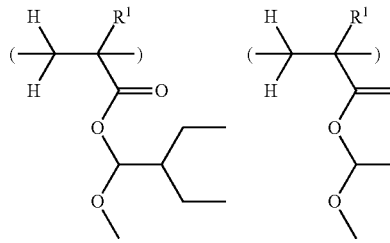
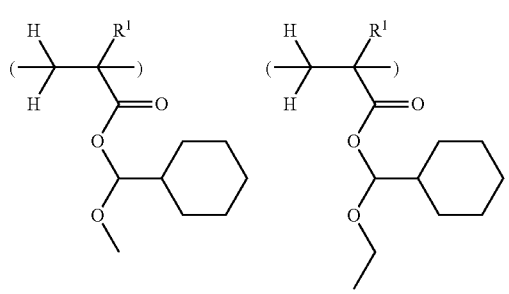

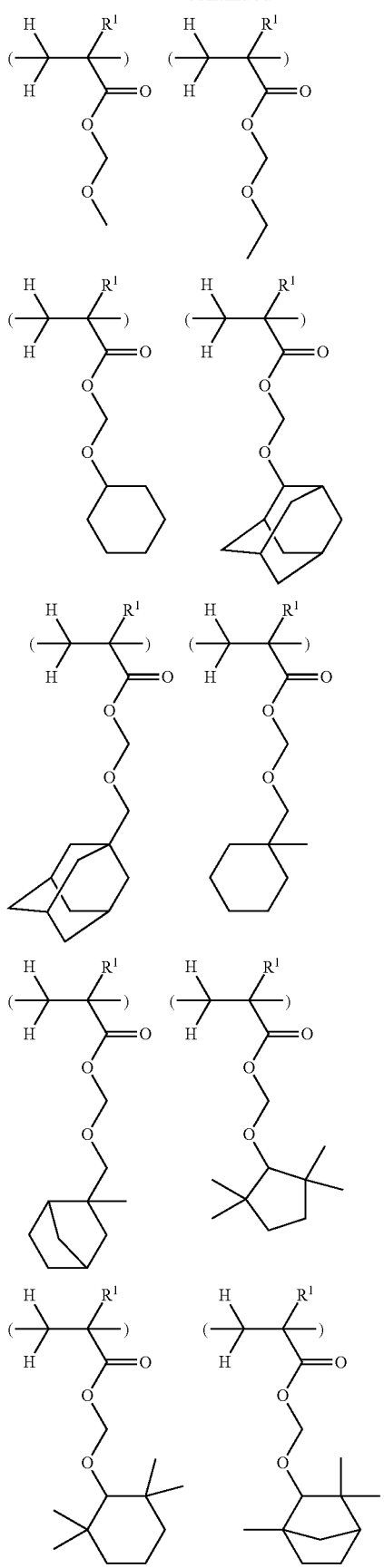

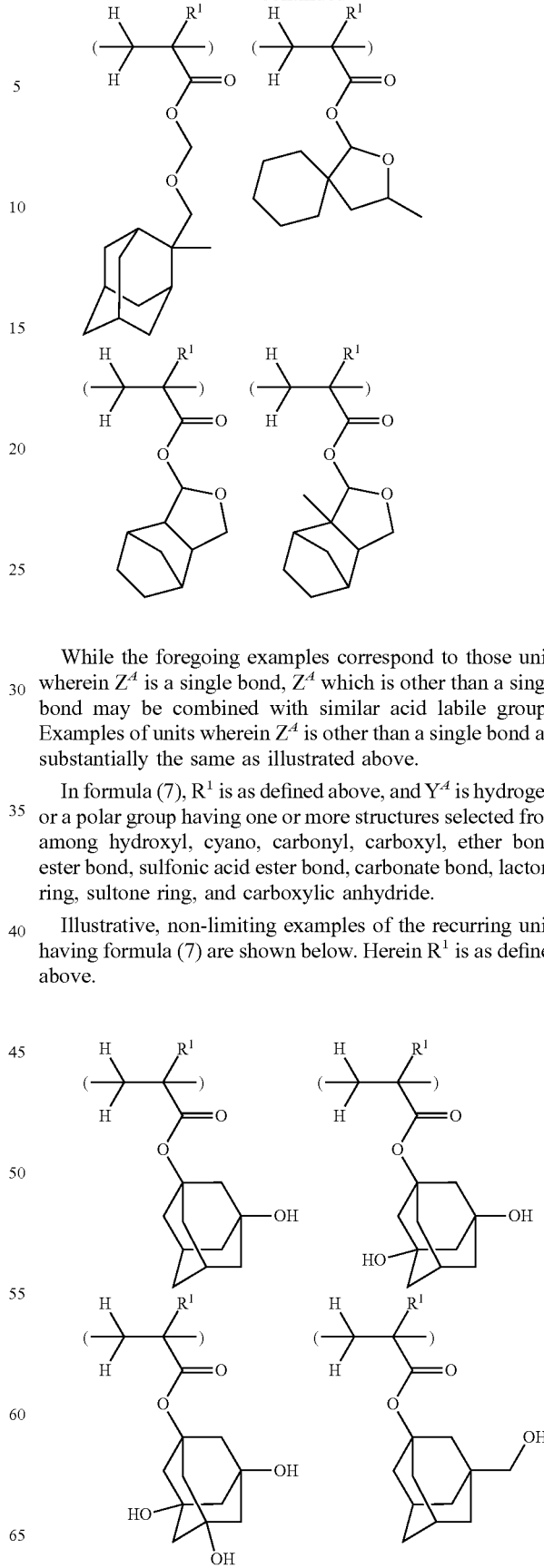

While the foregoing examples correspond to those units wherein $Z^A$ is a single bond, $Z^A$ which is other than a single bond may be combined with similar acid labile groups. Examples of units wherein $Z^A$ is other than a single bond are substantially the same as illustrated above.

In formula (7), $R^1$ is as defined above, and $Y^A$ is hydrogen, or a polar group having one or more structures selected from among hydroxyl, cyano, carbonyl, carboxyl, ether bond, ester bond, sulfonic acid ester bond, carbonate bond, lactone ring, sultone ring, and carboxylic anhydride.

Illustrative, non-limiting examples of the recurring units having formula (7) are shown below. Herein $R^1$ is as defined above.

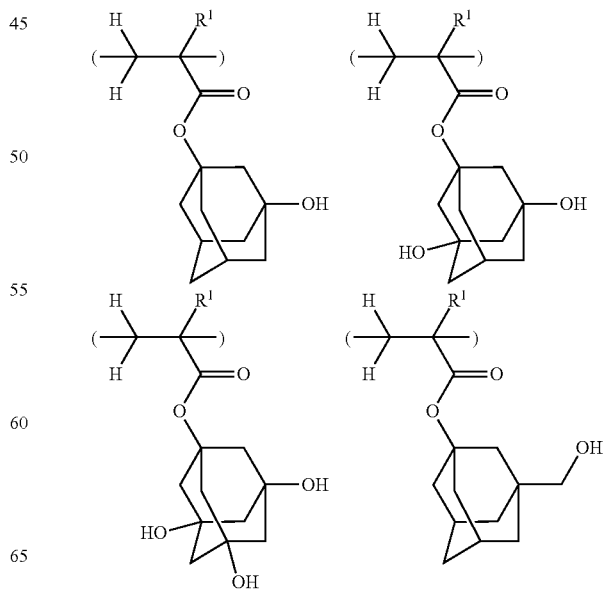

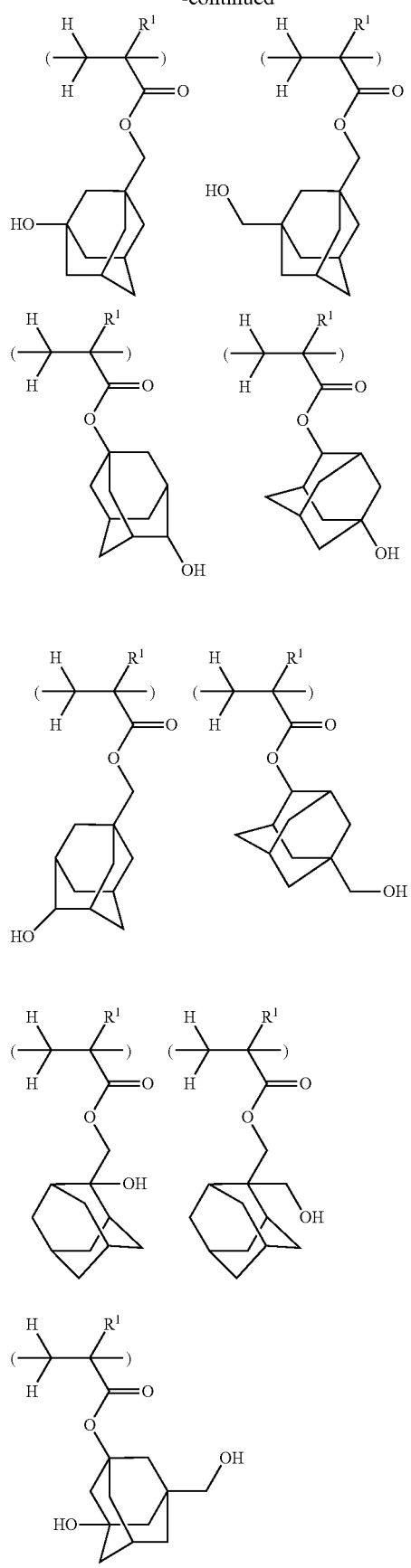
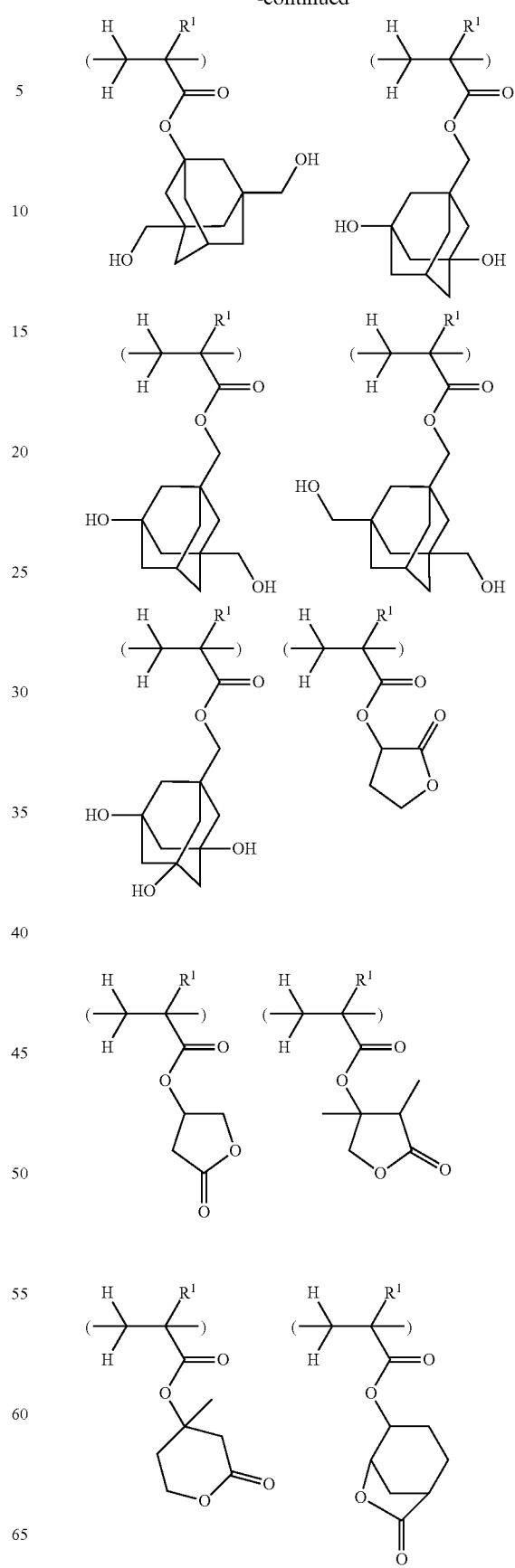

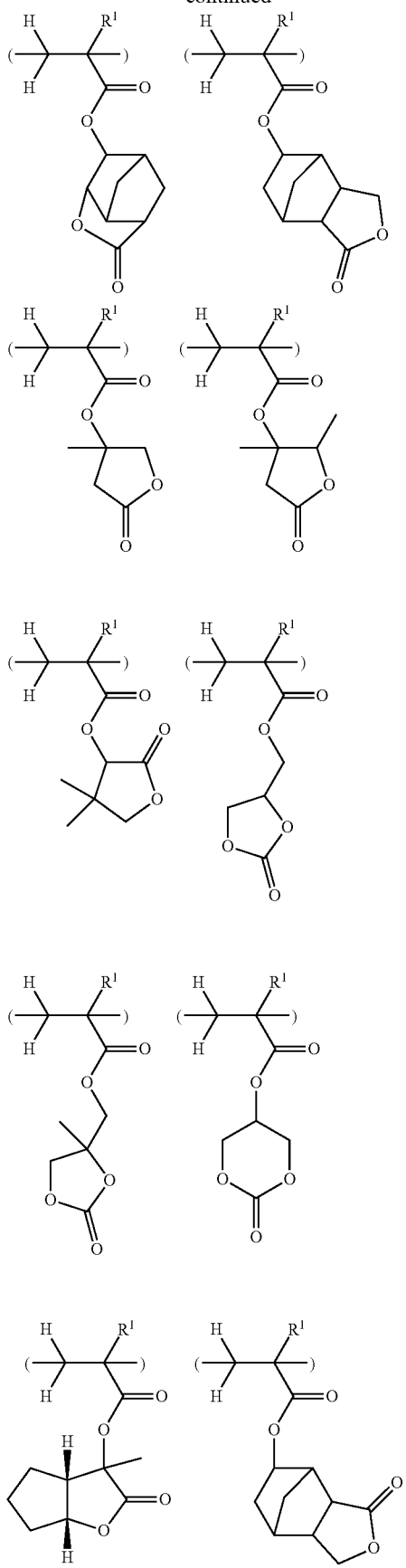
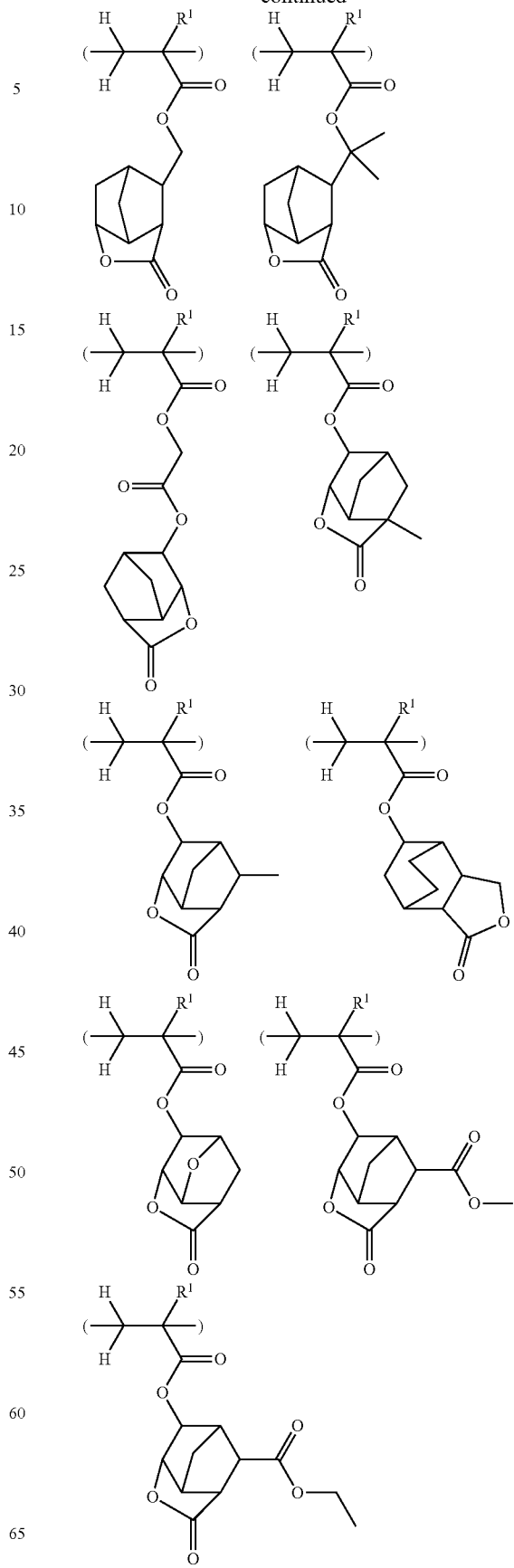

-continued
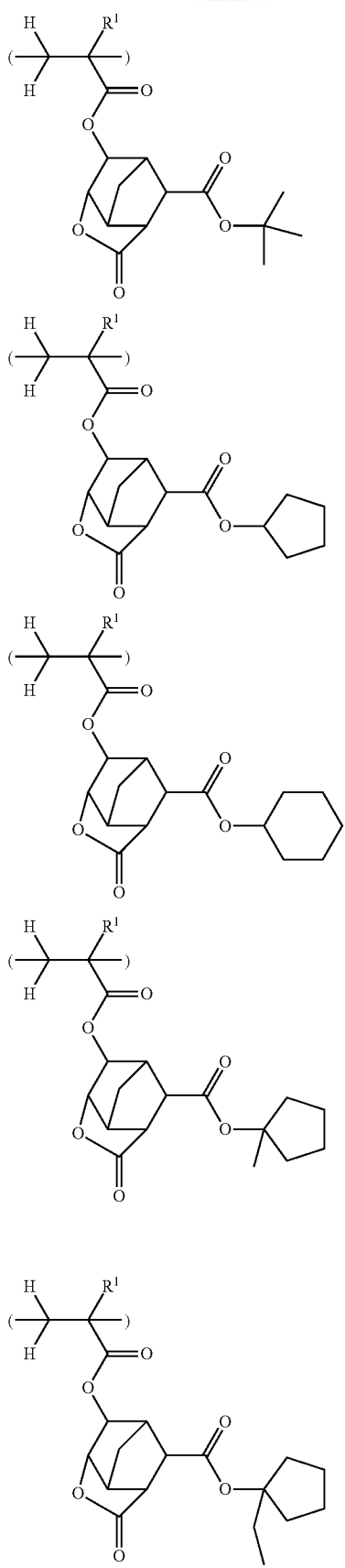
-continued
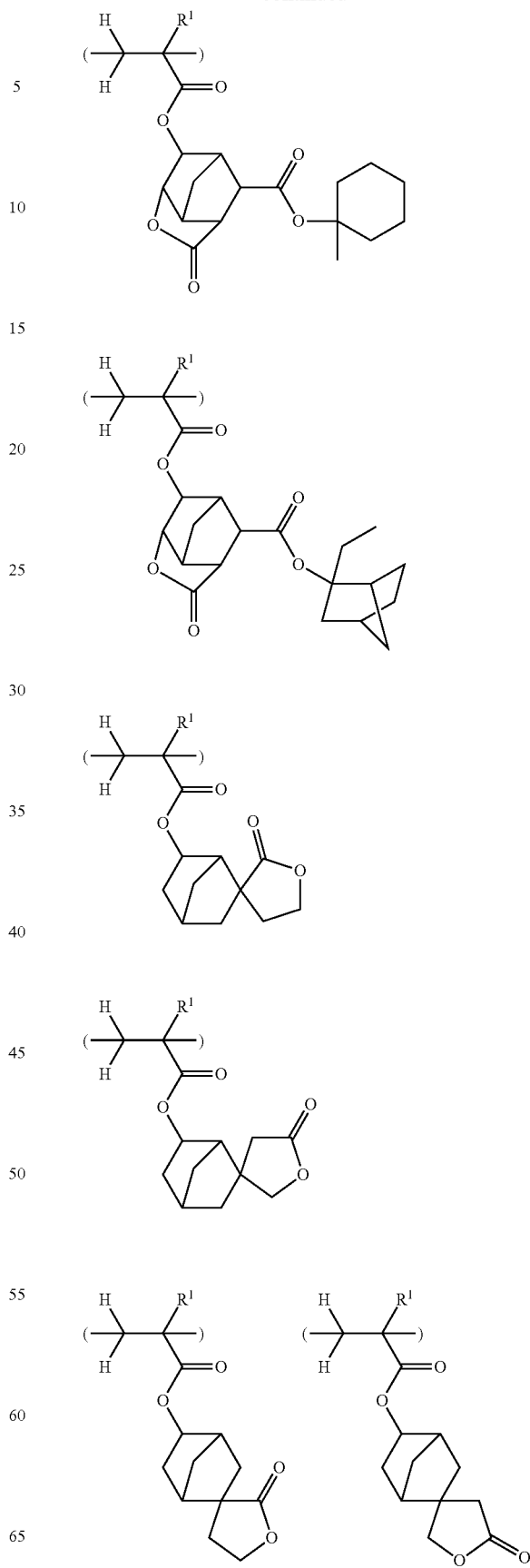

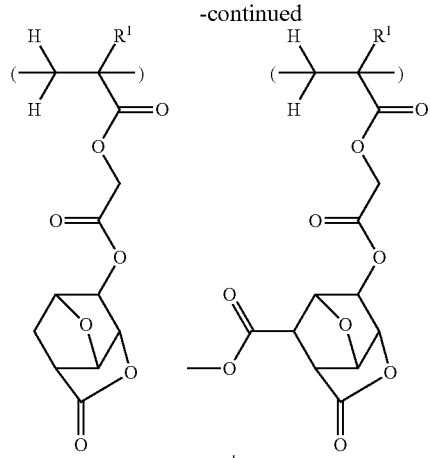
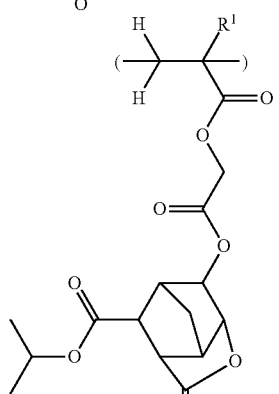
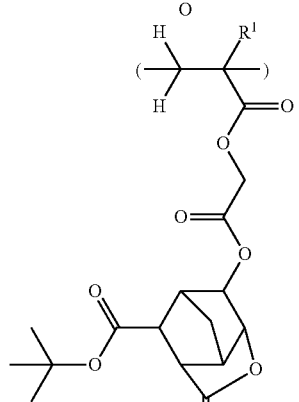
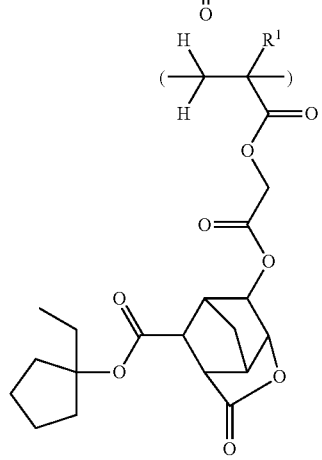
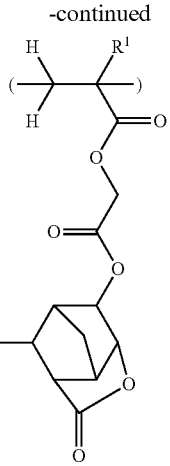
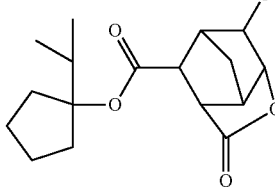
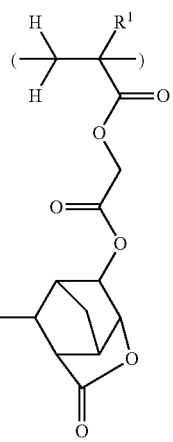
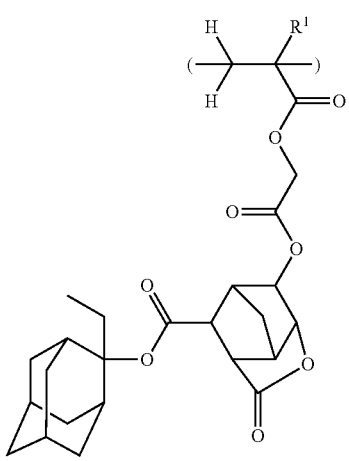

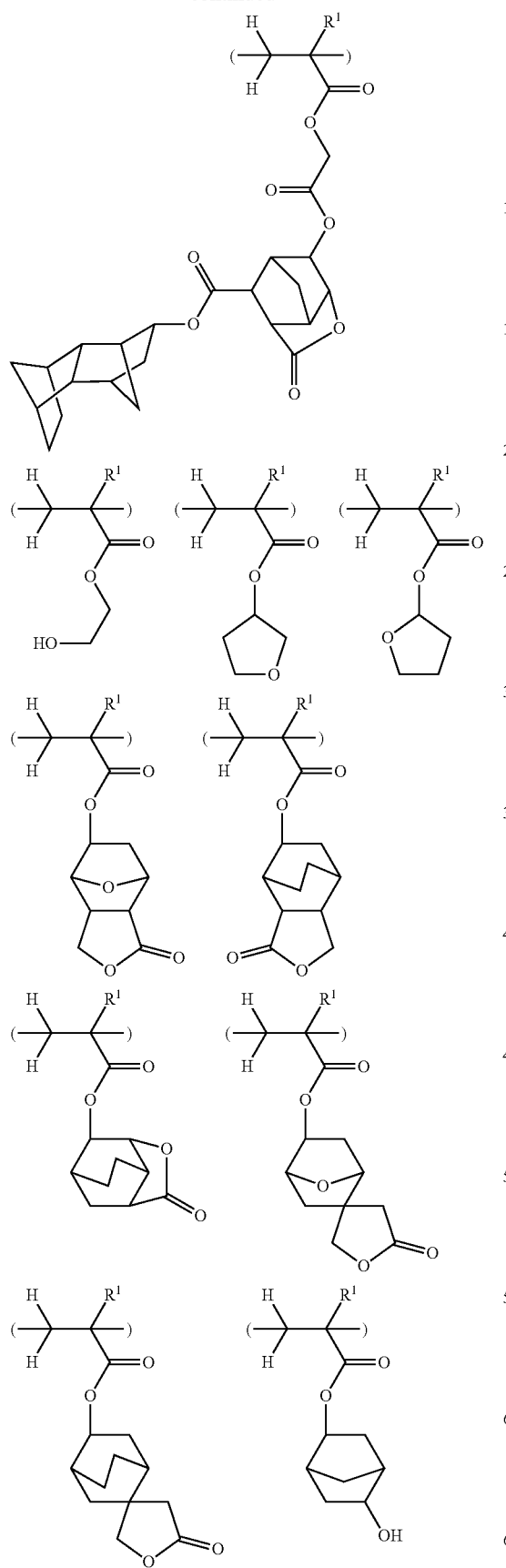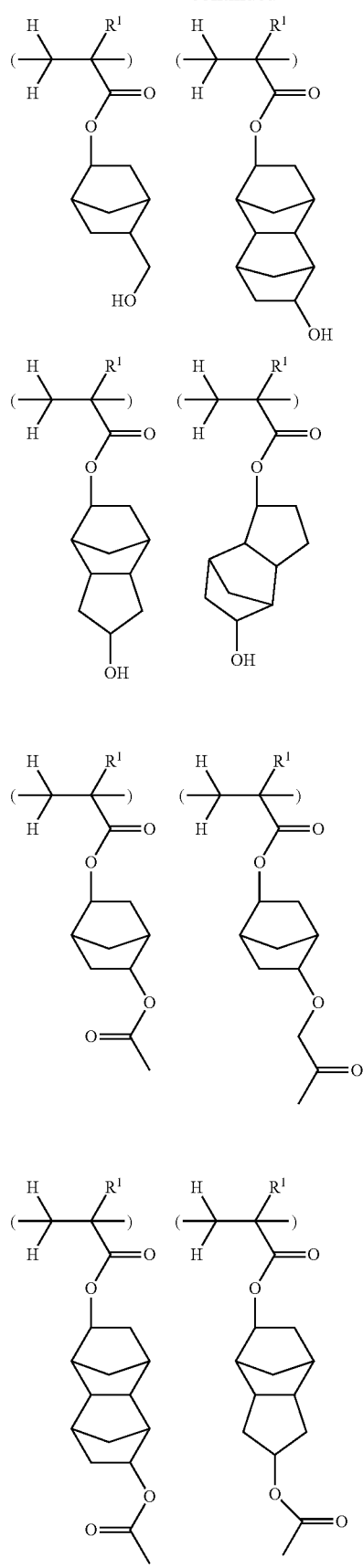

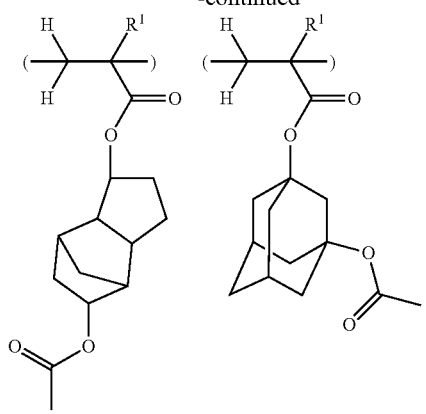
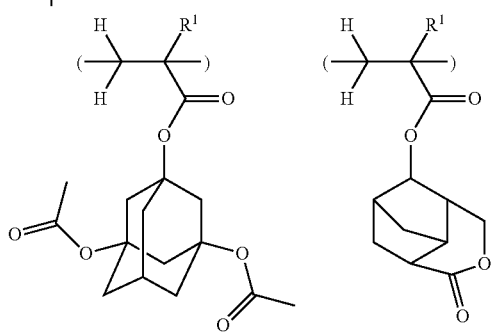
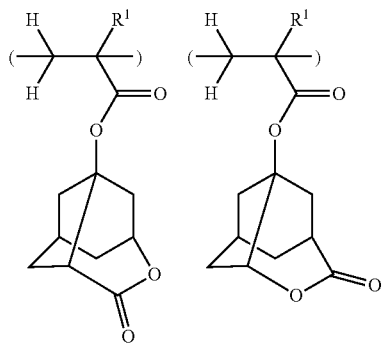
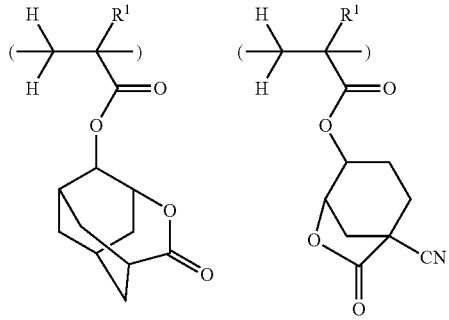
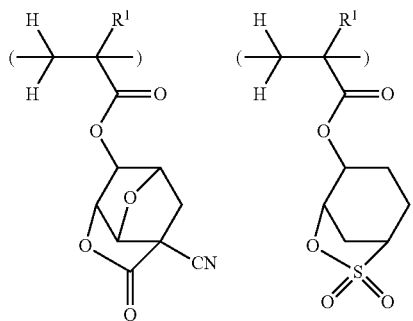
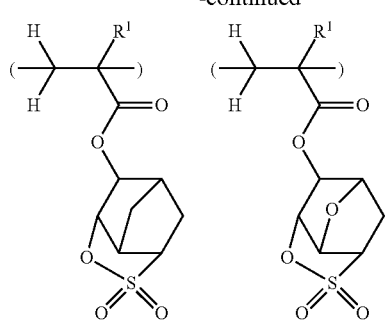
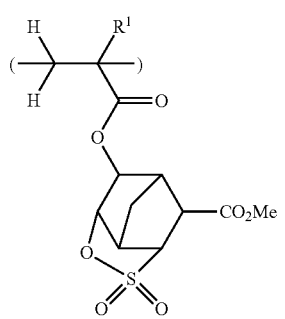
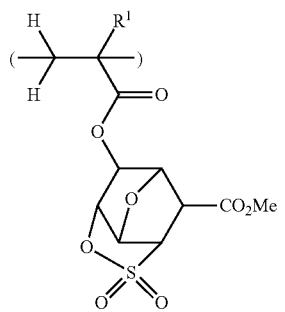
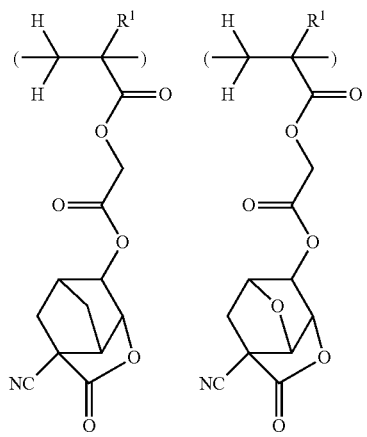

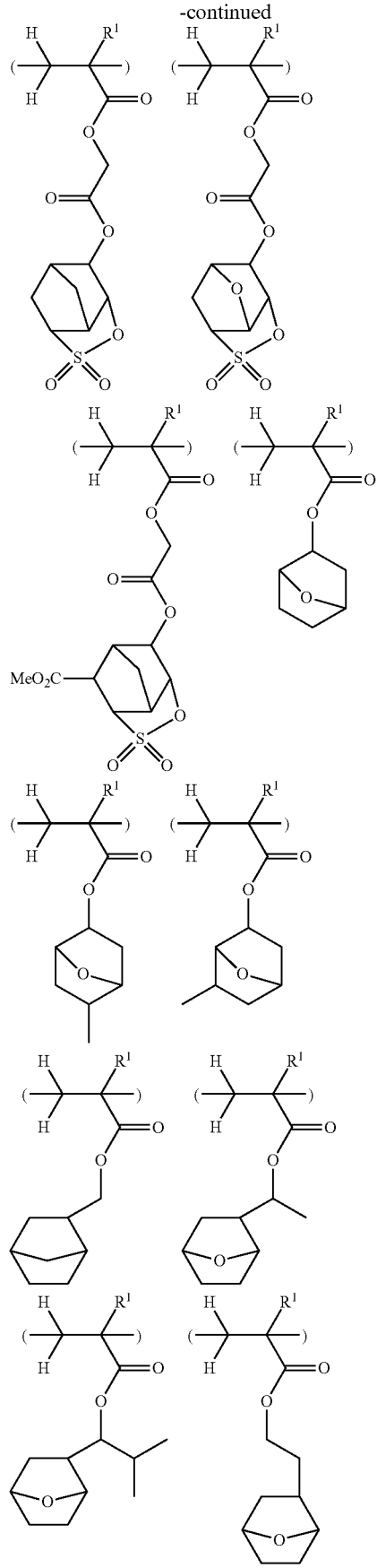
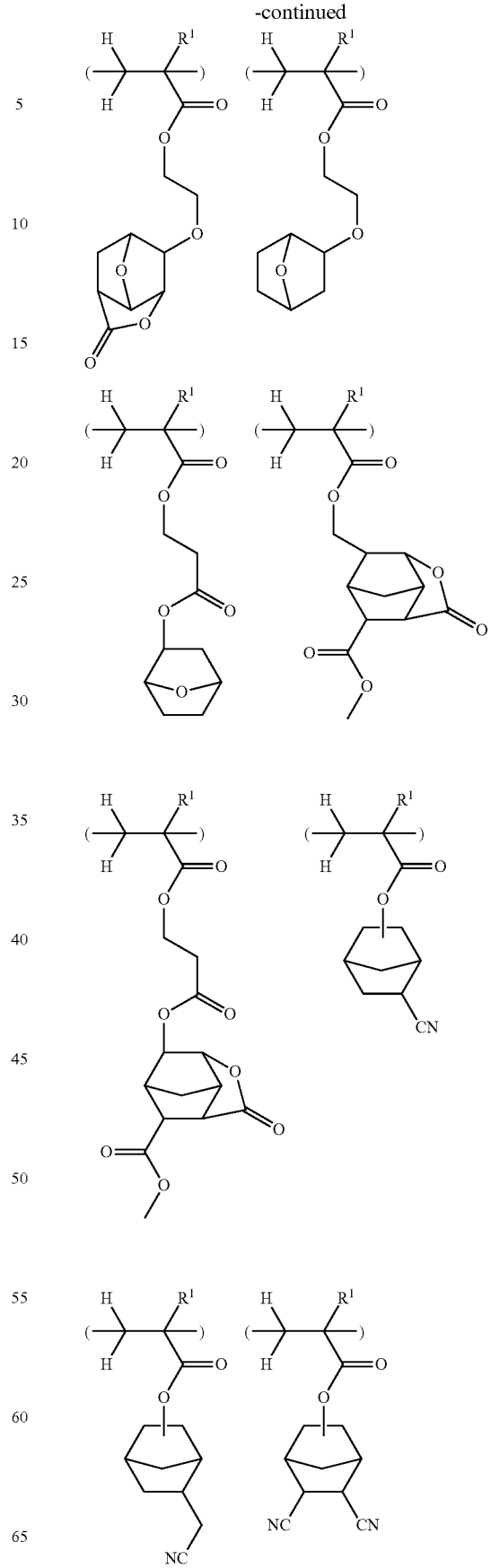

-continued
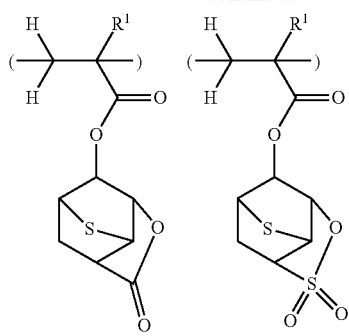
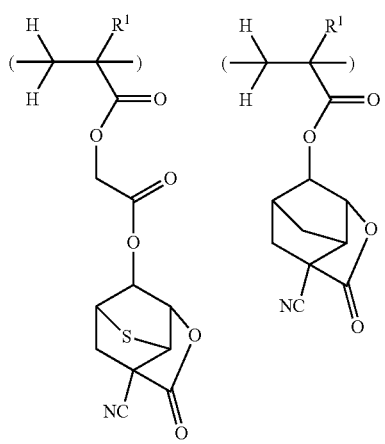
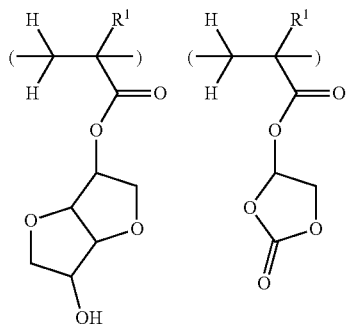
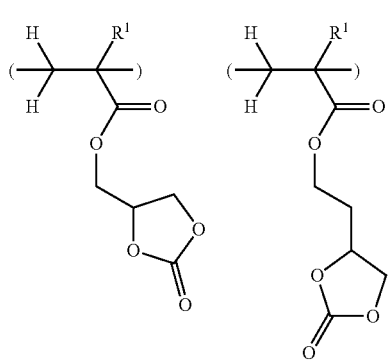
-continued
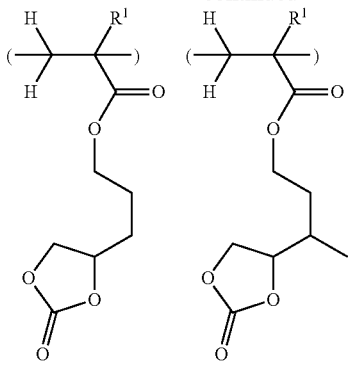
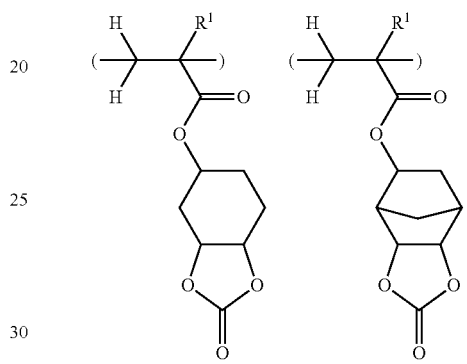
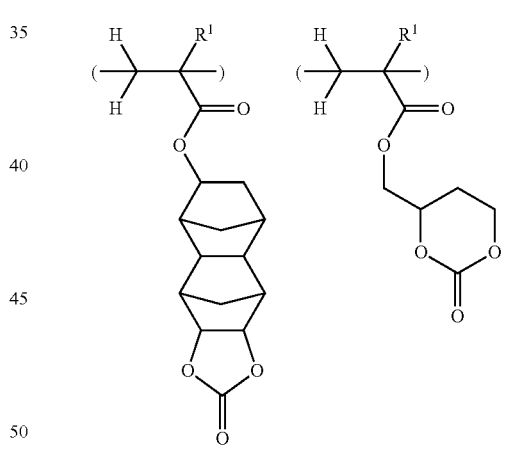
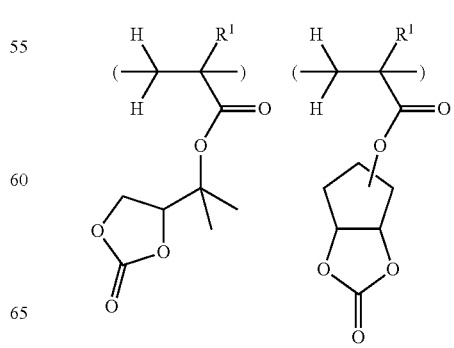

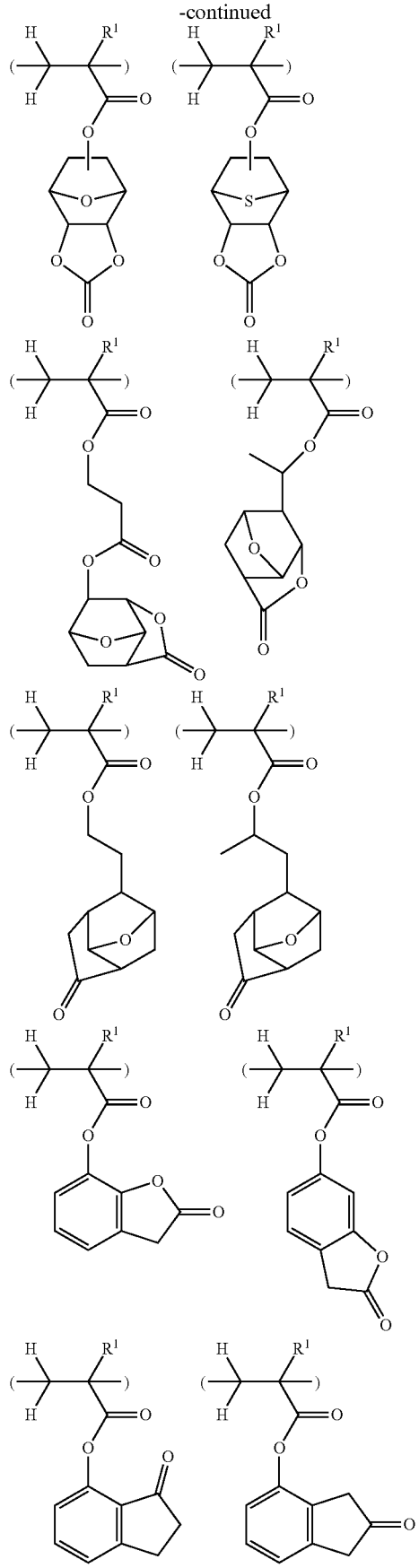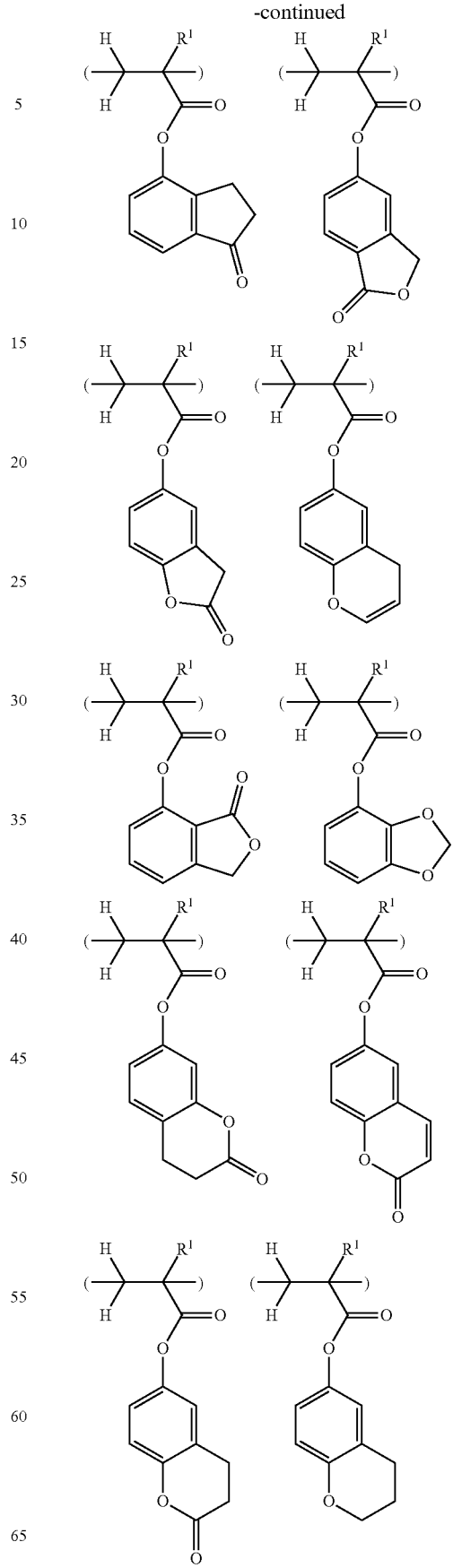

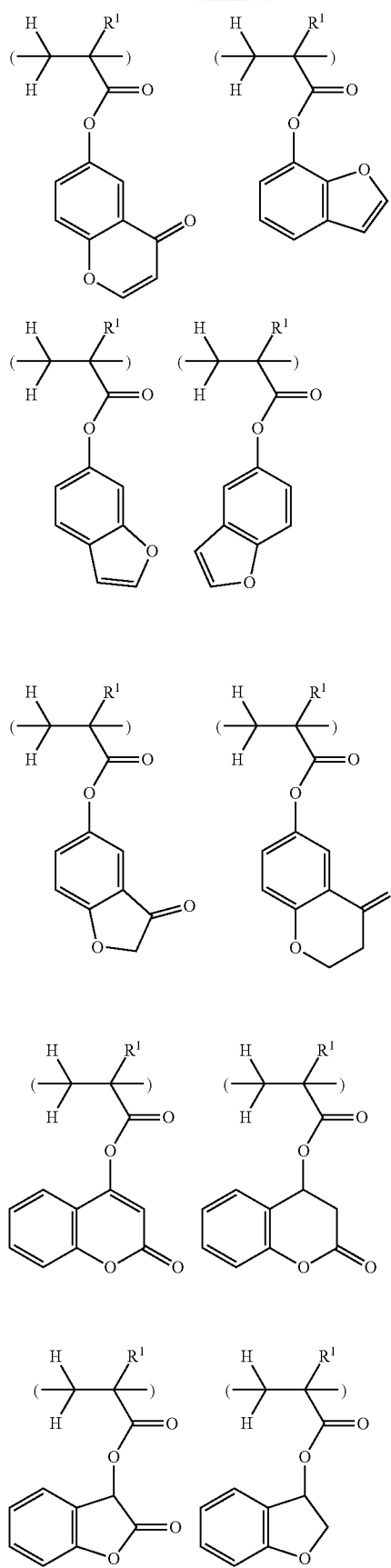
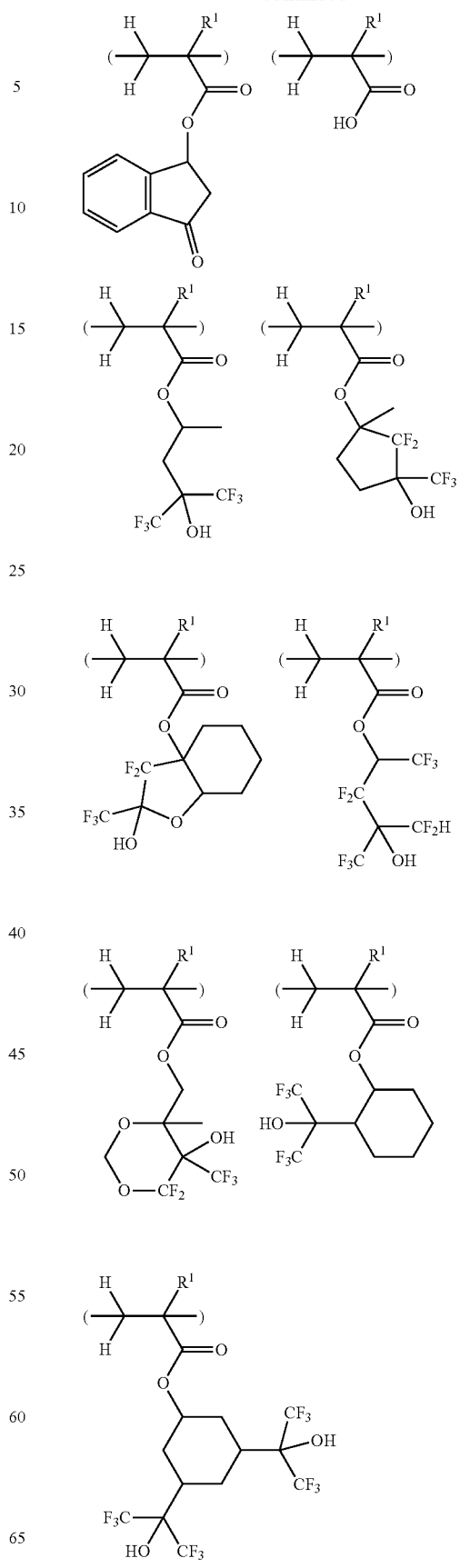

-continued
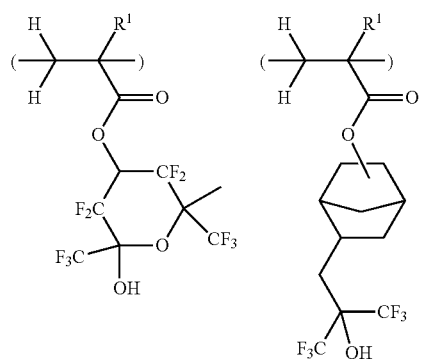
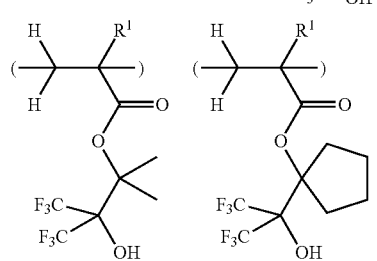
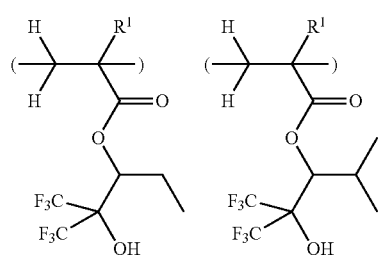
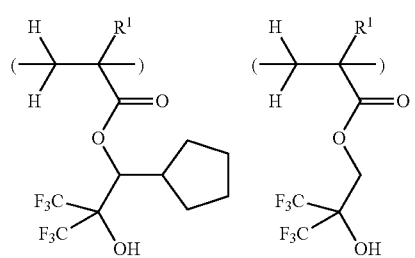
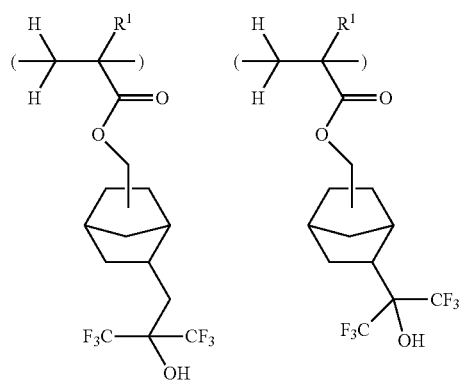
-continued
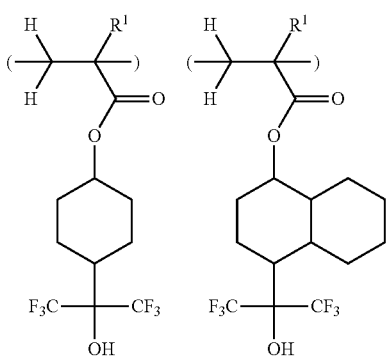
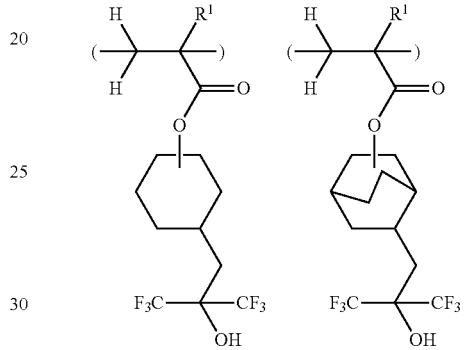
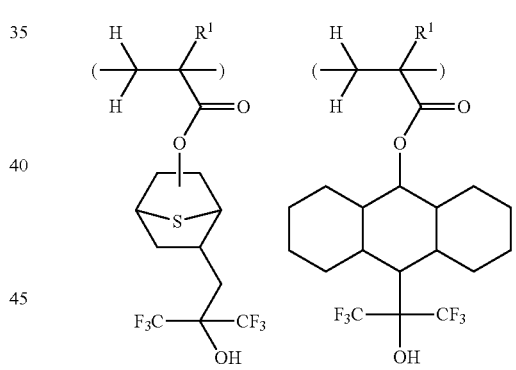
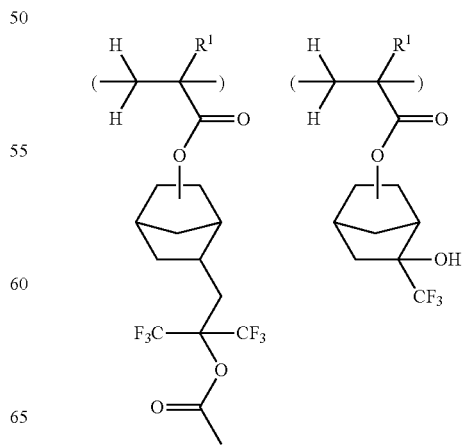

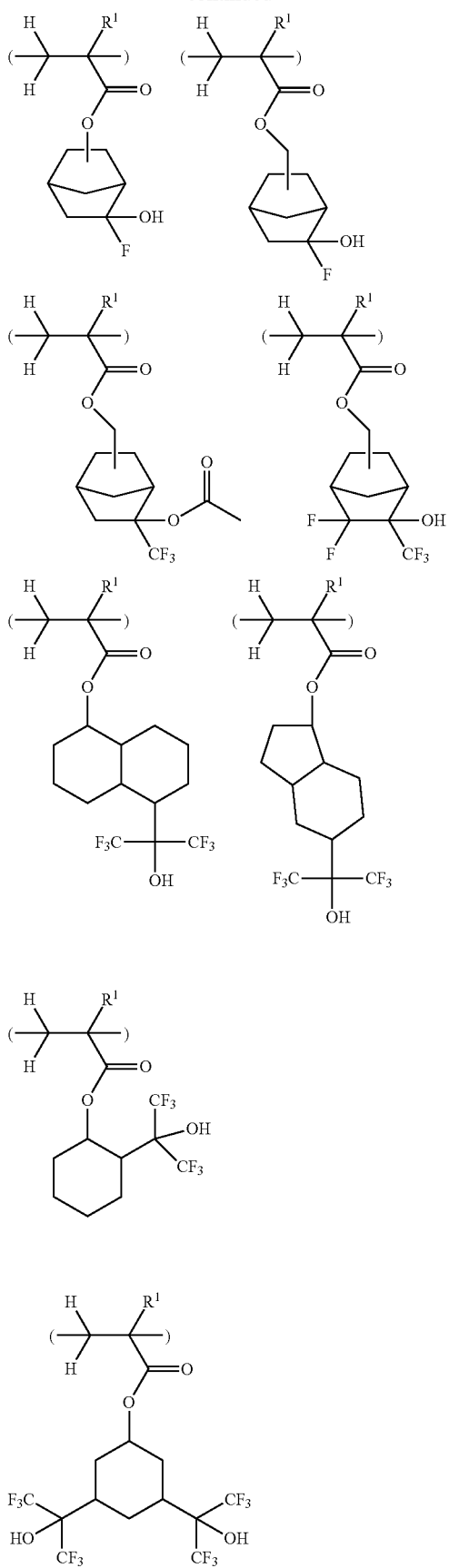
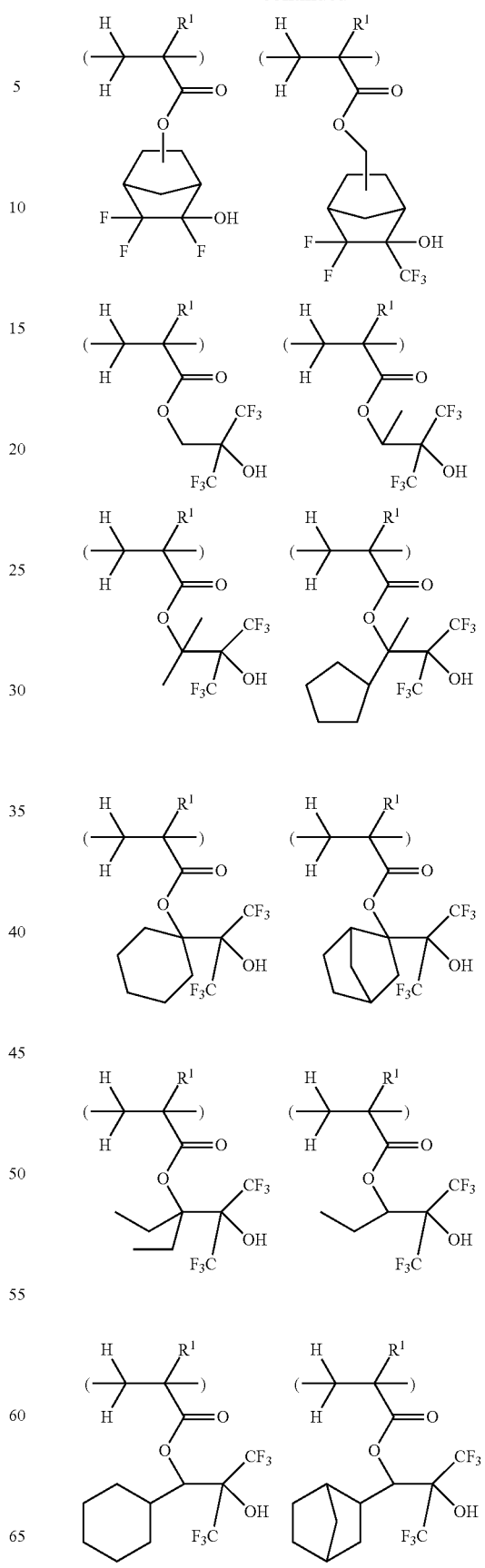

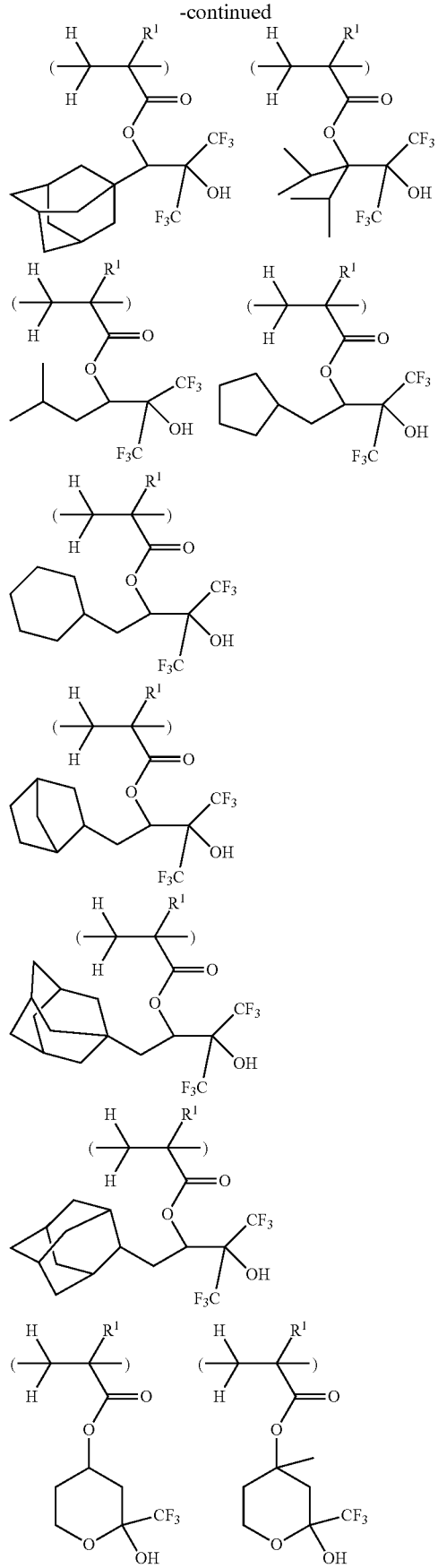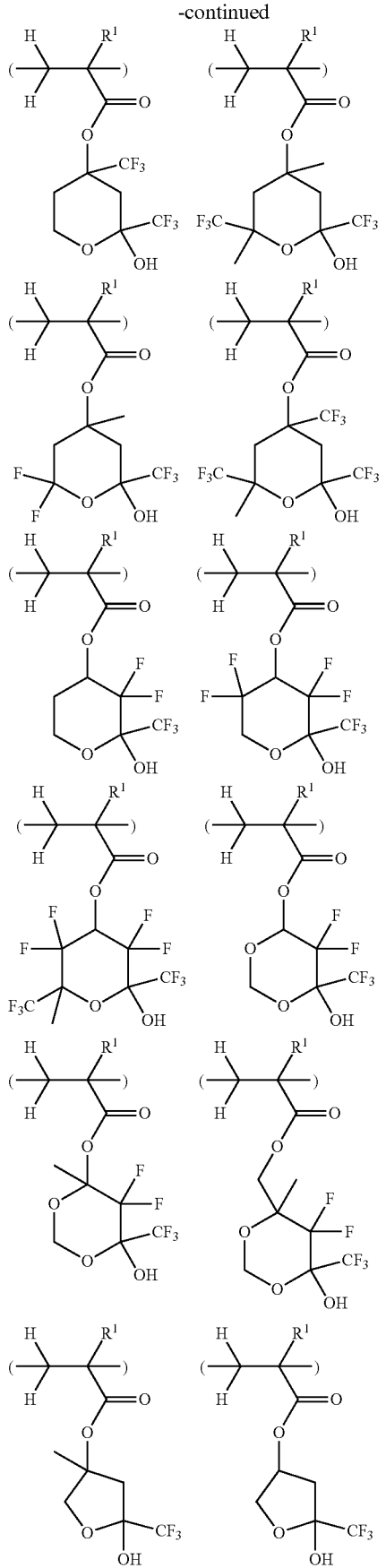

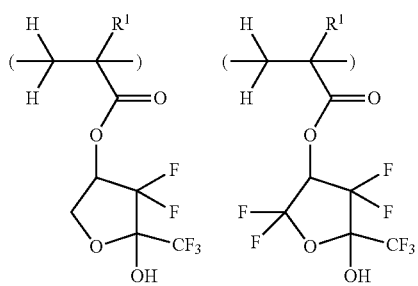
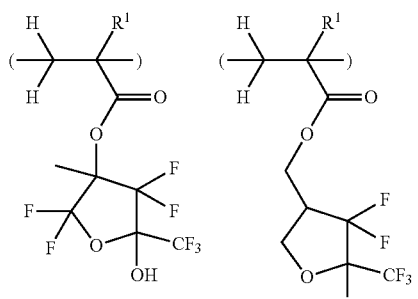
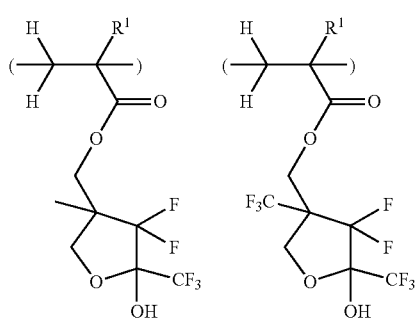
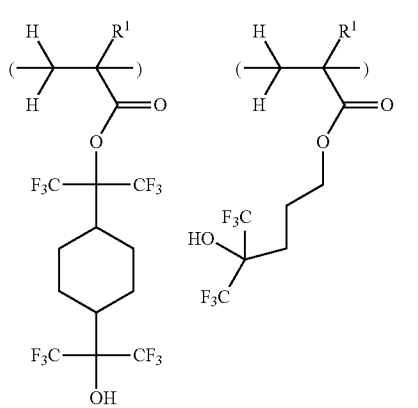
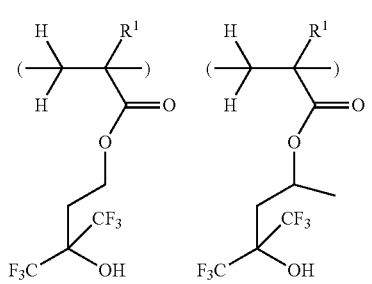
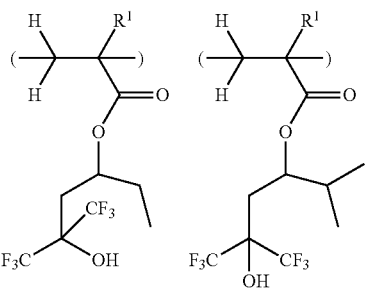
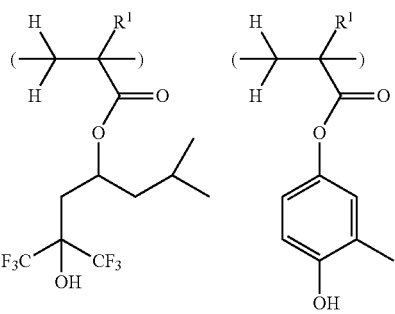
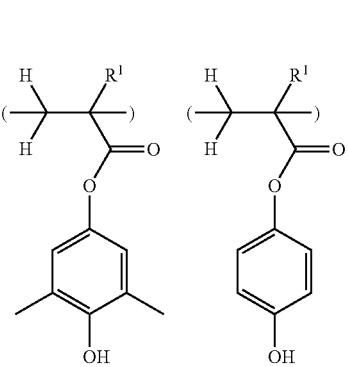
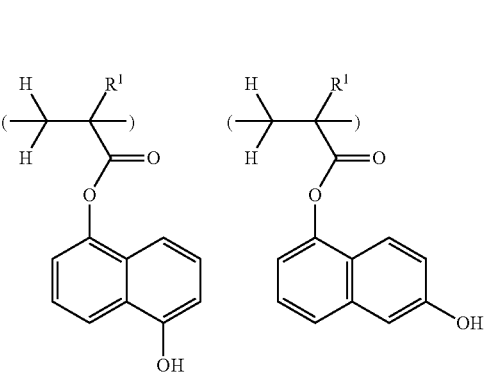
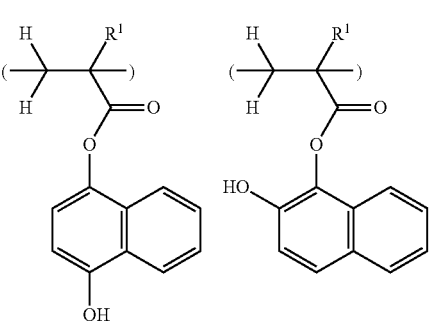

-continued
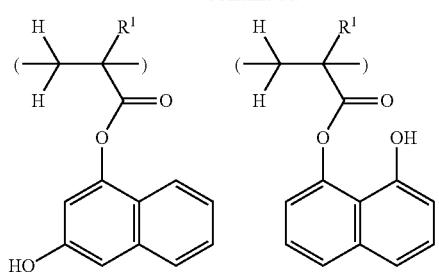
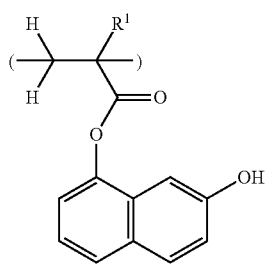
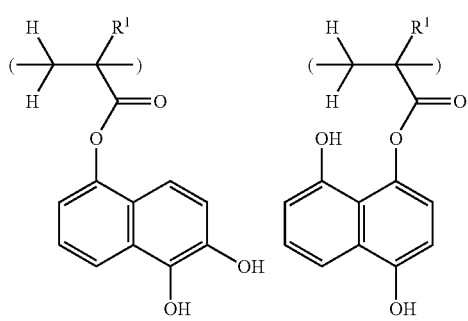
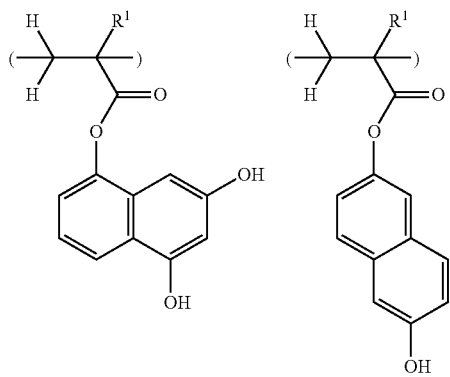
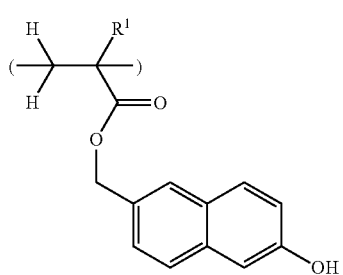
-continued
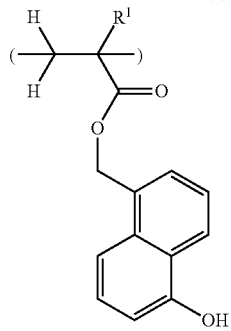
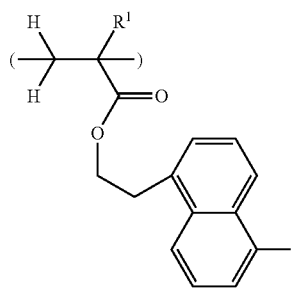
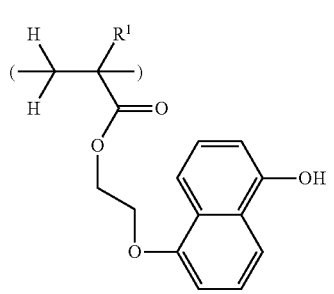
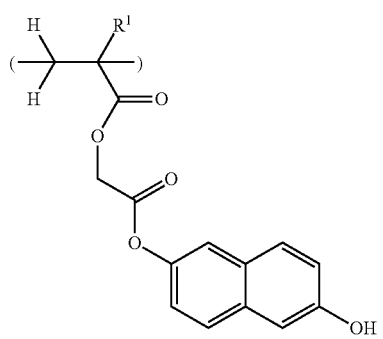
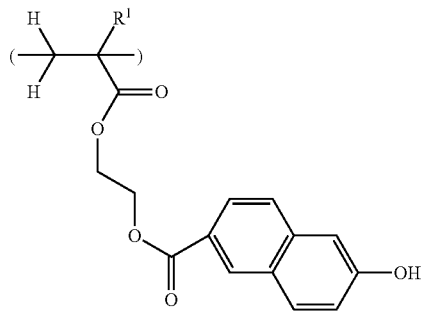

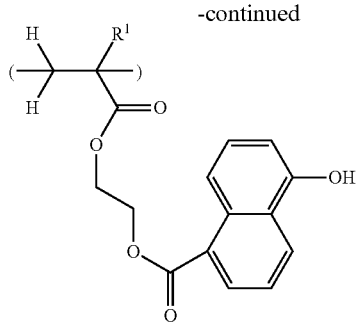

Of the recurring units having formula (7), those units having a lactone ring as the polar group are most preferred.

In addition, Polymer A may further comprise recurring units having the formula (d1), (d2), (d3) or (d4).

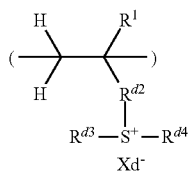 (d1)

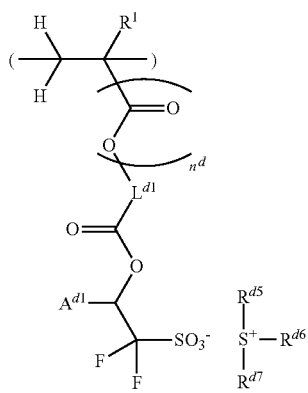 (d2)

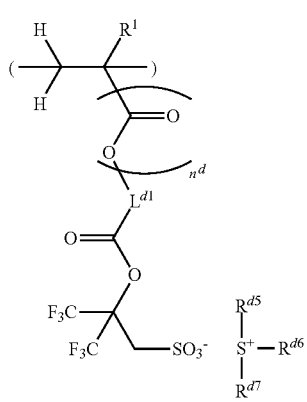 (d3)

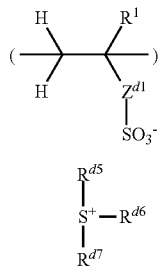 (d4)

In formulae (d1) to (d4), $R^1$ is as defined and exemplified above. $R^{d2}$ is a single bond, phenylene group, —O—$R^{d1}$— or —C(=O)—$Y^{d1}$—$R^{d1}$— wherein $Y^{d1}$ is —O— or —NH—, and Rd is a $C_2$-$C_{20}$ straight, branched or cyclic alkylene group, $C_2$-$C_{20}$ straight, branched or cyclic alkenylene group, or phenylene group, which may contain a heteroatom. $R^{d3}$, $R^{d4}$, $R^{d5}$, $R^{d6}$ and $R^{d7}$ are each independently a $C_1$-$C_{20}$ straight, branched or cyclic monovalent hydrocarbon group which may contain a heteroatom. Any two of $R^{d2}$, $R^{d3}$ and $R^{d4}$ may bond together to form a ring with the sulfur atom to which they are attached, and any two of $R^{d5}$, $R^{d6}$ and $R^{d4}$ may bond together to form a ring with the sulfur atom to which they are attached. $Xd^-$ is a non-nucleophilic counter ion. $A^{d1}$ is hydrogen or trifluoromethyl. $L^{d1}$ is a single bond or a $C_1$-$C_{20}$ straight, branched or cyclic divalent hydrocarbon group which may contain a heteroatom. The subscript $n^4$ is 0 or 1, and $n^d$ is 0 when $L^d$ is a single bond. $Z^{d1}$ is a single bond, methylene, ethylene, phenylene, fluorophenylene, —O—O—$R^{d1}$—, or —C(=O)—$Y^{d1}$—$R^{d1}$—.

Examples of the non-nucleophilic counter ion represented by $Xd^-$ in formula (d1) include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imides such as bis(trifluoromethylsulfonyl)imide, bis(perfluoroethylsulfonyl)imide, and bis(perfluorobutylsulfonyl)imide; and methides such as tris(trifluoromethylsulfonyl)methide and tris(perfluoroethylsulfonyl)methide.

Other non-nucleophilic counter ions include anions having the formulae (d5) and (d6).

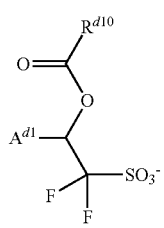 (d5)

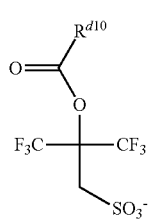 (d6)

In formulae (d5) and (d6), $A^{d1}$ is as defined above, and $R^{d10}$ is a $C_1$-$C_{20}$ straight, branched or cyclic monovalent hydrocarbon group which may contain a heteroatom.

The anion moiety of formula (d5) is exemplified by those structures illustrated in JP-A 2010-113209 and JP-A 2007-145797. The anion moiety of formula (d6) is exemplified by those structures illustrated in JP-A 2010-215608.

The anion moiety in formula (d2) wherein $A^{d1}$ is hydrogen is exemplified by those structures illustrated in JP-A 2010-116550. The anion moiety in formula (d2) wherein $A^{d1}$ is trifluoromethyl is exemplified by those structures illustrated in JP-A 2010-077404.

Exemplary structures of the anion moiety in formula (d3) correspond to the exemplary structures of formula (d2) wherein $-CH(A^{d1})CF_2SO_3^-$ is replaced by $-C(CF_3)_2CH_2SO_3^-$.

Illustrative examples of the sulfonium cation in formulae (d2) to (d4) are the same as the above-exemplified sulfonium cations.

Polymer A may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units having the formula (e) are preferred.

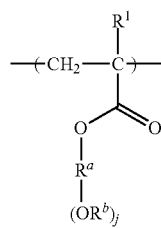

(e)

In formula (e), $R^1$ is as defined above, $R^a$ is a $C_1$-$C_{30}$ straight, branched or cyclic, di- to pentavalent hydrocarbon group which may contain a heteroatom, $R^b$ is an acid labile group, and j is an integer of 1 to 4.

Examples of the recurring unit of formula (e) are shown below, but not limited thereto. Herein $R^1$ and $R^b$ are as defined above.

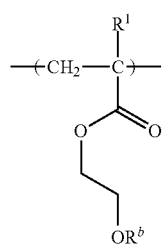

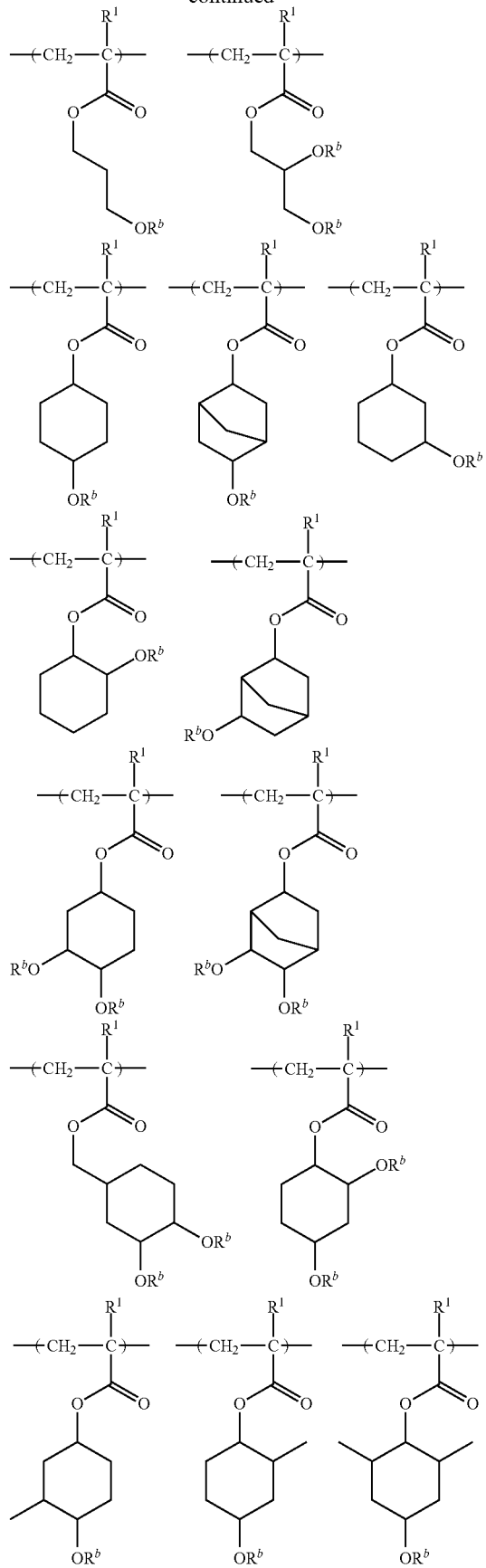

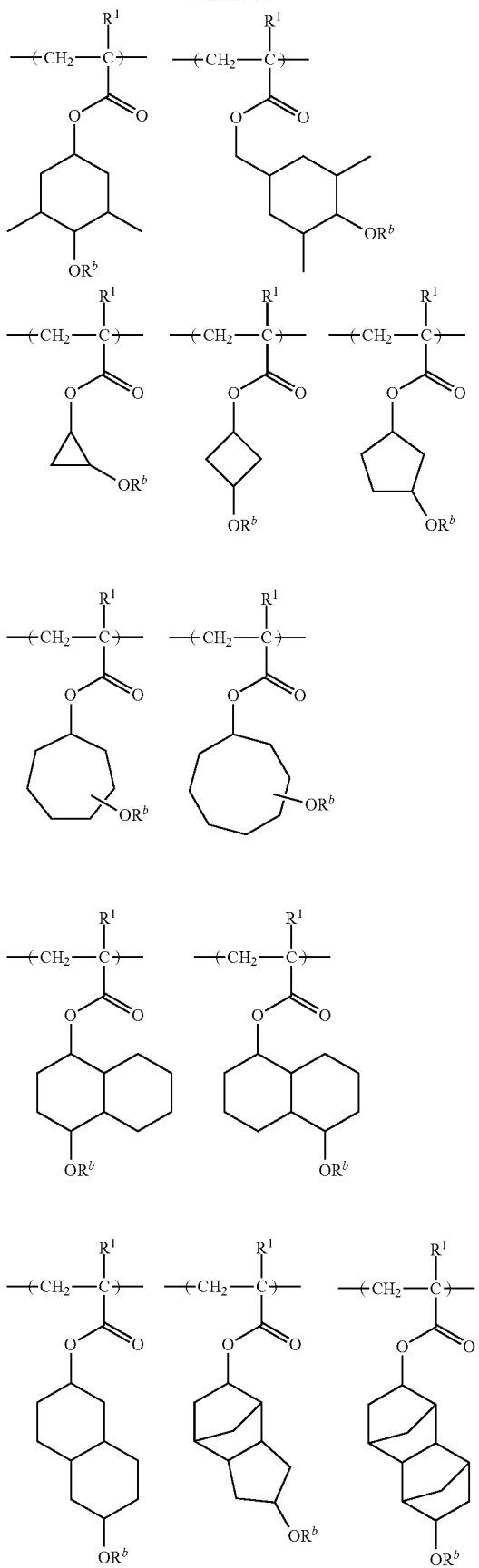
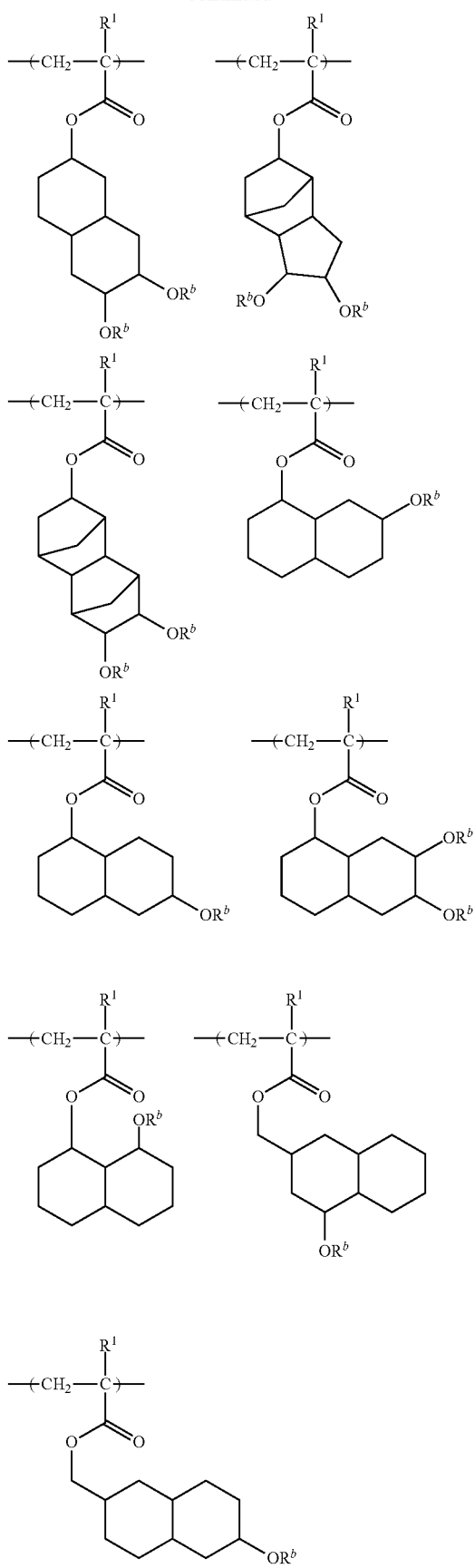

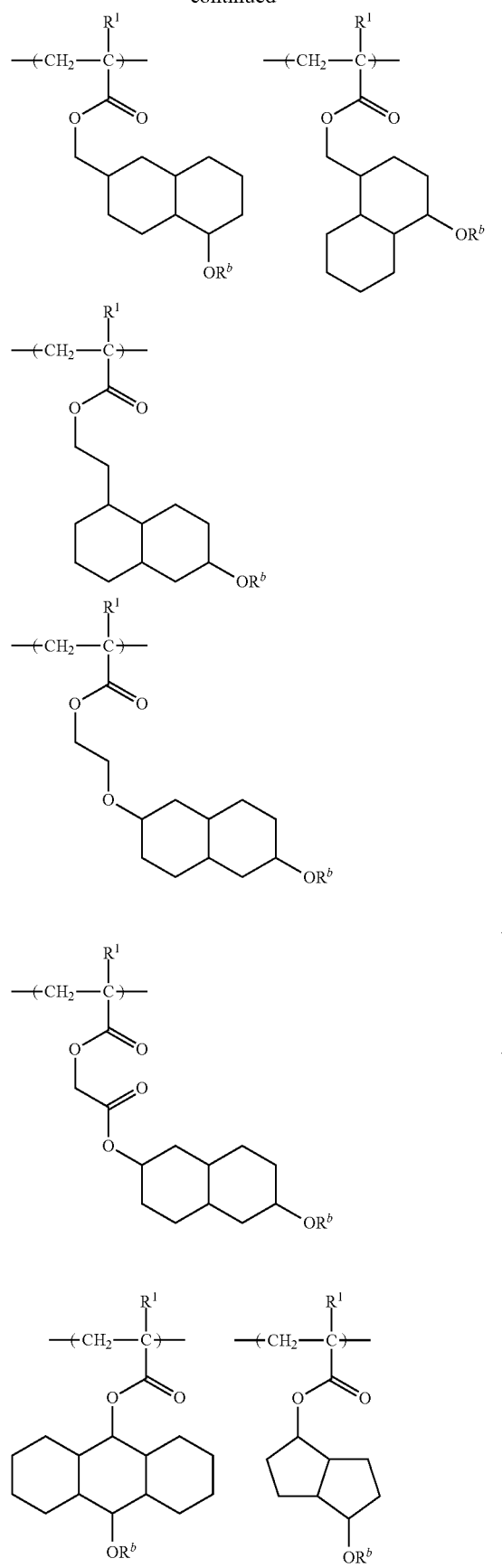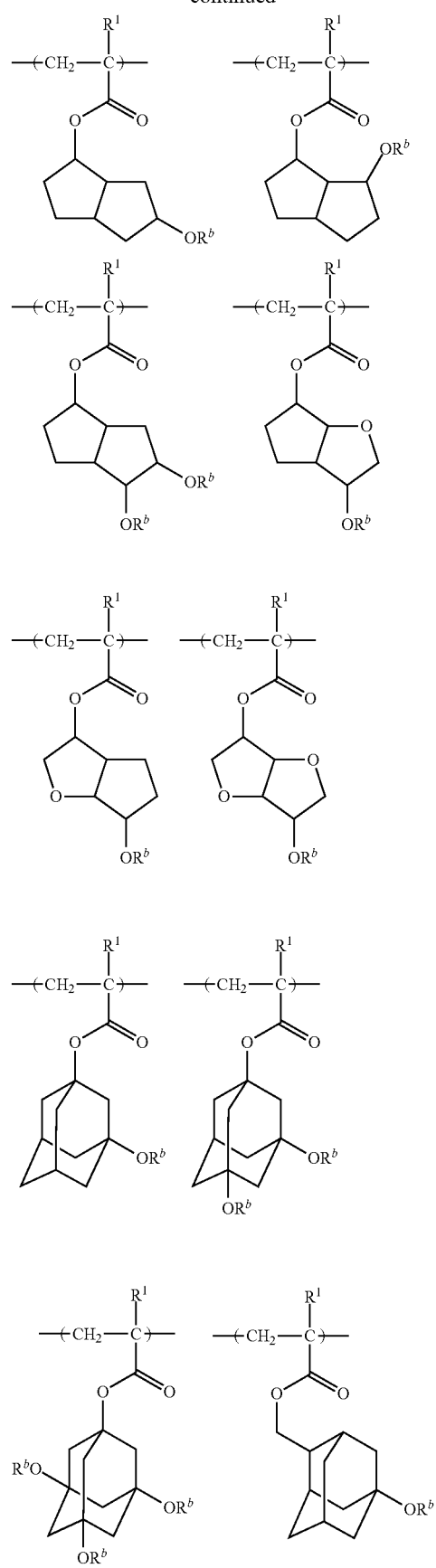

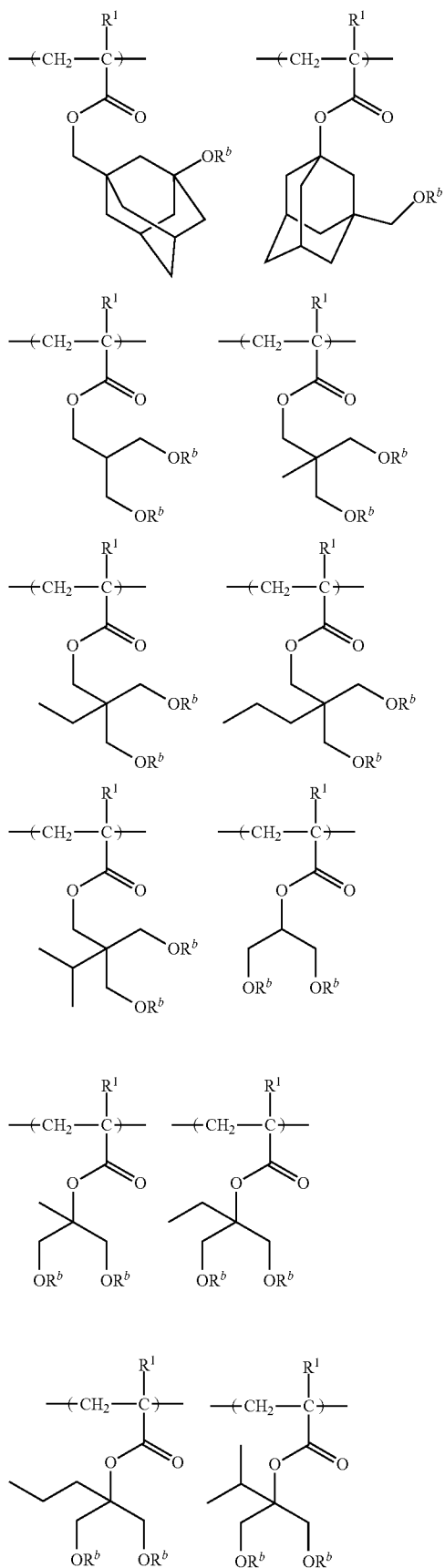
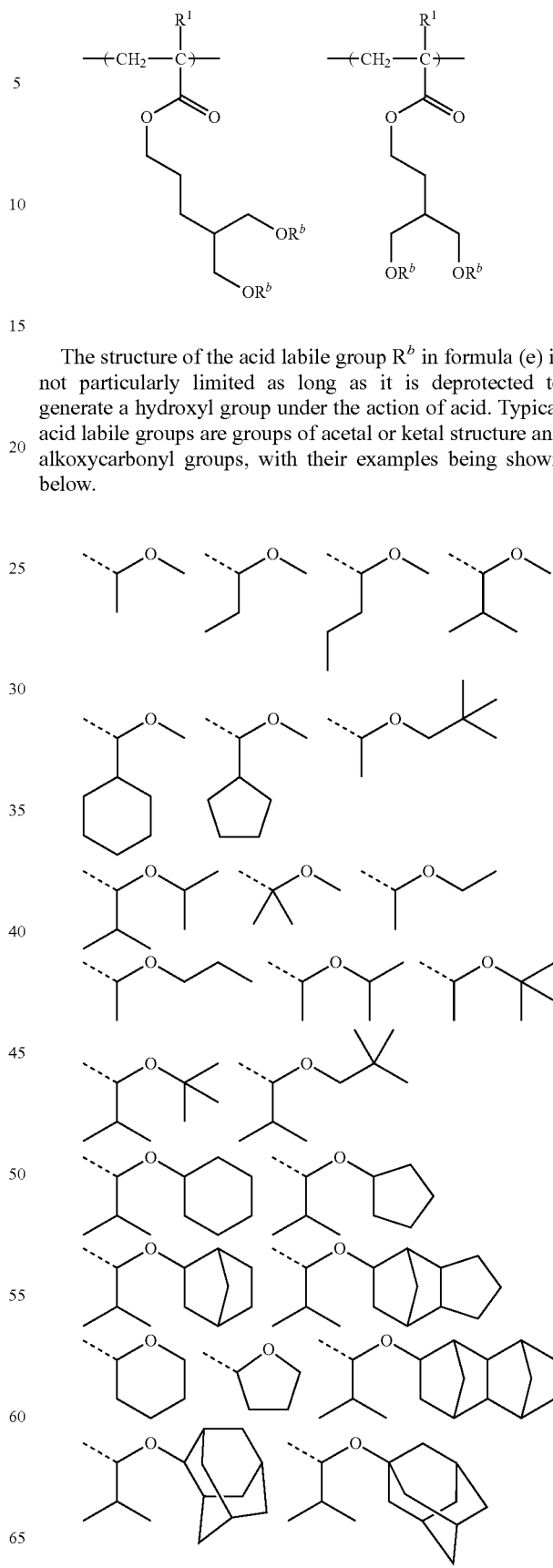
The structure of the acid labile group $R^b$ in formula (e) is not particularly limited as long as it is deprotected to generate a hydroxyl group under the action of acid. Typical acid labile groups are groups of acetal or ketal structure and alkoxycarbonyl groups, with their examples being shown below.

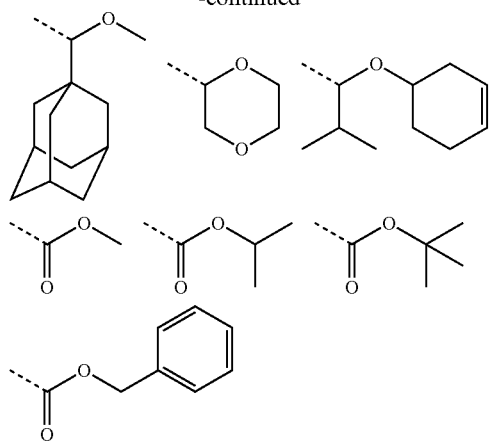
Of the acid labile group R$^b$, preferred are alkoxymethyl groups having the formula (e1):
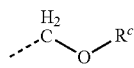 (e1)
wherein R$^c$ is a C$_1$-C$_{20}$ straight, branched or cyclic monovalent hydrocarbon group such as alkyl.
Examples of the acid labile group of formula (e1) are shown below, but not limited thereto.
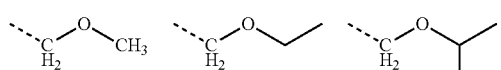
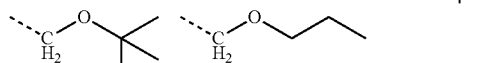
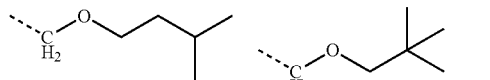
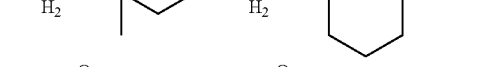
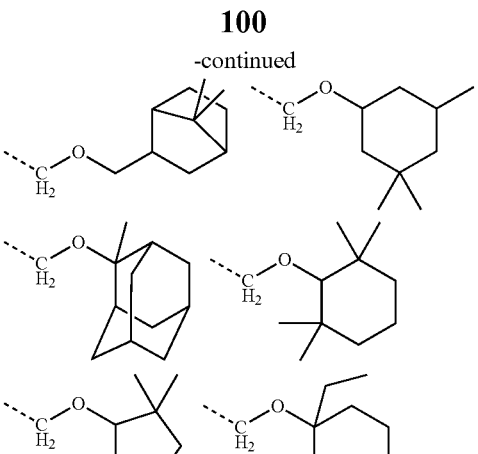
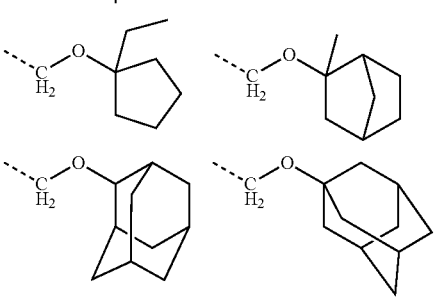
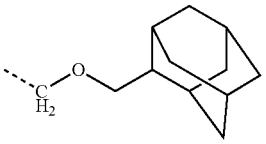
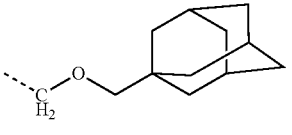
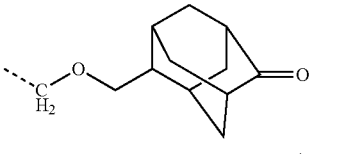
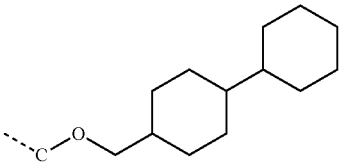
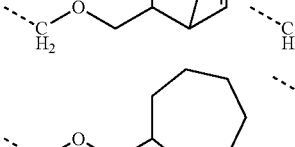
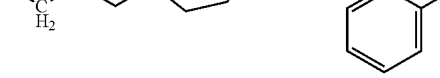

101
-continued
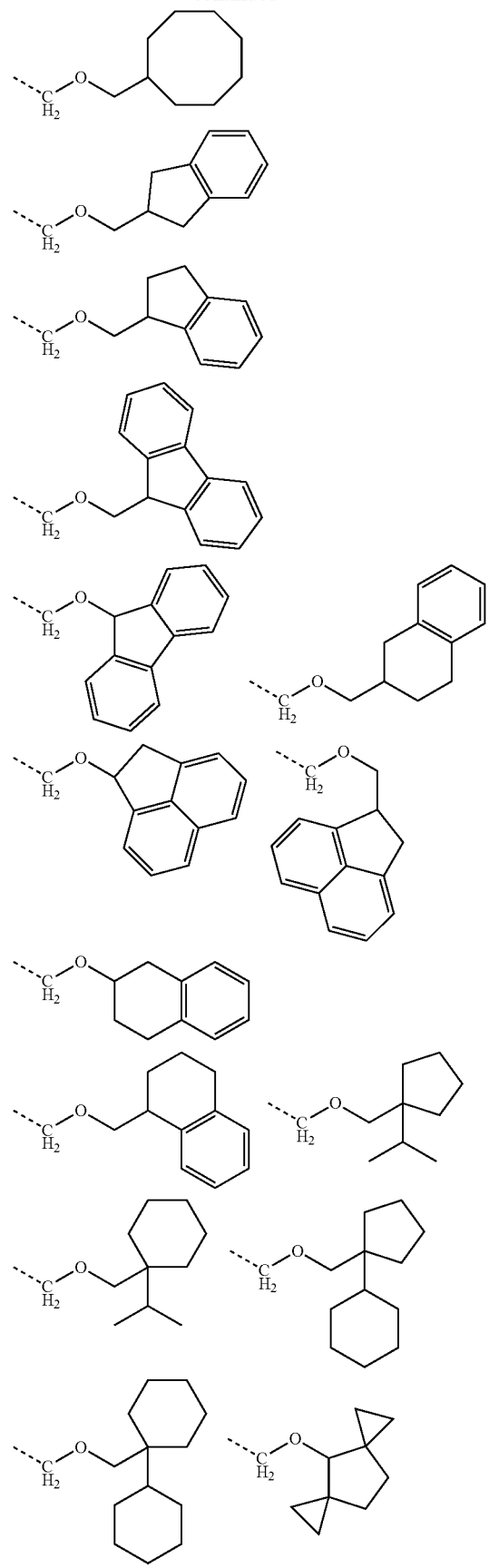
102
-continued
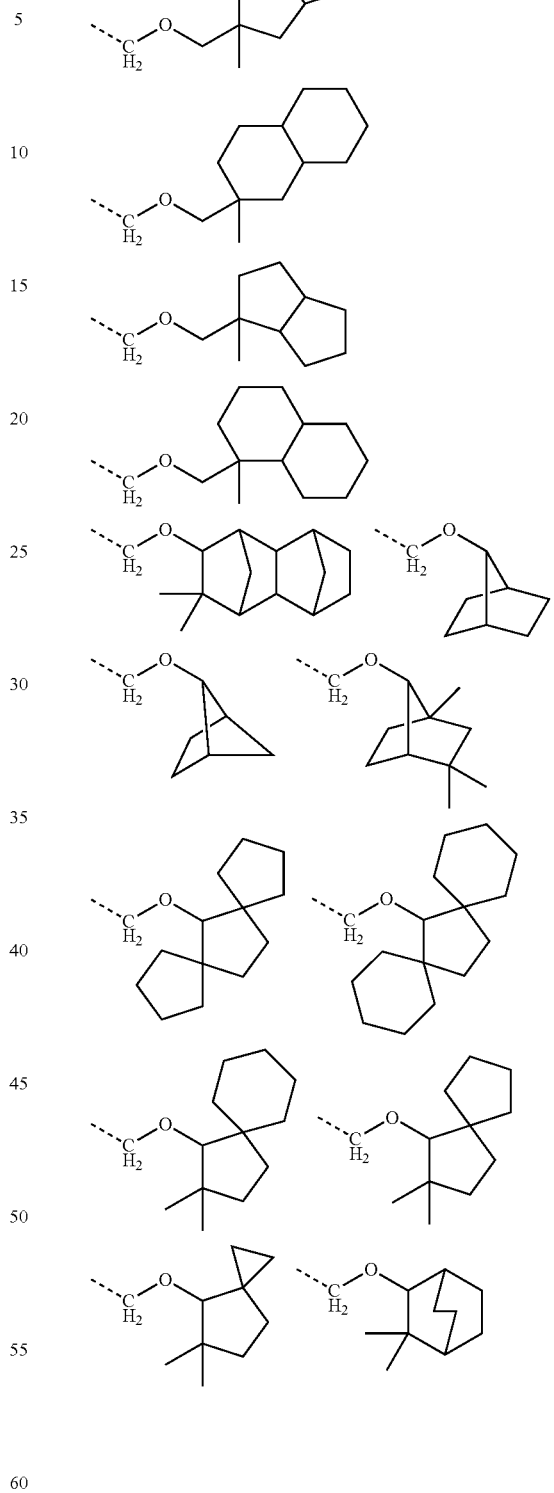
Besides the aforementioned structures, a monomer having a plurality of hydroxyl groups which are acetal-protected with a carbonyl compound as shown below is also exemplary of the monomer providing the recurring unit having a hydroxyl group protected with an acid labile group. Herein $R^1$ is as defined above.

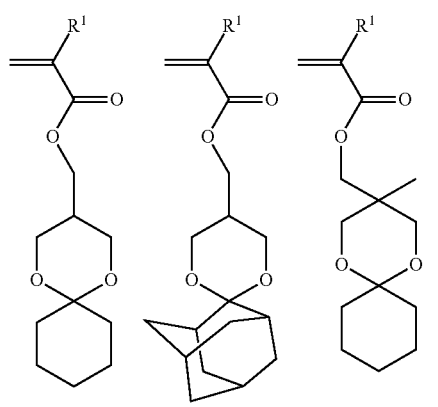
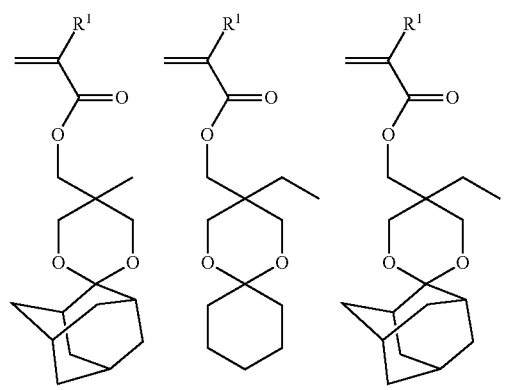
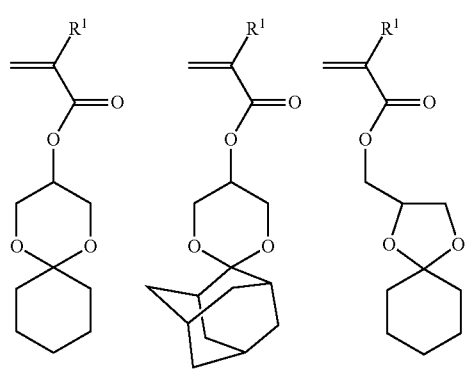
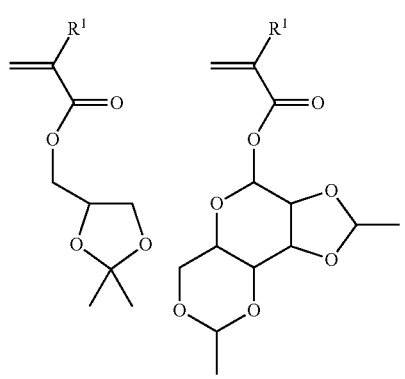
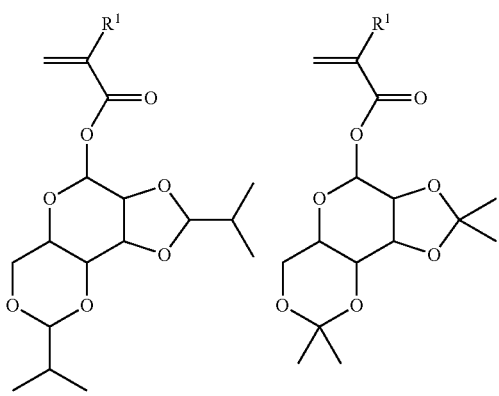
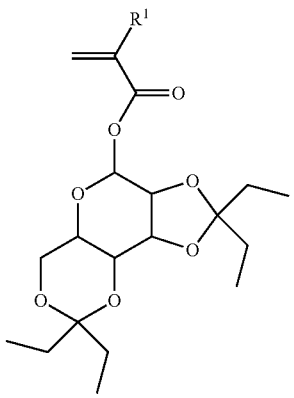
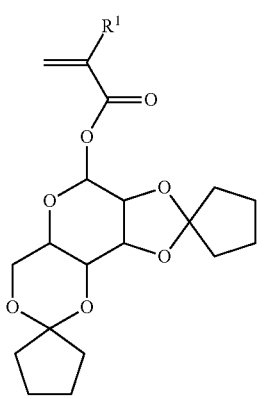
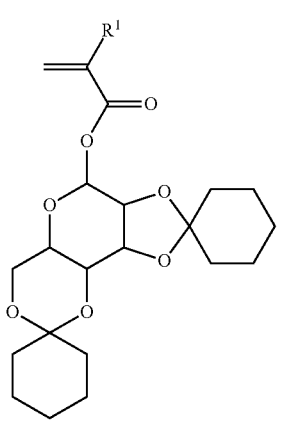
-continued

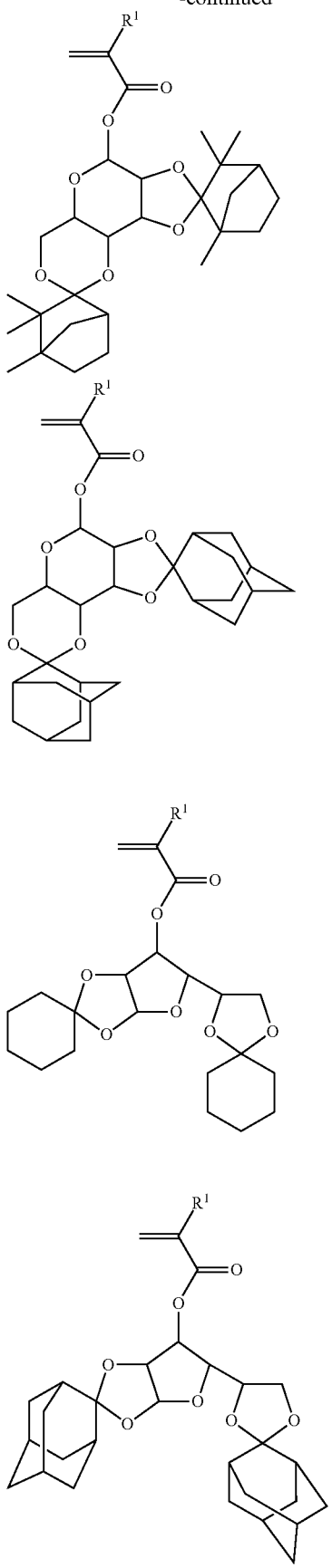

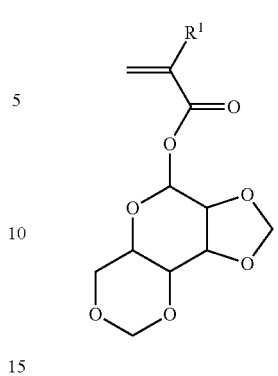

In addition to the foregoing units, Polymer A may further comprise recurring units having an oxetane ring or oxirane ring. Copolymerization of oxetane or oxirane ring-containing units ensures that the resist film is crosslinked in the exposed region. The exposed region of resist film is thus improved in retention and etch resistance.

Examples of the monomer providing the recurring unit having an oxetane ring or oxirane ring are shown below, but not limited thereto. Herein $R^1$ is as defined above.

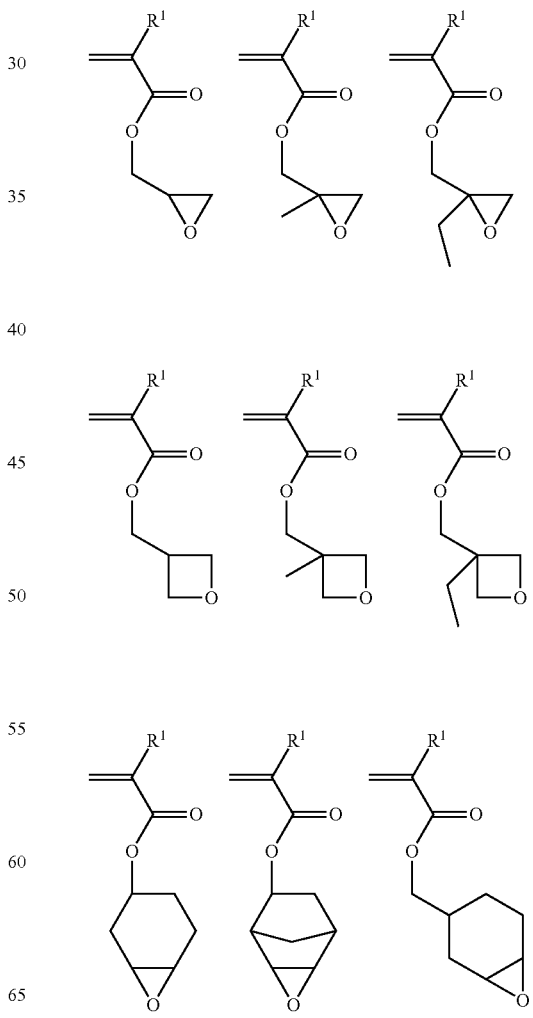

-continued
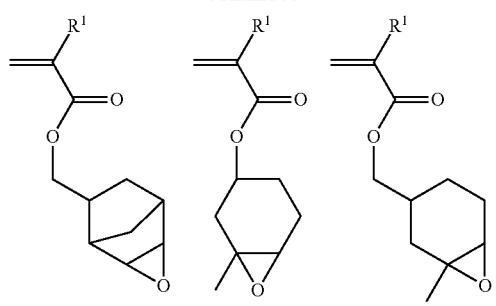
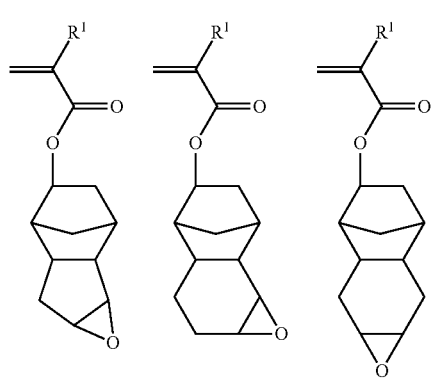
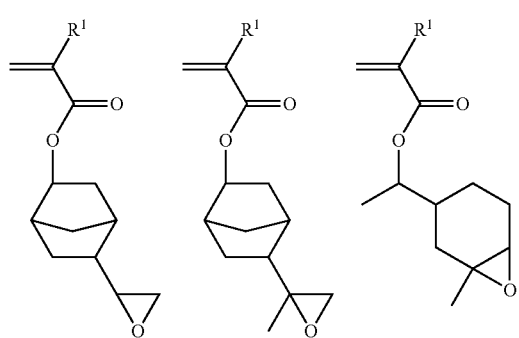
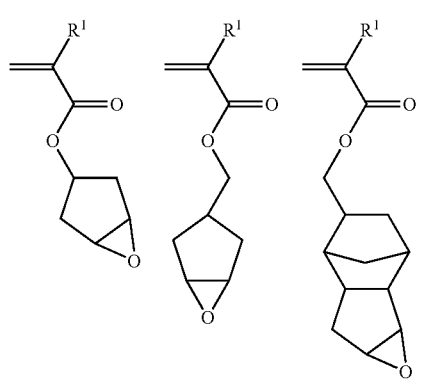
-continued
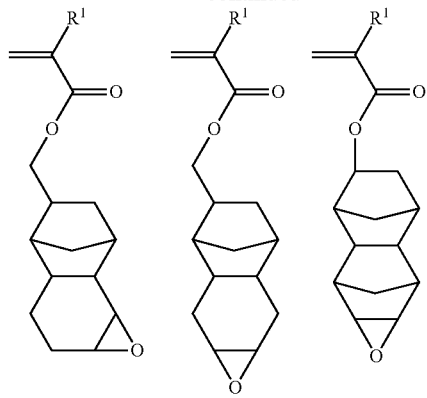
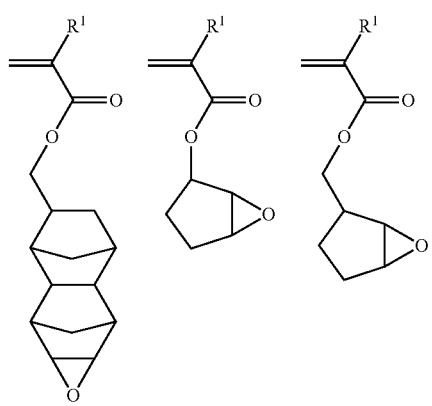
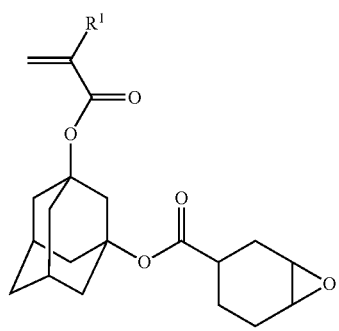

109
-continued
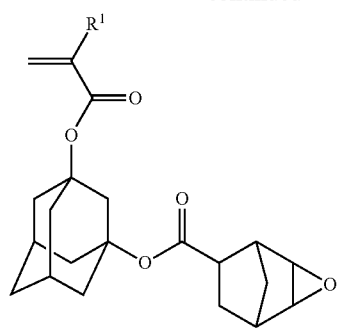
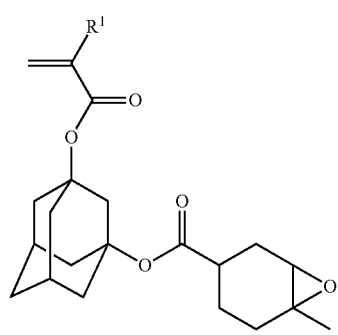
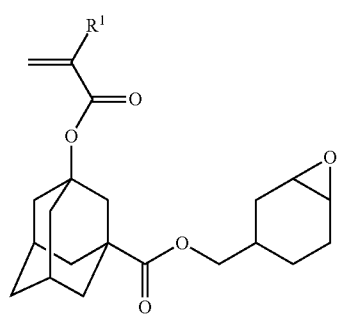
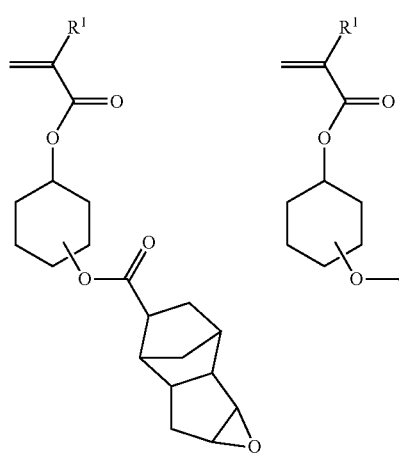
110
-continued
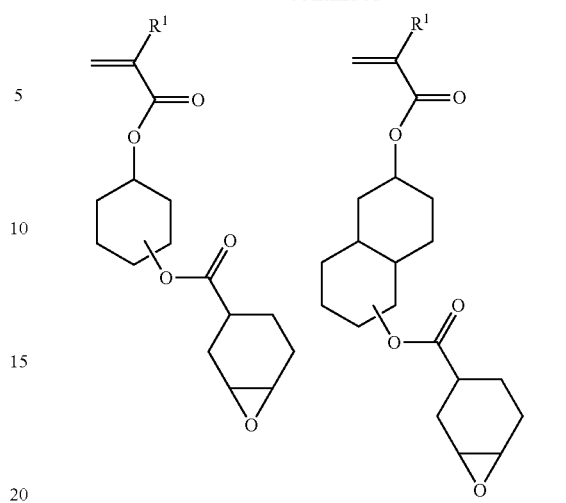
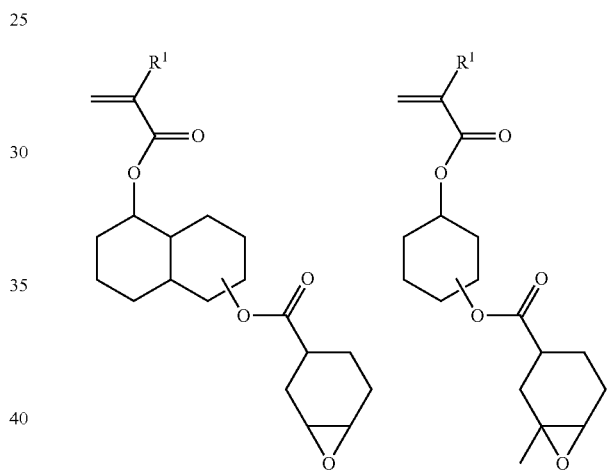
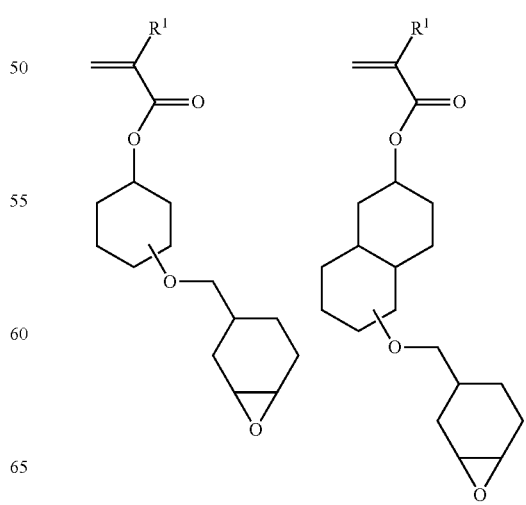

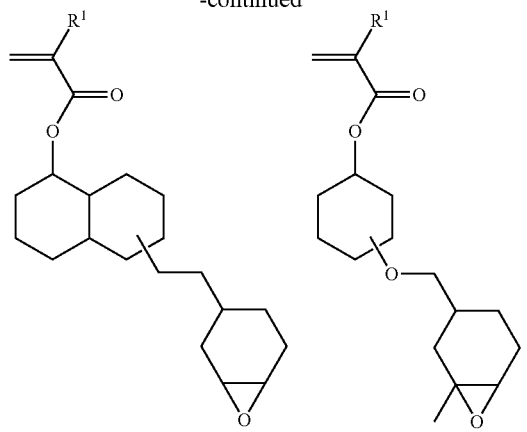
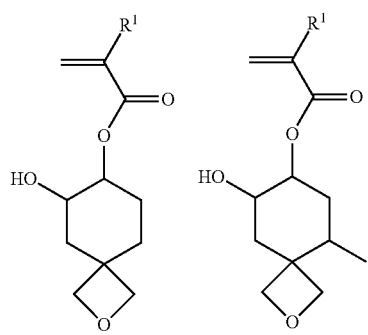
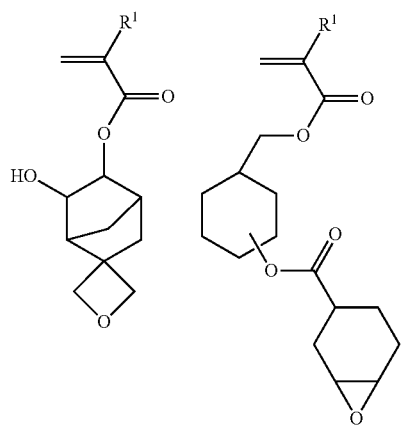
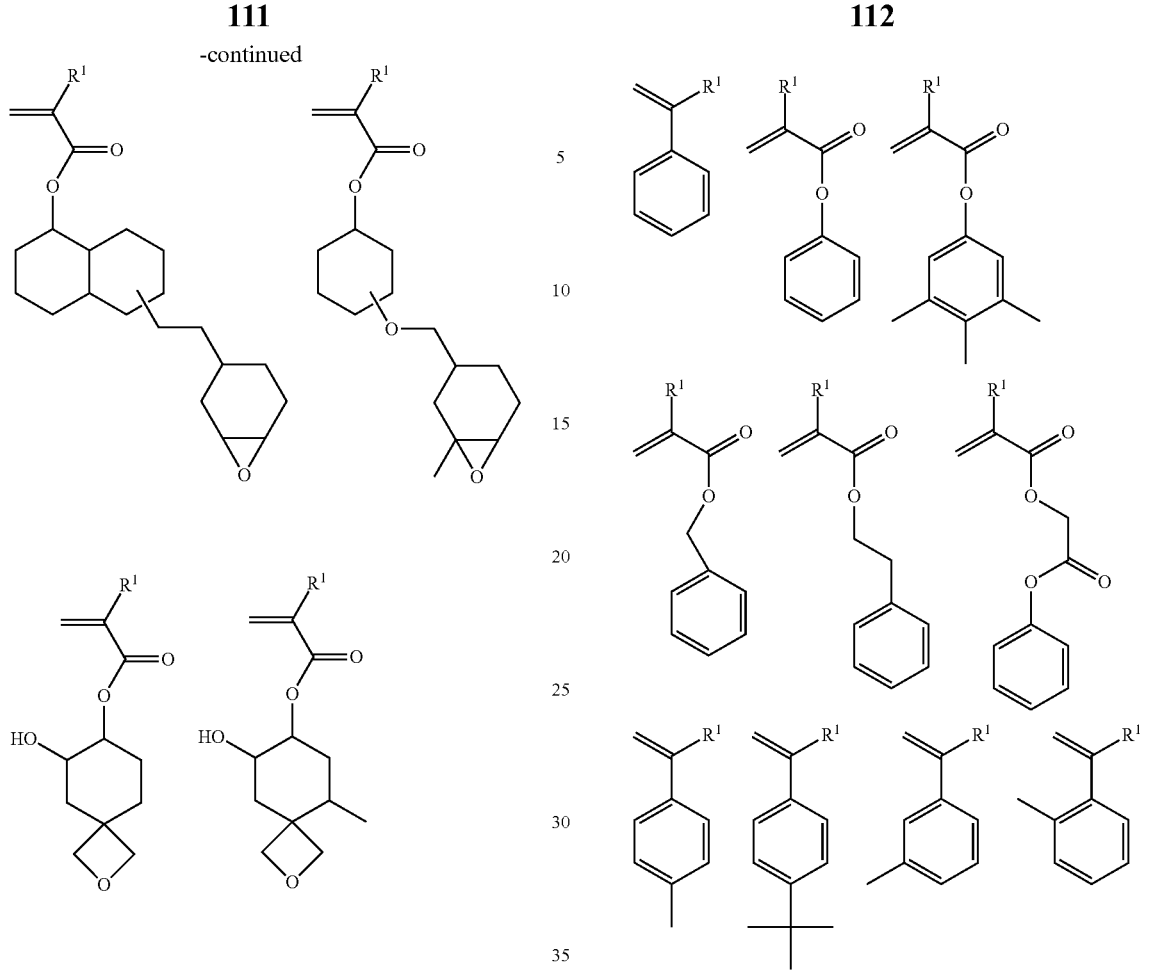
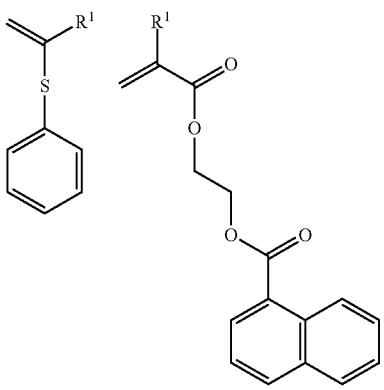

In addition to the foregoing units, Polymer A may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers. Also, hydrogenated ROMP polymers as described in JP-A 2003-066612 may be used.

The other monomers are exemplified below, but not limited thereto.

113
-continued
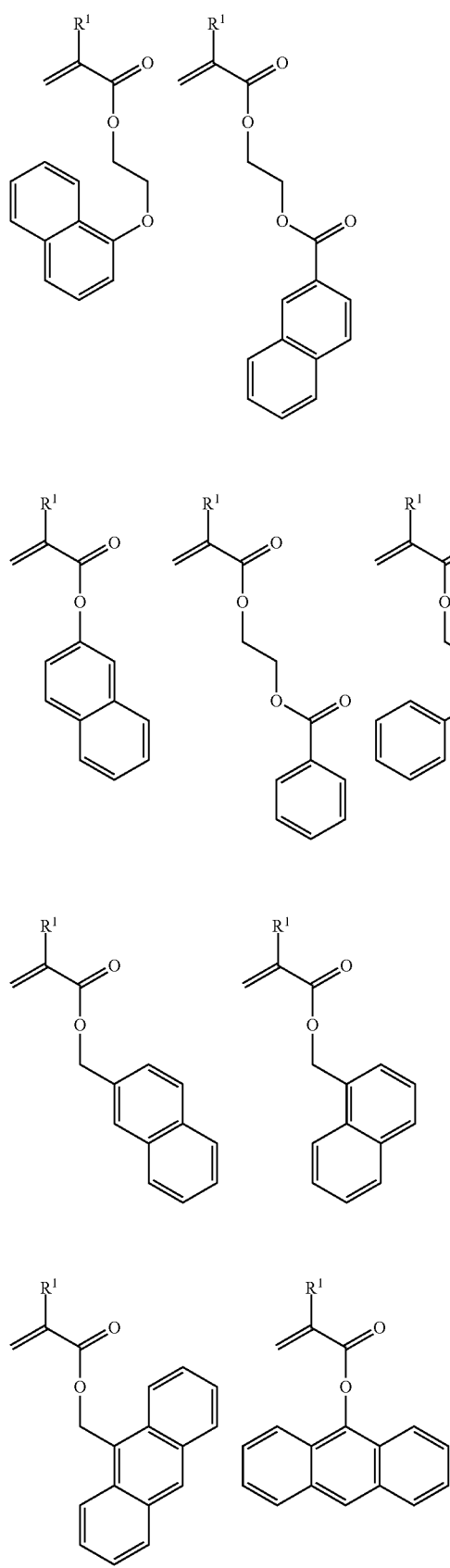
114
-continued
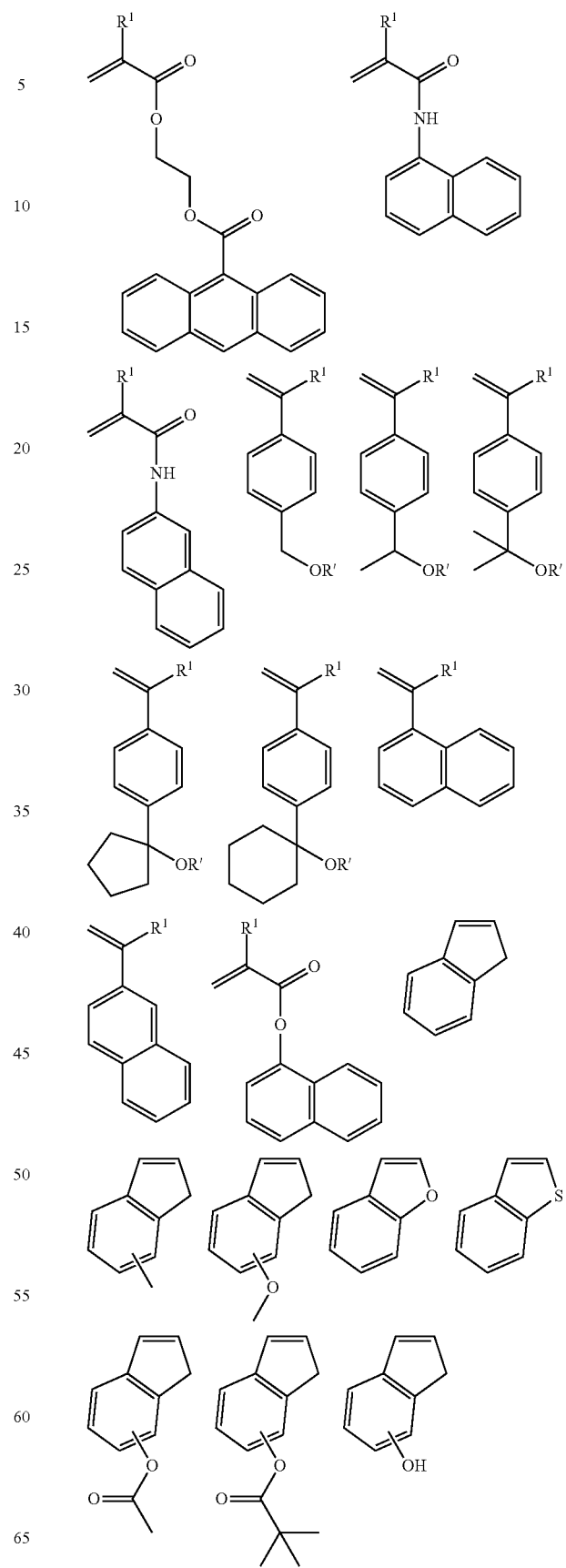

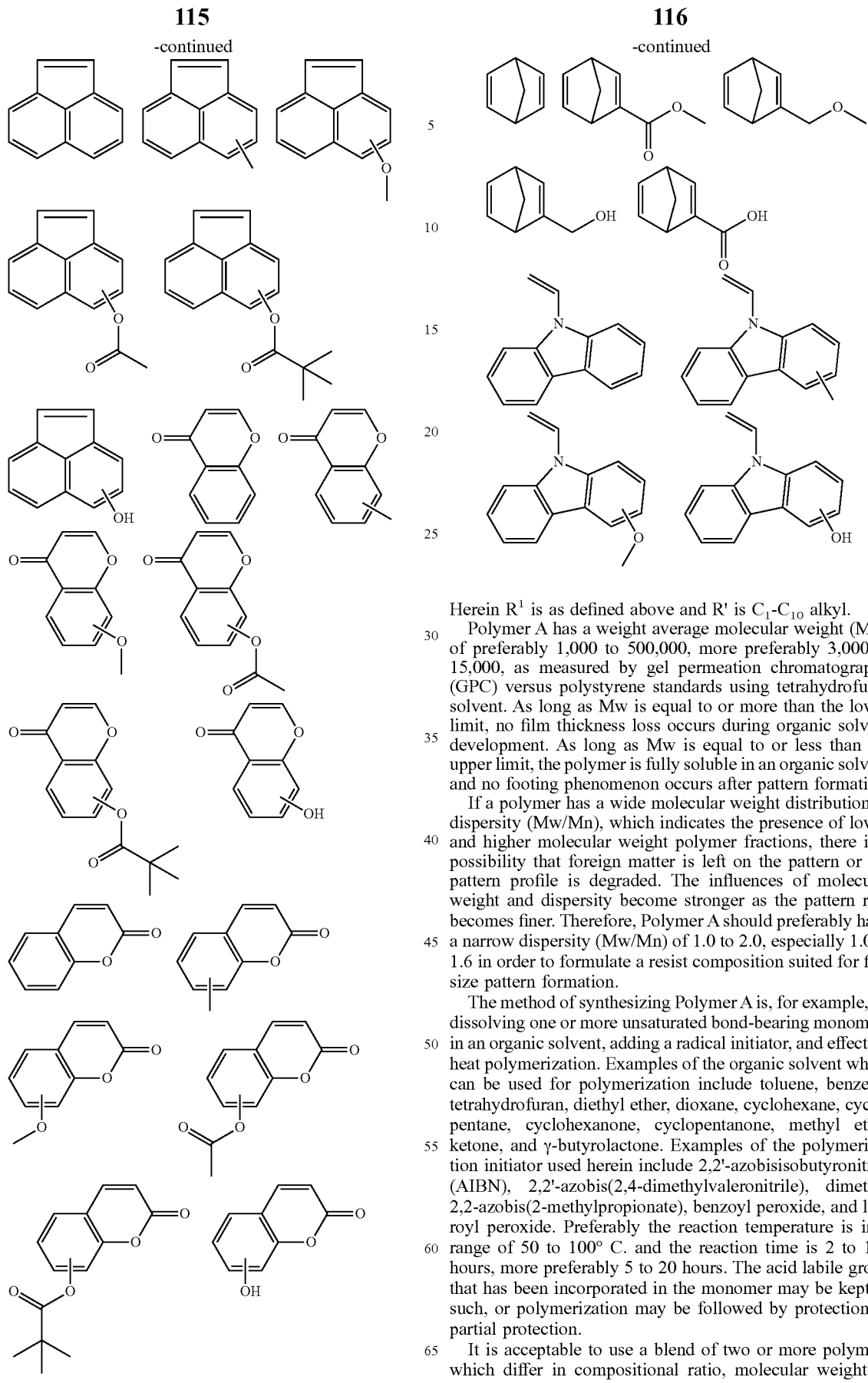

Herein R¹ is as defined above and R' is $C_1$-$C_{10}$ alkyl.

Polymer A has a weight average molecular weight (Mw) of preferably 1,000 to 500,000, more preferably 3,000 to 15,000, as measured by gel permeation chromatography (GPC) versus polystyrene standards using tetrahydrofuran solvent. As long as Mw is equal to or more than the lower limit, no film thickness loss occurs during organic solvent development. As long as Mw is equal to or less than the upper limit, the polymer is fully soluble in an organic solvent and no footing phenomenon occurs after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, Polymer A should preferably have a narrow dispersity (Mw/Mn) of 1.0 to 2.0, especially 1.0 to 1.6 in order to formulate a resist composition suited for fine size pattern formation.

The method of synthesizing Polymer A is, for example, by dissolving one or more unsaturated bond-bearing monomers in an organic solvent, adding a radical initiator, and effecting heat polymerization. Examples of the organic solvent which can be used for polymerization include toluene, benzene, tetrahydrofuran, diethyl ether, dioxane, cyclohexane, cyclopentane, cyclohexanone, cyclopentanone, methyl ethyl ketone, and γ-butyrolactone. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is in a range of 50 to 100° C. and the reaction time is 2 to 100 hours, more preferably 5 to 20 hours. The acid labile group that has been incorporated in the monomer may be kept as such, or polymerization may be followed by protection or partial protection.

It is acceptable to use a blend of two or more polymers which differ in compositional ratio, molecular weight or dispersity as the base resin (A).

In a further embodiment, Polymer A may be blended with a polymer of the conventional type wherein the exposed region is dissolved on alkaline development such as (meth) acrylate polymer, polynorbornene, cycloolefin-maleic anhydride copolymer, or ring-opening metathesis polymerization (ROMP) polymer. Also, Polymer A may be blended with a (meth)acrylate polymer, polynorbornene, or cycloolefin-maleic anhydride copolymer having an acid labile group-substituted hydroxyl group wherein the exposed region is not dissolved by alkaline development, but a negative pattern is formed by organic solvent development.

While Polymer A as the base resin (A) comprises recurring units derived from monomers, the molar fractions of respective units preferably fall in the following range (mol %), but are not limited thereto:

(I) 0.1 to 70 mol %, more preferably 1 to 70 mol % of recurring units of at least one type having formula (4) or (5), (an amount equal to or more than the lower limit provides a full PAG function whereas an amount equal to or less than the upper limit minimizes the risk of performance degradation such as sensitivity lowering), (II) 1 to 80 mol %, more preferably 5 to 70 mol %, even more preferably 10 to 60 mol % of recurring units of at least one type having formula (6), (III) 20 to 99 mol %, more preferably 30 to 95 mol %, even more preferably 30 to 90 mol % of recurring units of at least one type having formula (7), (IV) 0 to 20 mol %, more preferably 0 to 15 mol %, and even more preferably 0 to 10 mol % of recurring units of at least one type having formula (d1), (d2), (d3) or (d4), and (V) 0 to 80 mol %, more preferably 0 to 70 mol %, and even more preferably 0 to 50 mol % of recurring units of at least one type having formula (e) or derived from another monomer(s).

Component B

The resist composition may comprise (B) an organic solvent. The organic solvent used herein is not particularly limited as long as the base resin, PAG, acid diffusion regulator (or quencher) and other additives are soluble therein. Examples of the organic solvent are described in JP-A 2008-111103, paragraphs [0144]-[0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG is most soluble therein.

An appropriate amount of the organic solvent (B) used is 50 to 10,000 parts, more preferably 100 to 8,000 parts by weight per 100 parts by weight of the base resin (A).

Component C

The resist composition may further comprise (C) a photoacid generator other than the onium salt having formula (1). The PAG preferably has the formula (8).

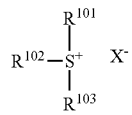

(8)

In formula (8), $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached. Examples of the sulfonium cation are the same as exemplified above for the sulfonium cation.

In formula (8), $X^-$ is an anion selected from the formulae (8A) to (8D).

(8A)

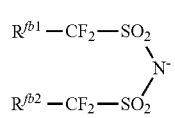

(8B)

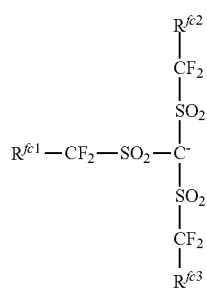

(8C)

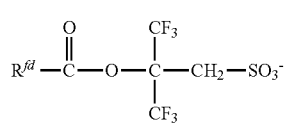

(8D)

In formula (8A), $R^{fa}$ is fluorine or a $C_1$-$C_{40}$ straight, branched or cyclic monovalent hydrocarbon group which may contain a heteroatom.

Of the anions of formula (8A), a structure having formula (8A') is preferred.

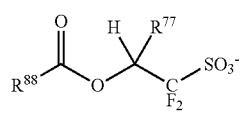

(8A')

In formula (8A'), $R^{77}$ is hydrogen or trifluoromethyl, preferably trifluoromethyl. $R^{88}$ is a $C_1$-$C_{40}$ straight, branched or cyclic monovalent hydrocarbon group which may contain a heteroatom. Suitable heteroatoms include oxygen, nitrogen, sulfur and halogen, with oxygen and nitrogen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy) methyl, acetoxymethyl, 2-carboxy-1-cyclohexyl, 2-oxopropyl, 4-oxo-1-adamantyl, and 3-oxocyclohexyl. Also included are the foregoing groups in which at least one hydrogen is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

With respect to the synthesis of the sulfonium salt having an anion of formula (8A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (8A) are shown below, but not limited thereto.

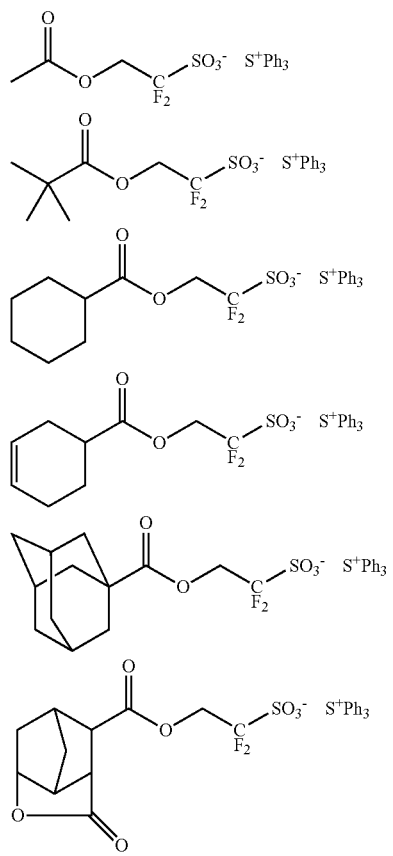

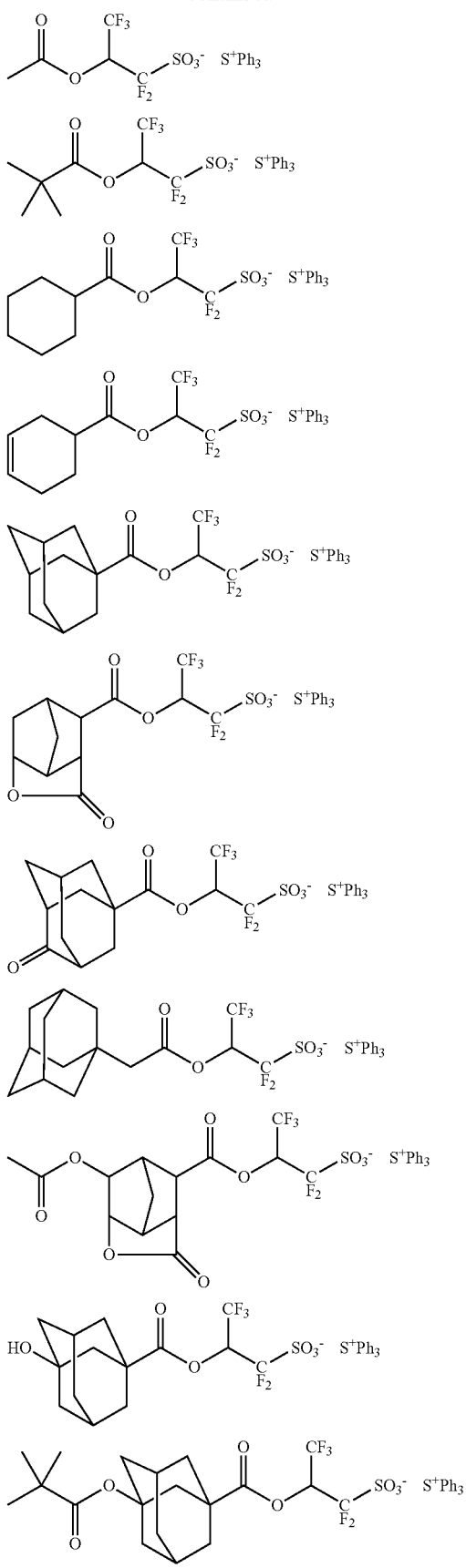

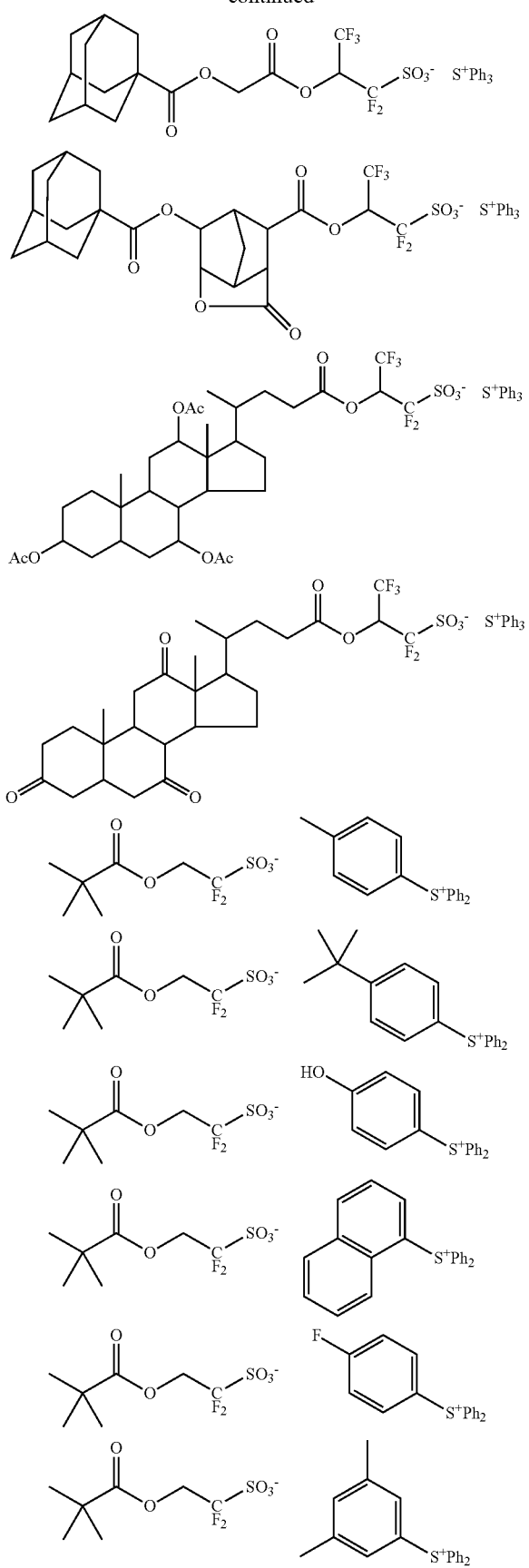
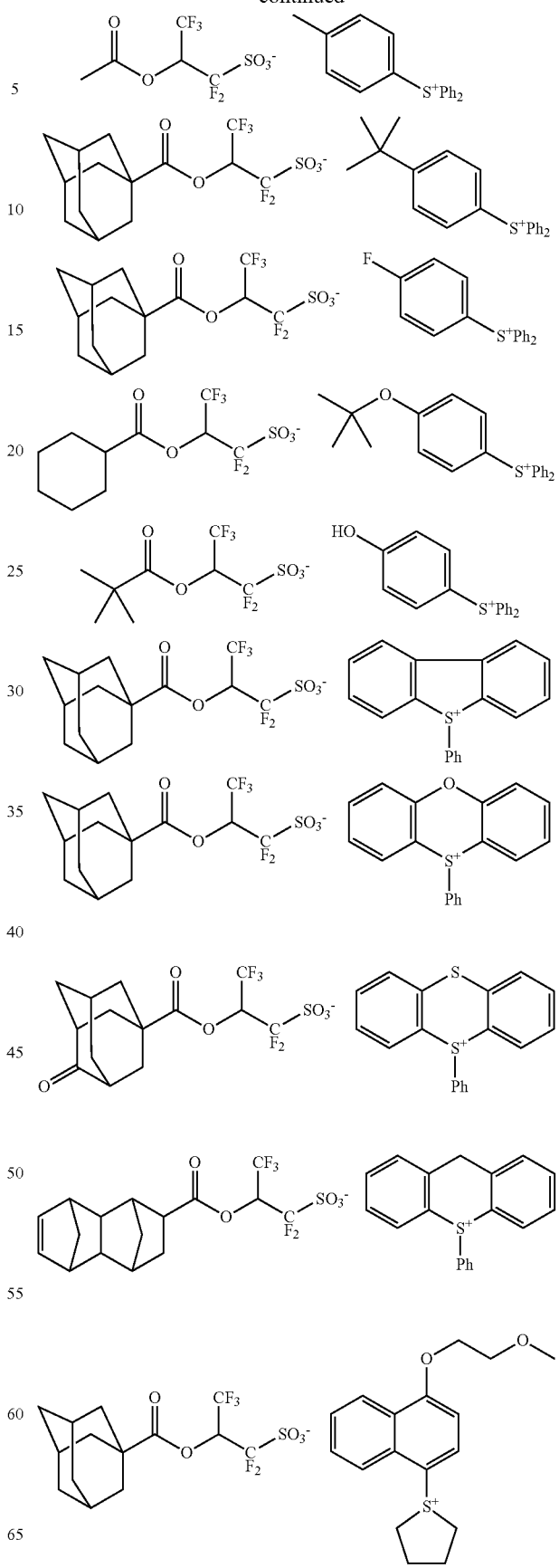

-continued

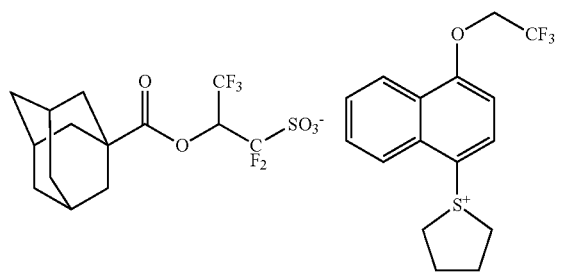

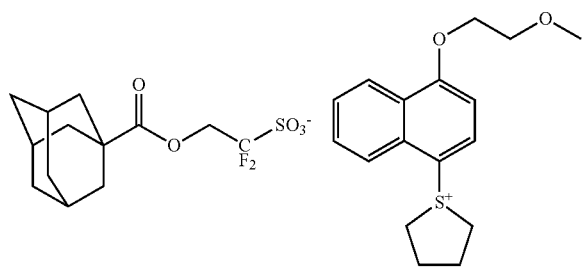

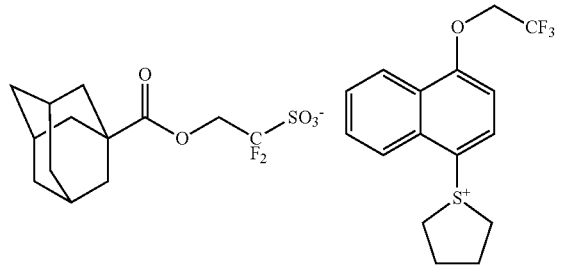

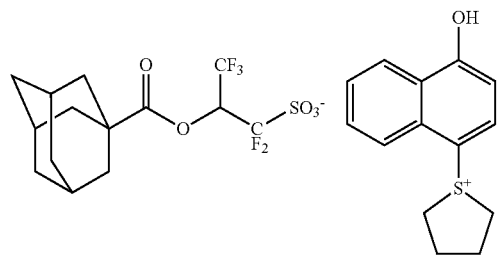

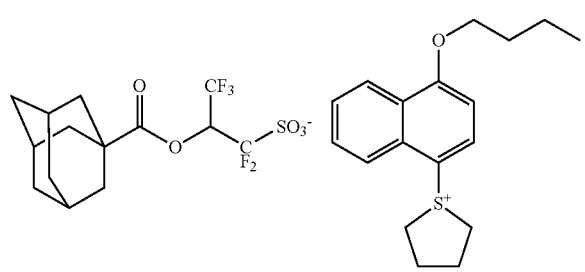

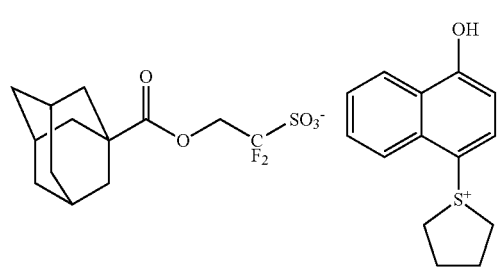

-continued

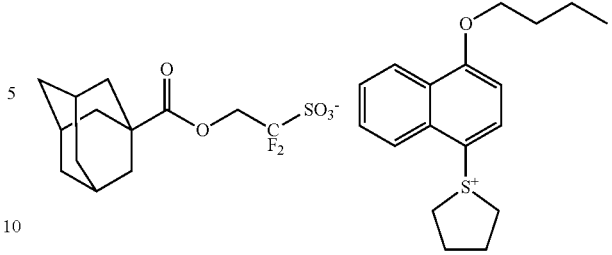

In formula (8B), $R^{fb1}$ and $R^{fb2}$ are each independently fluorine or a $C_1$-$C_{40}$ straight, branched or cyclic monovalent hydrocarbon group which may contain a heteroatom. Suitable monovalent hydrocarbon groups are as exemplified above for $R^{a8}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (8C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Suitable monovalent hydrocarbon groups are as exemplified above for $R^{88}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group forming a ring structure.

In formula (8D), $R^{fd}$ is a $C_1$-$C_{40}$ straight, branched or cyclic monovalent hydrocarbon group which may contain a heteroatom. Suitable monovalent hydrocarbon groups are as exemplified above for $R^{88}$.

With respect to the synthesis of the sulfonium salt having an anion of formula (8D), reference is made to JP-A 2010-215608 and JP-A 2014-133723.

Examples of the sulfonium salt having an anion of formula (8D) are shown below, but not limited thereto.

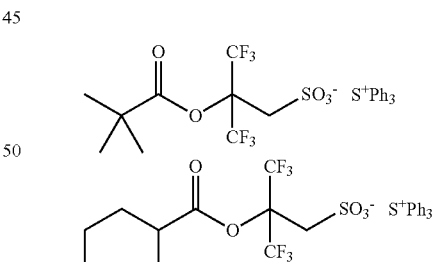

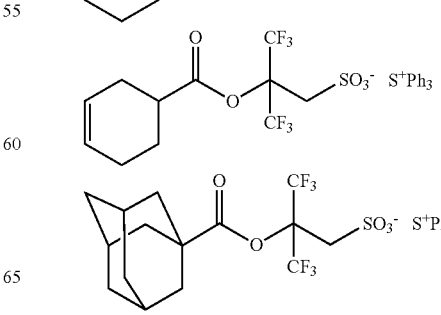

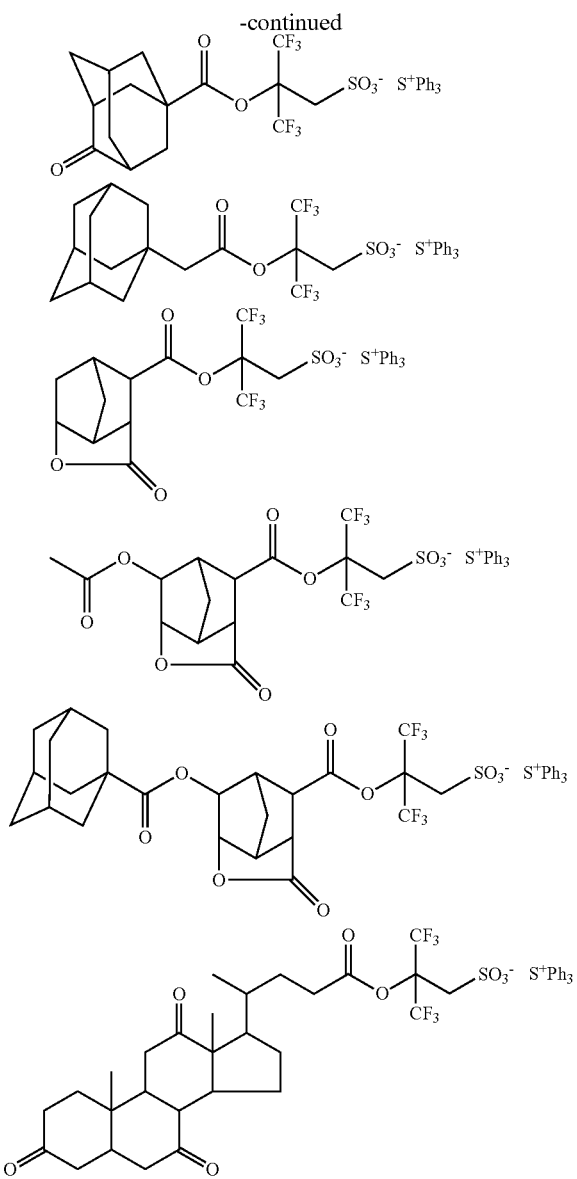

The compound having the anion of formula (SD) has a sufficient acid strength to cleave acid labile groups in the resist polymer because it is free of fluorine at α-position of sulfo group, but has two trifluoromethyl groups at β-position. Thus the compound is a useful PAG.

As the PAG (C), a compound having formula (9) is also preferred.

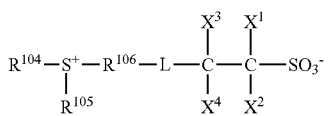

(9)

In formula (9), $R^{104}$ and $R^{105}$ are each independently a $C_1$-$C_{30}$ straight, branched or cyclic monovalent hydrocarbon group which may contain a heteroatom. $R^{106}$ is a $C_1$-$C_{30}$ straight, branched or cyclic divalent hydrocarbon group which may contain a heteroatom. Any two of $R^{104}$, $R^{105}$ and $R^{106}$ may bond together to form a ring with the sulfur atom to which they are attached. L is a single bond, ether bond or a $C_1$-$C_{20}$ straight, branched or cyclic divalent hydrocarbon group which may contain a heteroatom. $X^1$, $X^2$, $X^3$ and $X^4$ are each independently hydrogen, fluorine or trifluoromethyl, with the proviso that at least one of $X^1$, $X^2$, $X^3$ and $X^4$ is a substituent group other than hydrogen.

Examples of the monovalent hydrocarbon group are as exemplified above for R.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Suitable heteroatoms include oxygen, nitrogen, sulfur and halogen, with oxygen being preferred.

Of the PAGs having formula (9), those having the formula (9') are preferred.

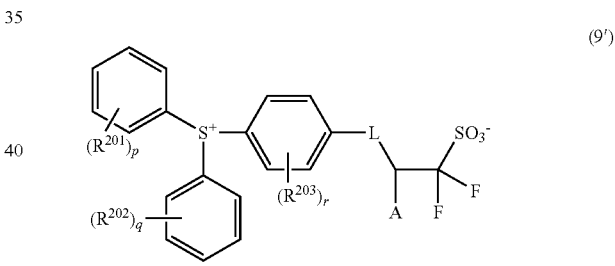

(9')

In formula (9'), L is as defined above. A is hydrogen or trifluoromethyl, preferably trifluoromethyl. $R^{201}$, $R^{202}$ and $R^{203}$ are each independently hydrogen or a $C_1$-$C_{20}$ straight, branched or cyclic monovalent hydrocarbon group which may contain a heteroatom. Suitable monovalent hydrocarbon groups are as exemplified above for $R^8$. The subscripts p and q each are an integer of 0 to 5, and r is an integer of 0 to 4.

Examples of the PAG having formula (9) are shown below, but not limited thereto. Herein A is as defined above.

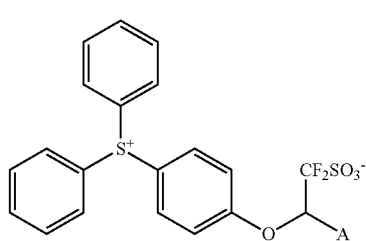

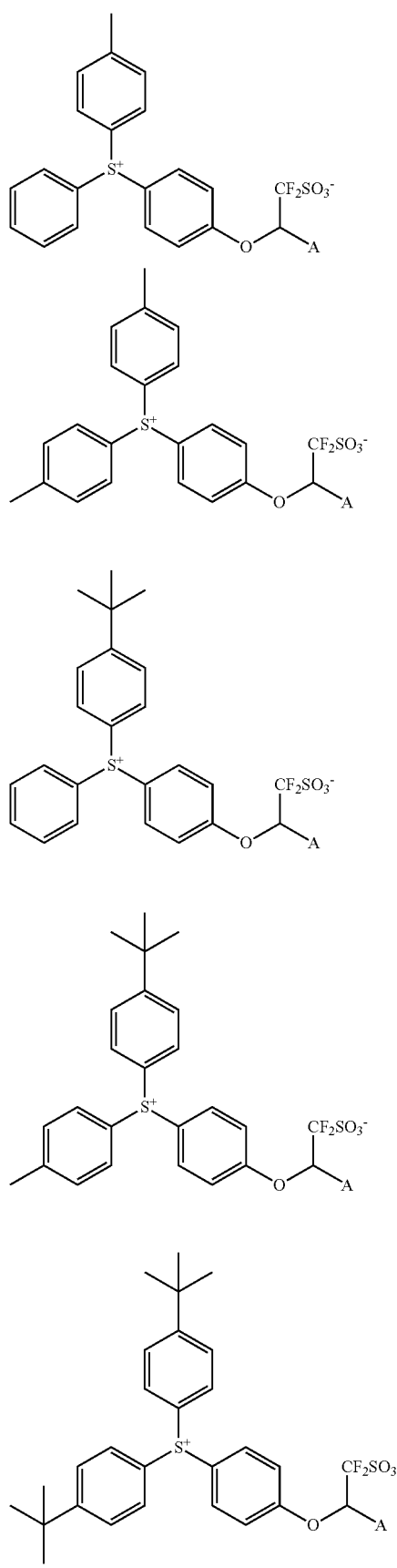
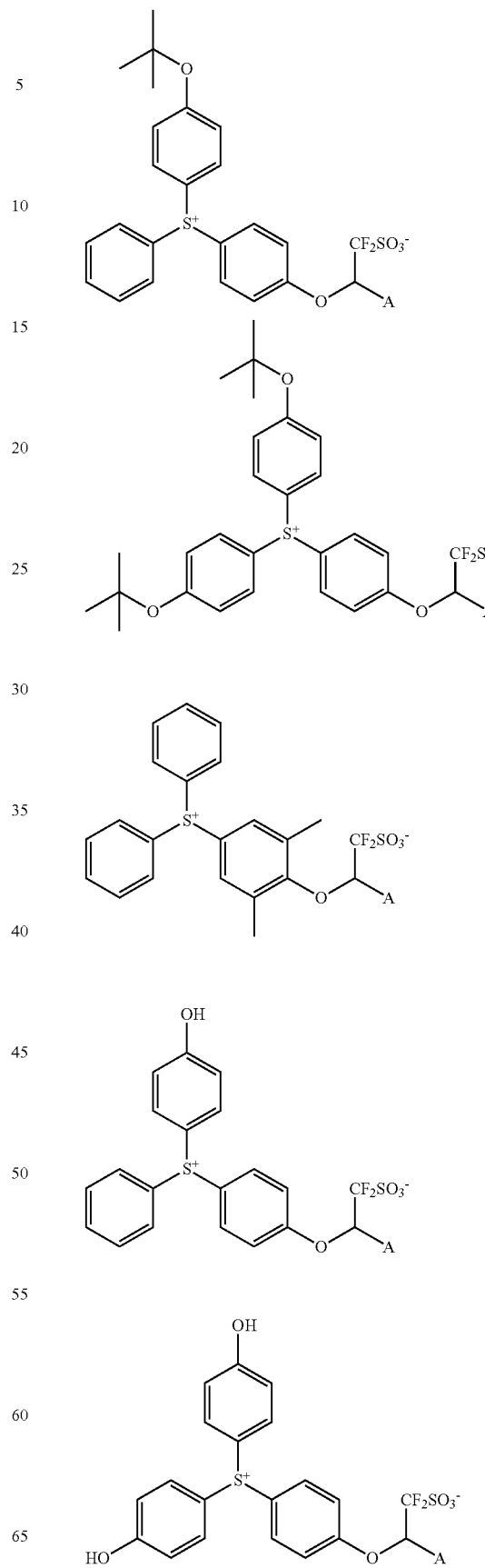

129
-continued
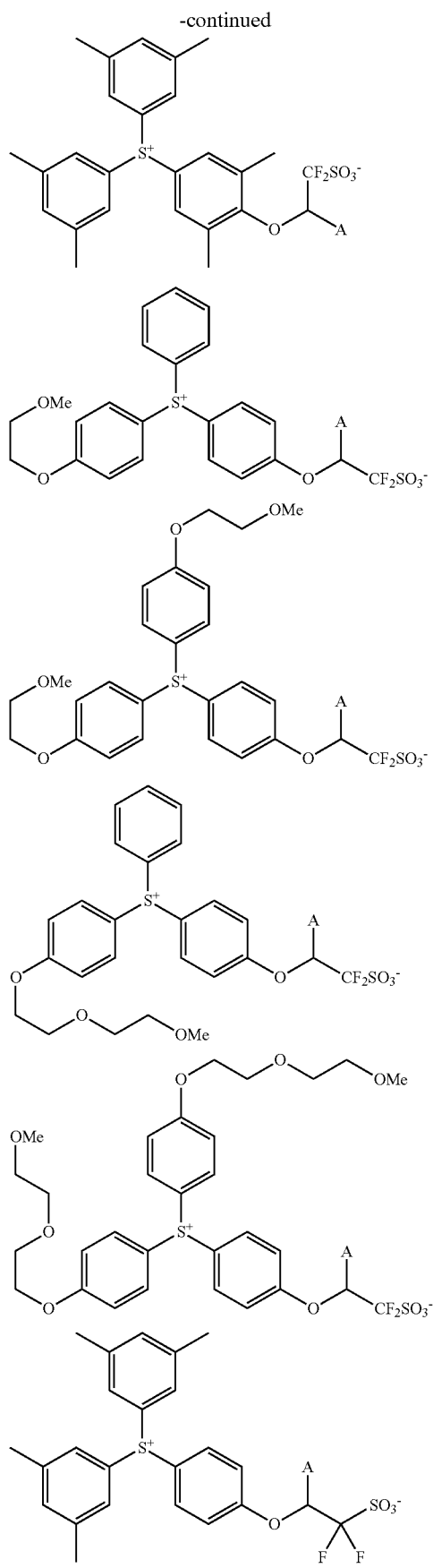
130
-continued
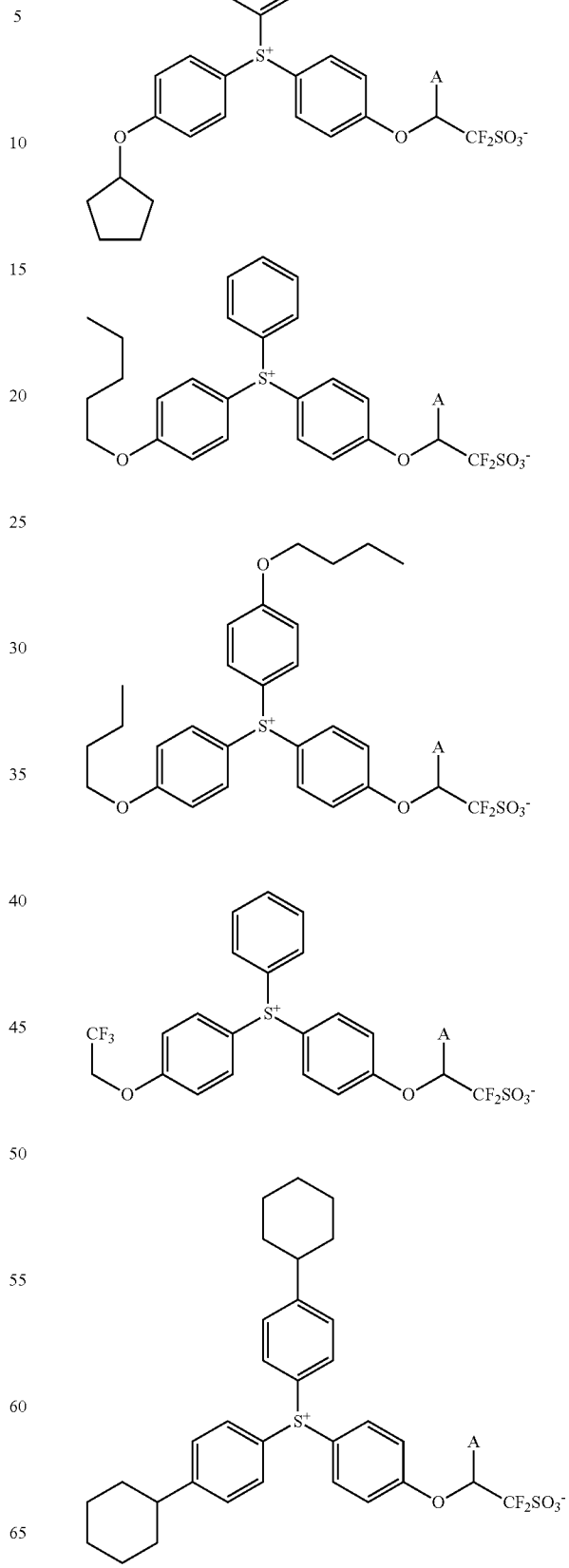

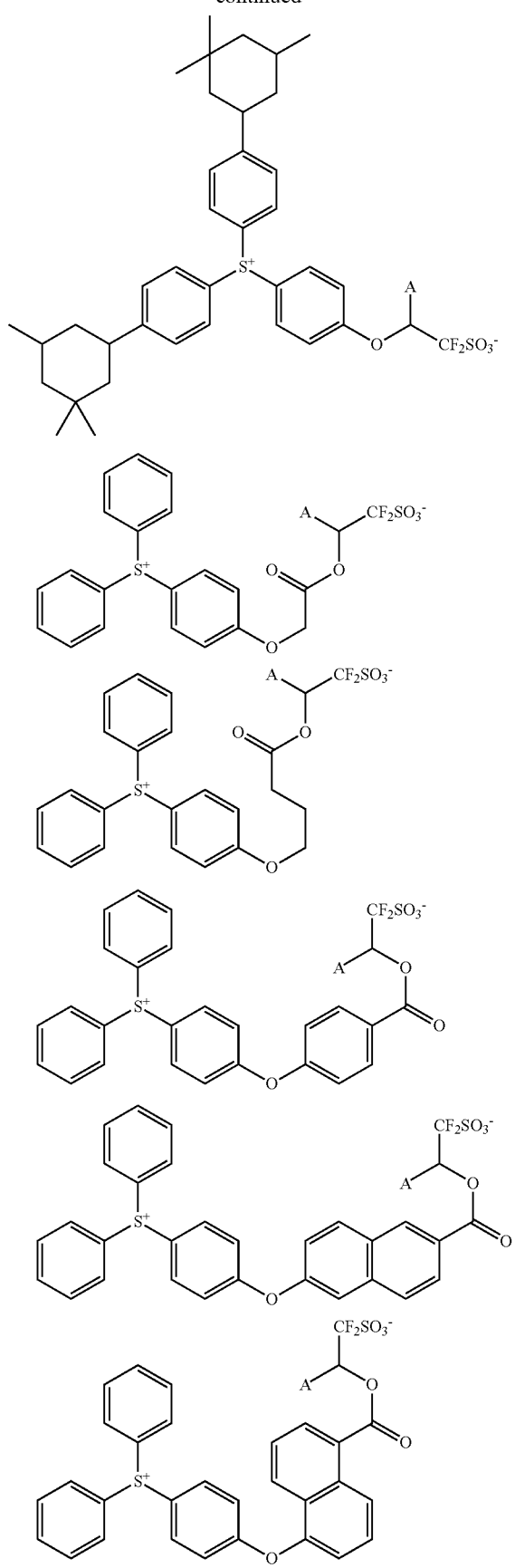

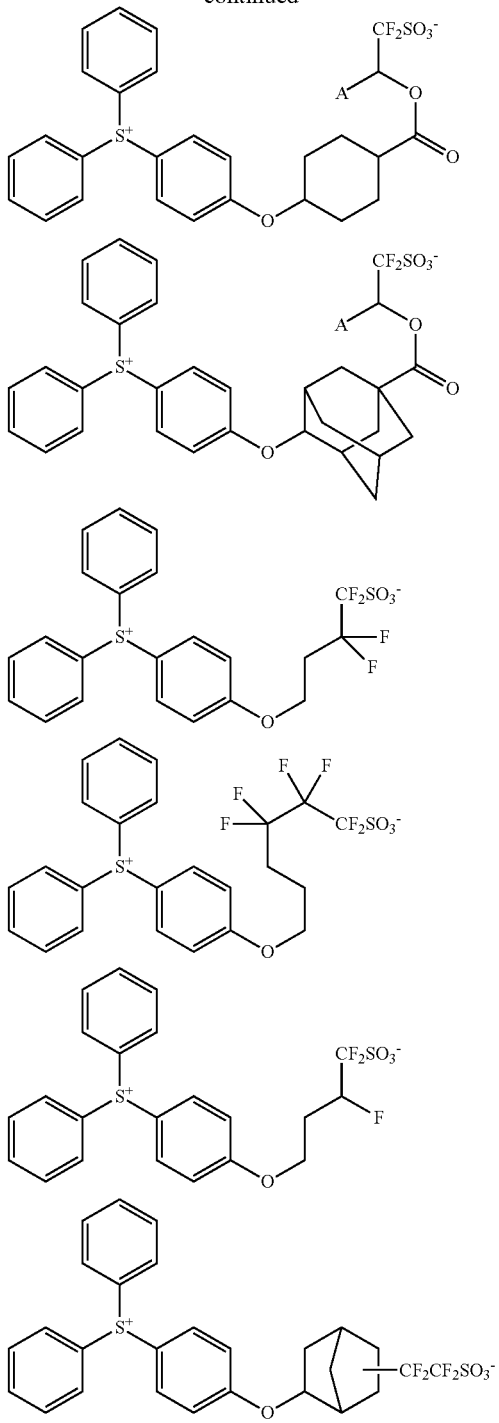

Of the foregoing PAGs, those compounds having an anion of formula (8A') or (8D) are especially preferred because of reduced acid diffusion and high solubility in resist solvent, and those compounds having an anion of formula (9') are especially preferred because of minimized acid diffusion.

An appropriate amount of the PAG (C) added is 0 to 40 parts by weight per 100 parts by weight of the base resin (A). When PAG (C) is added, the lower limit is preferably 0.1 part, more preferably 0.5 part by weight, and the upper limit is preferably 20 parts, more preferably 10 parts by weight.

An amount in the range ensures good resolution and leaves no foreign particles after resist development or during separation.

Component D

The resist composition may further comprise (D) a quencher. As used herein, the "quencher" refers to a compound capable of suppressing the rate of diffusion when the acid generated by the PAG diffuses within the resist film. Suitable quenchers include primary, secondary and tertiary amine compounds, specifically amine compounds having a hydroxyl, ether, ester, lactone, cyano or sulfonate group, as described in JP-A 2008-111103, paragraphs [0146]-[0164] (U.S. Pat. No. 7,537,880), and compounds having primary or secondary amine protected with a carbamate group, as described in JP 3790649.

Also an onium salt of sulfonic acid which is not fluorinated at α-position or carboxylic acid as represented by the formula (10) or (11) is useful as the quencher.

(10)

(11)

Herein $R^{151}$, $R^{152}$ and $R^{153}$ are each independently hydrogen, halogen exclusive of fluorine, or a $C_1$-$C_{40}$ straight, branched or cyclic monovalent hydrocarbon group which may contain a heteroatom, any two of $R^{151}$, $R^{152}$ and $R^{153}$ may bond together to form a ring with the carbon atom to which they are attached. $R^{154}$ is a $C_1$-$C_{40}$ straight, branched or cyclic monovalent hydrocarbon group which may contain a heteroatom. $M^+$ is an onium cation.

The onium salt of sulfonic acid which is not fluorinated at α-position is described in U.S. Pat. No. 8,795,942 (JP-A 2008-158339). The PAGs capable of generating sulfonic acid which is not fluorinated at α-position are exemplified in JP-A 2010-155824, paragraphs [0019]-[0036] and JP-A 2010-215608, paragraphs [0047]-[0082]. The onium salts of carboxylic acid are described in JP 3991462.

The anion in formula (10) or (11) is a conjugated base of weak acid. As used herein, the weak acid indicates an acidity insufficient to deprotect an acid labile group from an acid labile group-containing unit in the base resin. The onium salt having formula (10) or (11) functions as a quencher when used in combination with an onium salt type photoacid generator having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved DOF and satisfactory dimensional control.

If a photoacid generator capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Of the onium salts of α-position non-fluorinated sulfonic acid and carboxylic acid, sulfonium salts of sulfonic acid having the following formula (Z1) and sulfonium salts of carboxylic acid having the formula (Z2) are preferred.

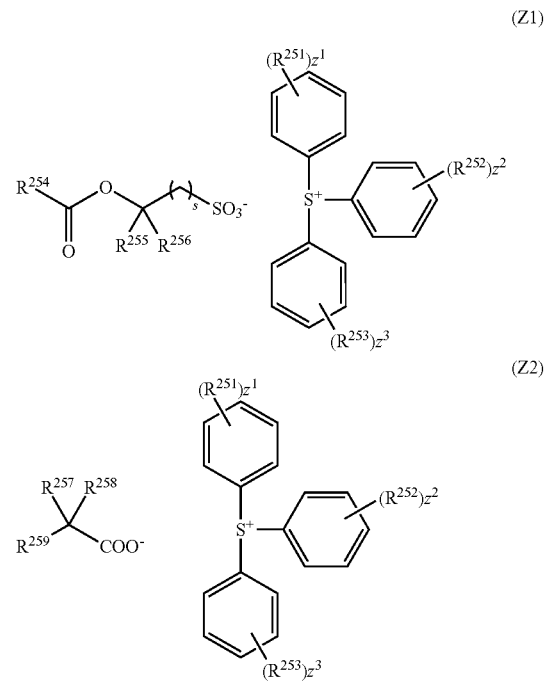

Herein $R^{251}$, $R^{252}$ and $R^{253}$ are each independently a $C_1$-$C_{20}$ straight, branched or cyclic monovalent hydrocarbon group which may contain a heteroatom, any two of $R^{251}$, $R^{252}$ and $R^{253}$ may bond together to form a ring with the atom to which they are attached and intervening atoms. $R^{254}$ is a $C_1$-$C_{40}$ straight, branched or cyclic monovalent hydrocarbon group which may contain a heteroatom. $R^{255}$ and $R^{256}$ are each independently hydrogen or trifluoromethyl. $R^{257}$ and $R^{258}$ are each independently hydrogen, fluorine or trifluoromethyl. $R^{259}$ is hydrogen, hydroxyl, a $C_1$-$C_{35}$ straight, branched or cyclic monovalent hydrocarbon group which may contain a heteroatom, or optionally substituted $C_6$-$C_{30}$ aryl group. The subscript s is an integer of 1 to 3, $z^1$, $z^2$ and $z^3$ are each independently an integer of 0 to 5.

Illustrative, non-limiting examples of the onium salts of α-position non-fluorinated sulfonic acid and carboxylic acid are given below.

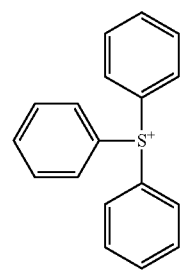 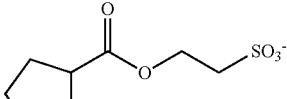

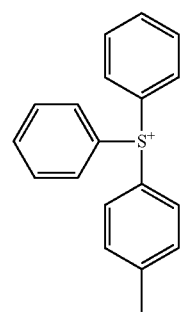 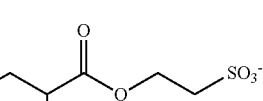

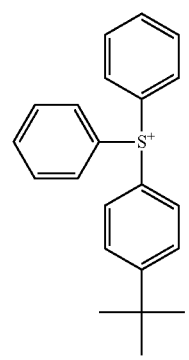 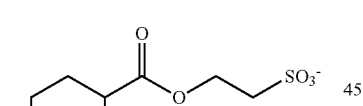

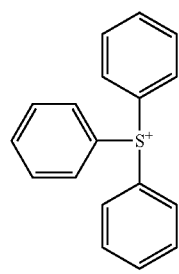 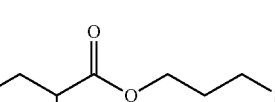

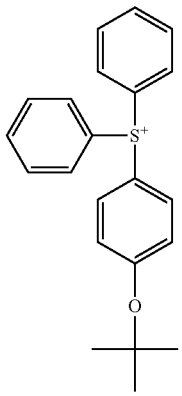 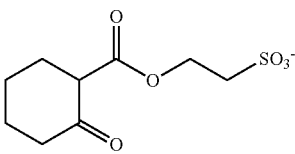

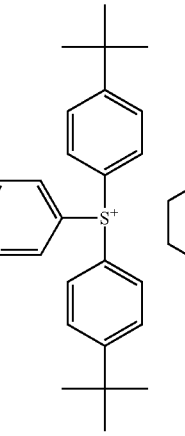 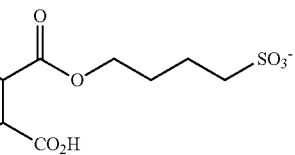

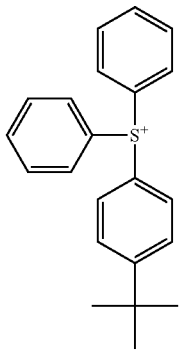 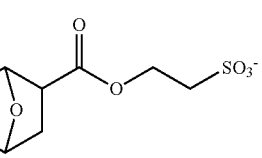

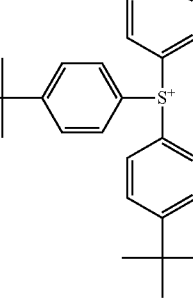 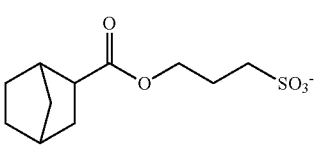

137
-continued
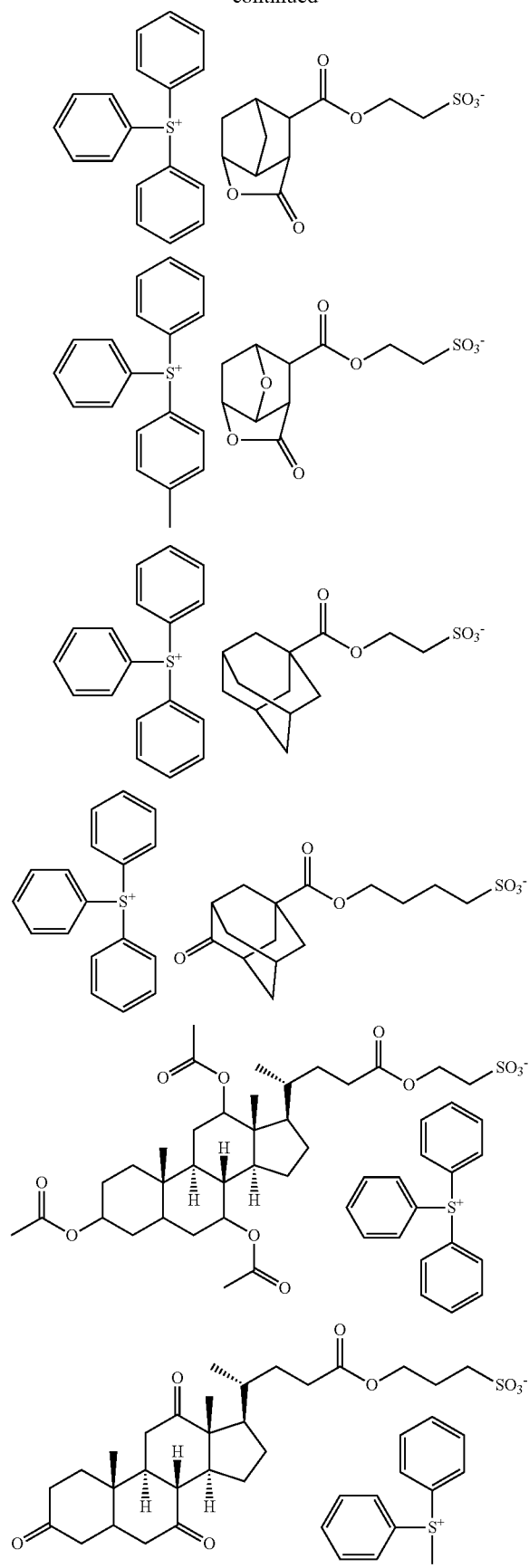
138
-continued
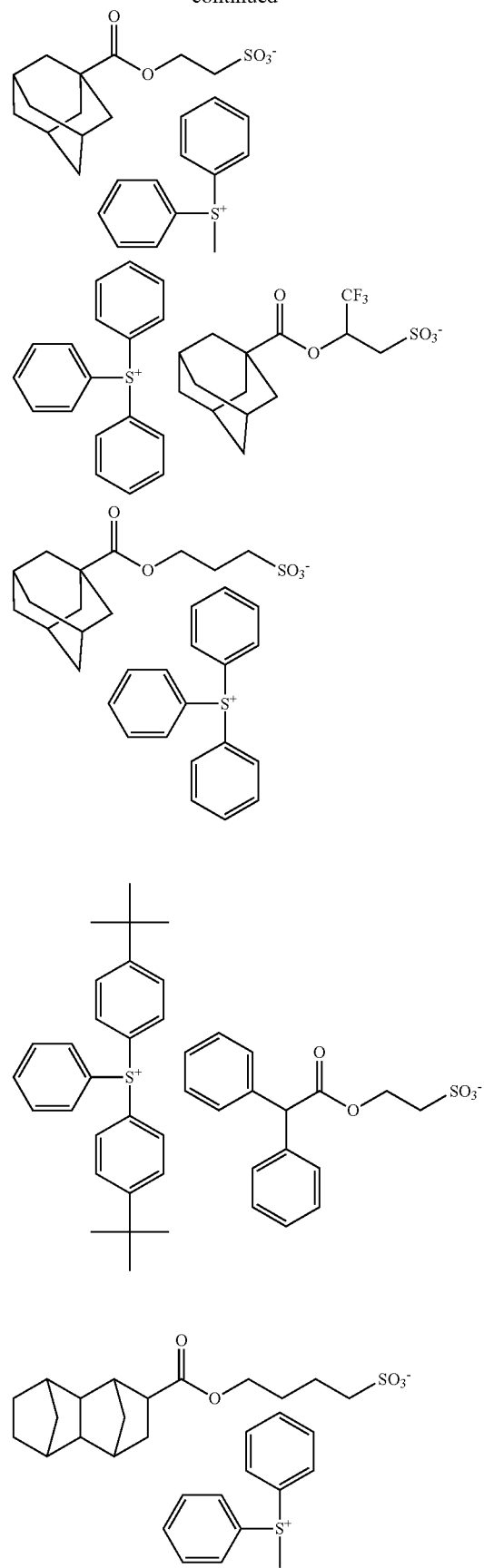

139
-continued
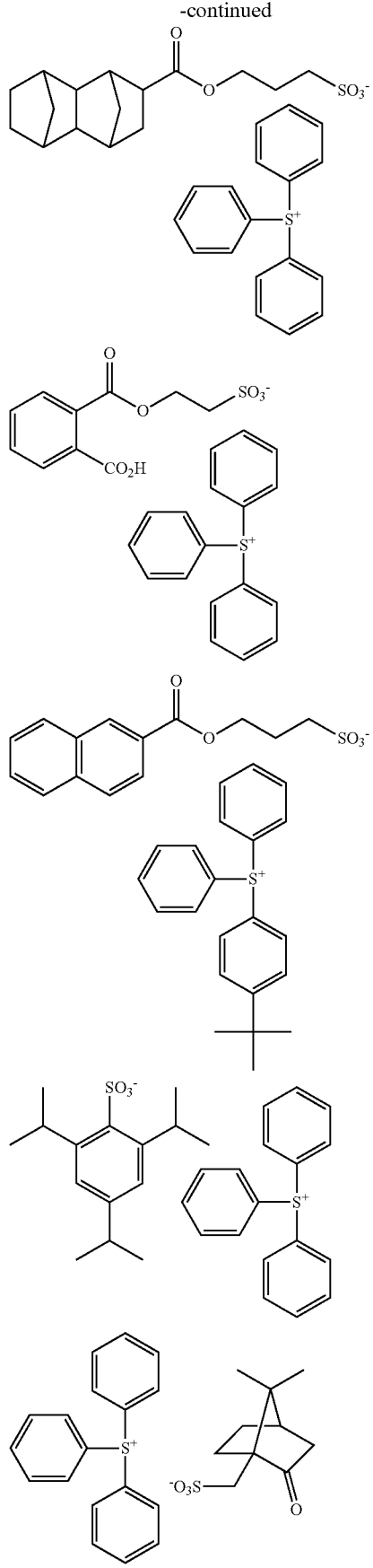
140
-continued
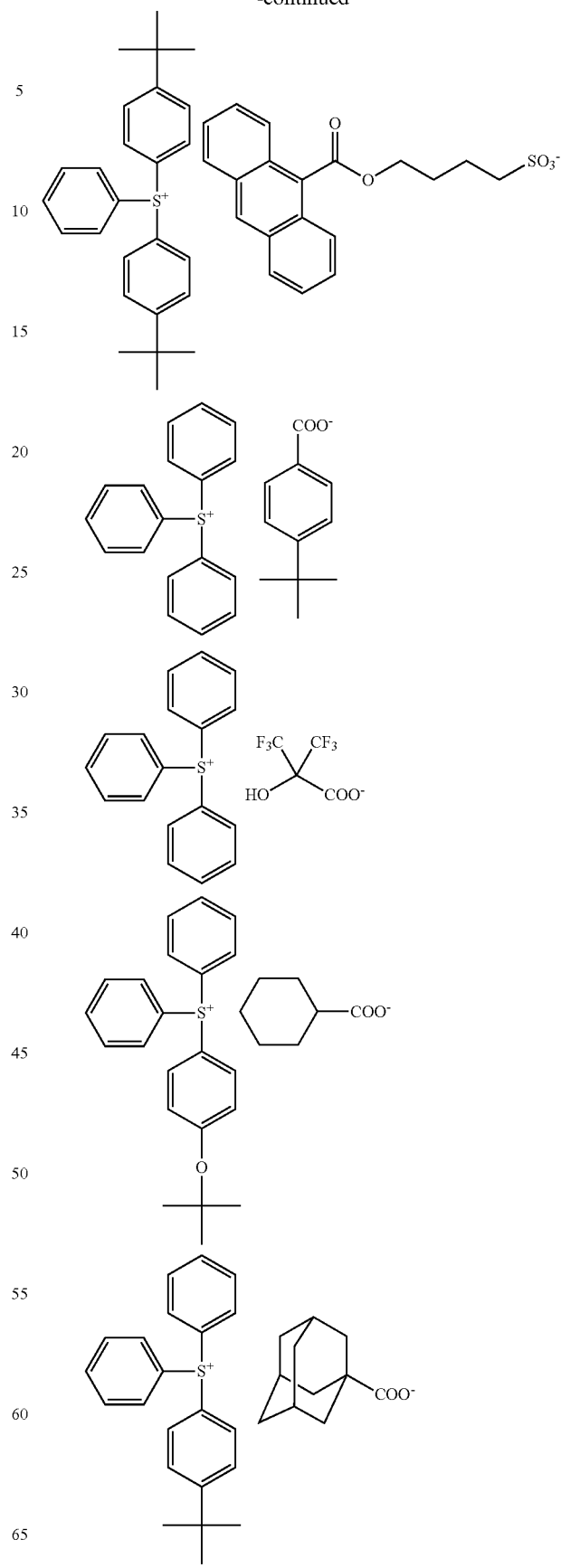

-continued
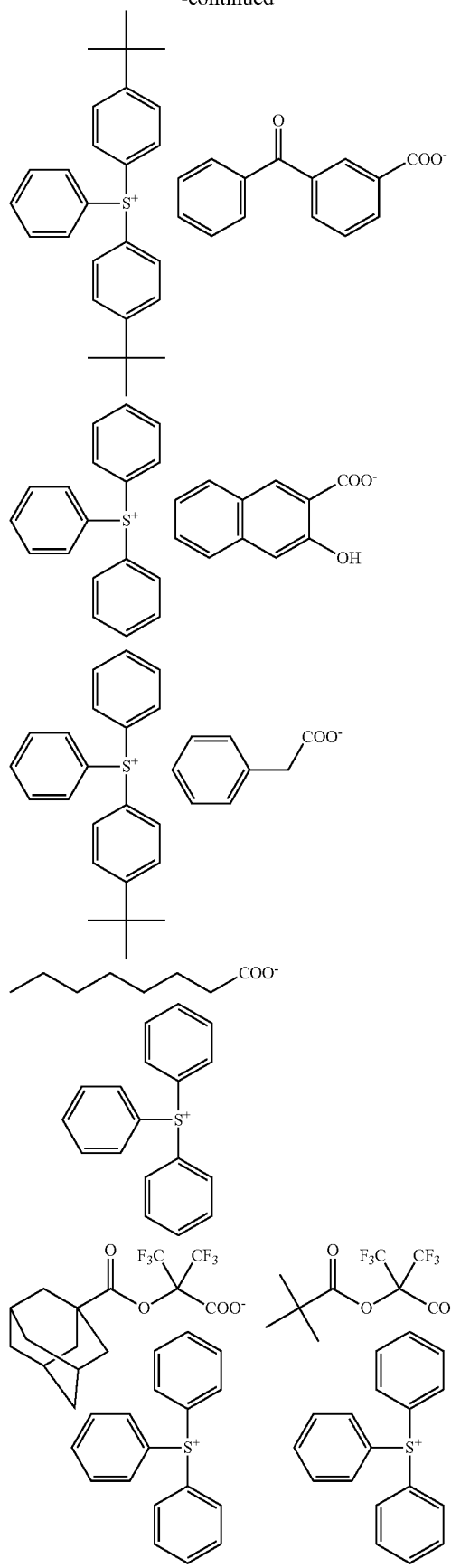
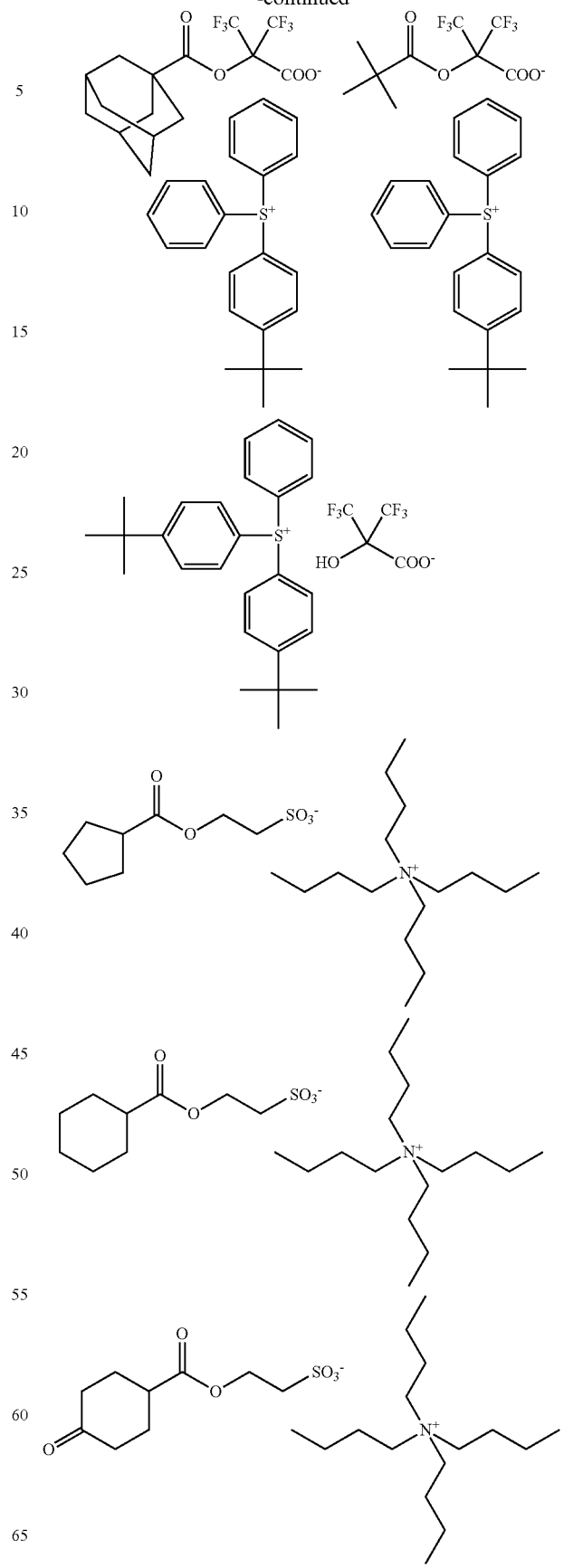

143
-continued
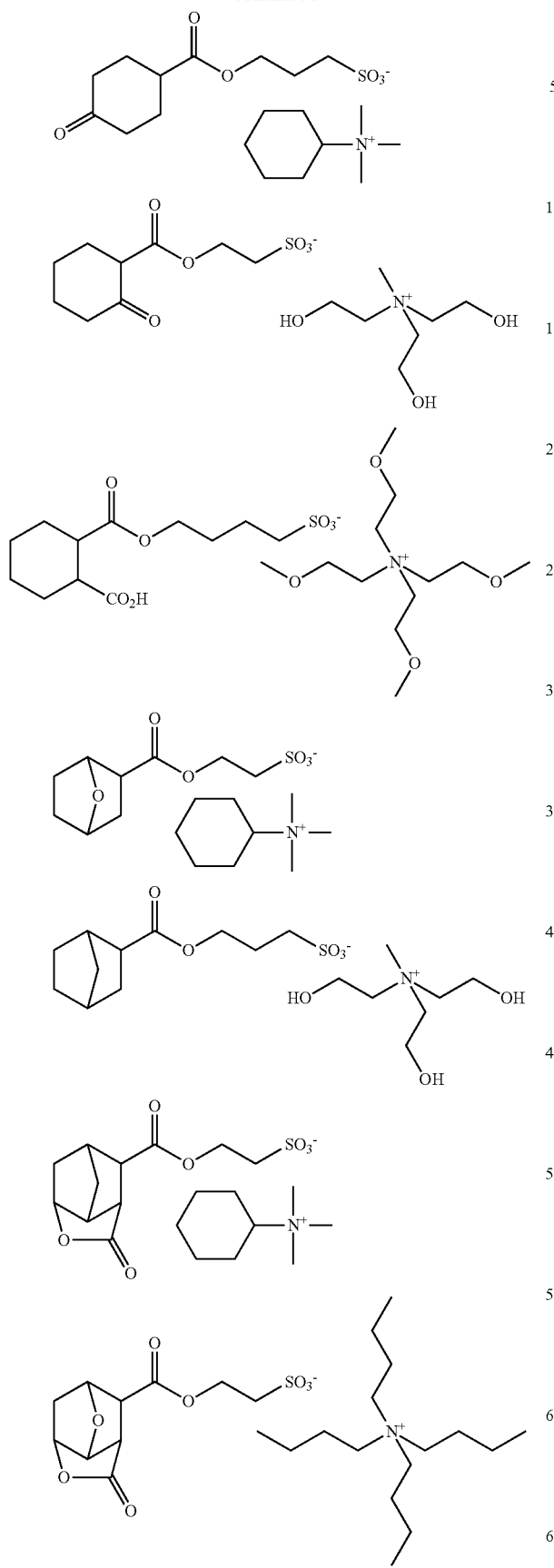
144
-continued
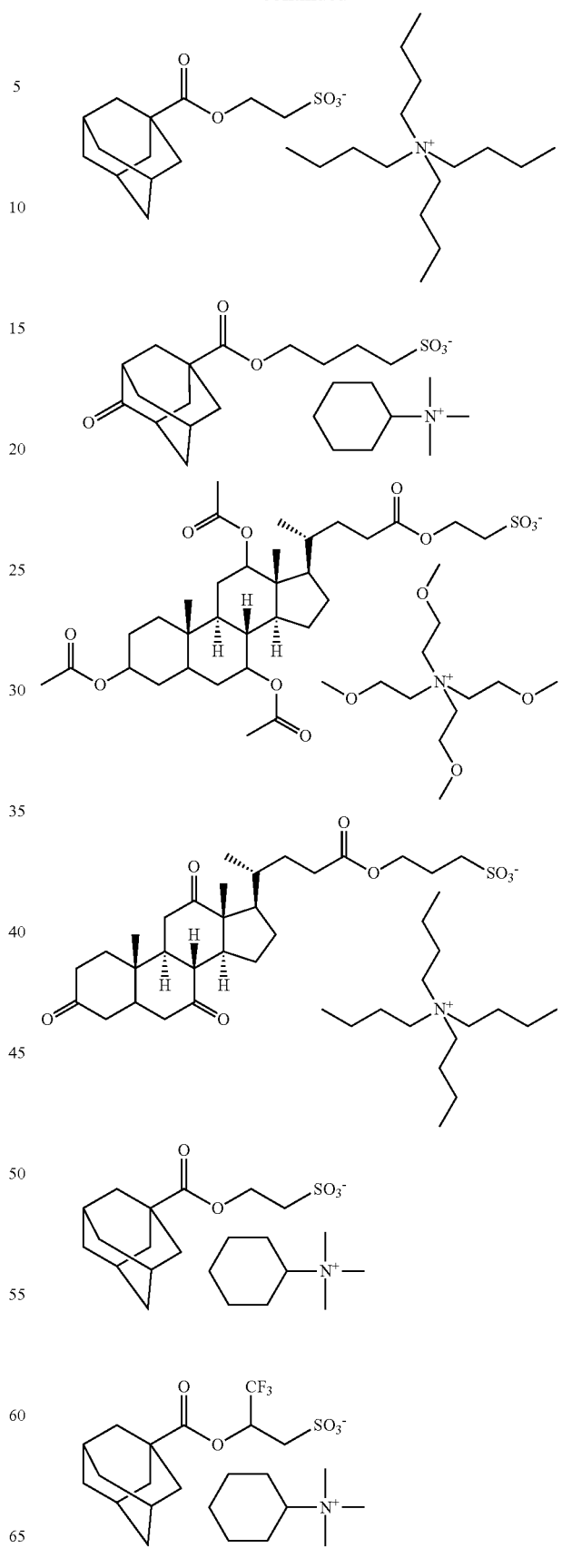

145
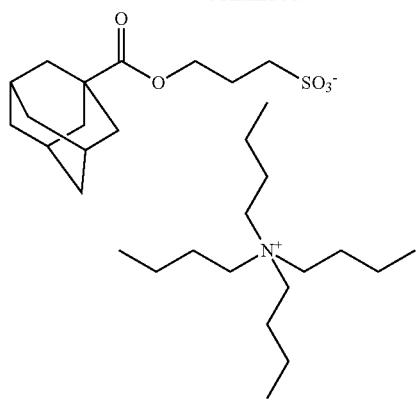
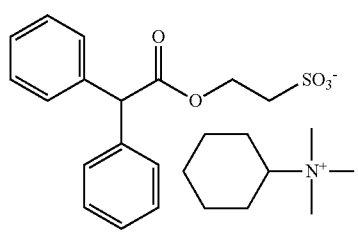
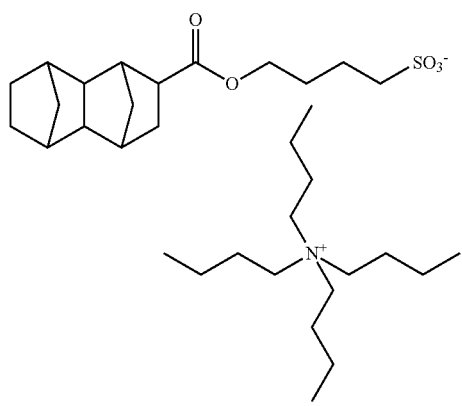
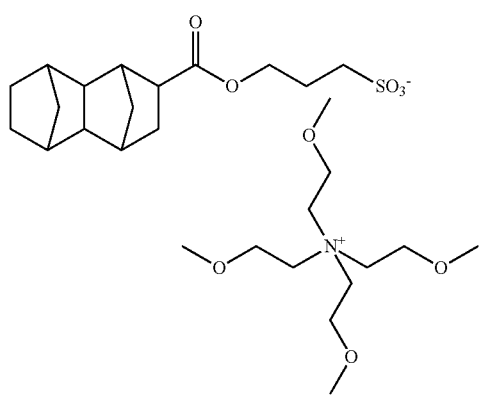
146
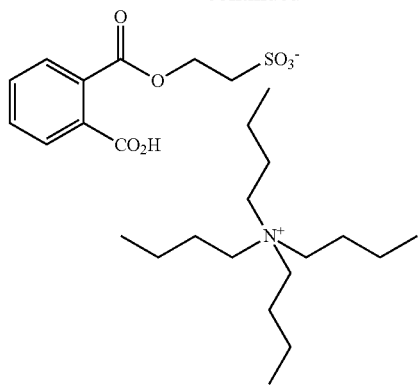
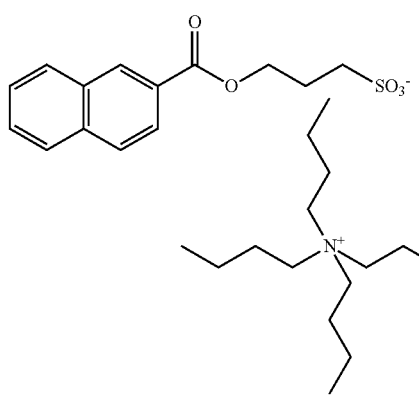
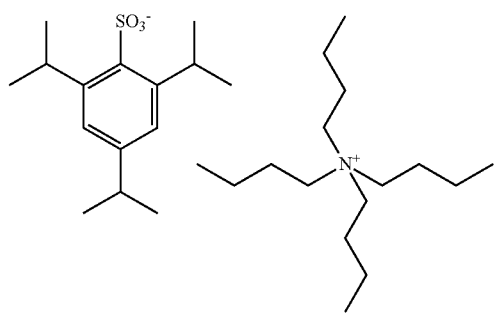
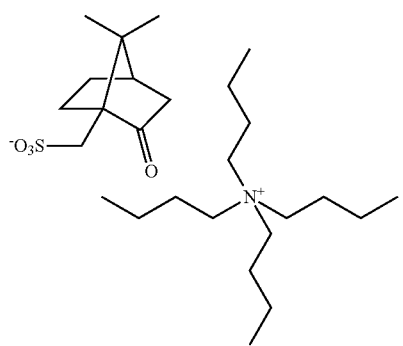

147
-continued
148
-continued
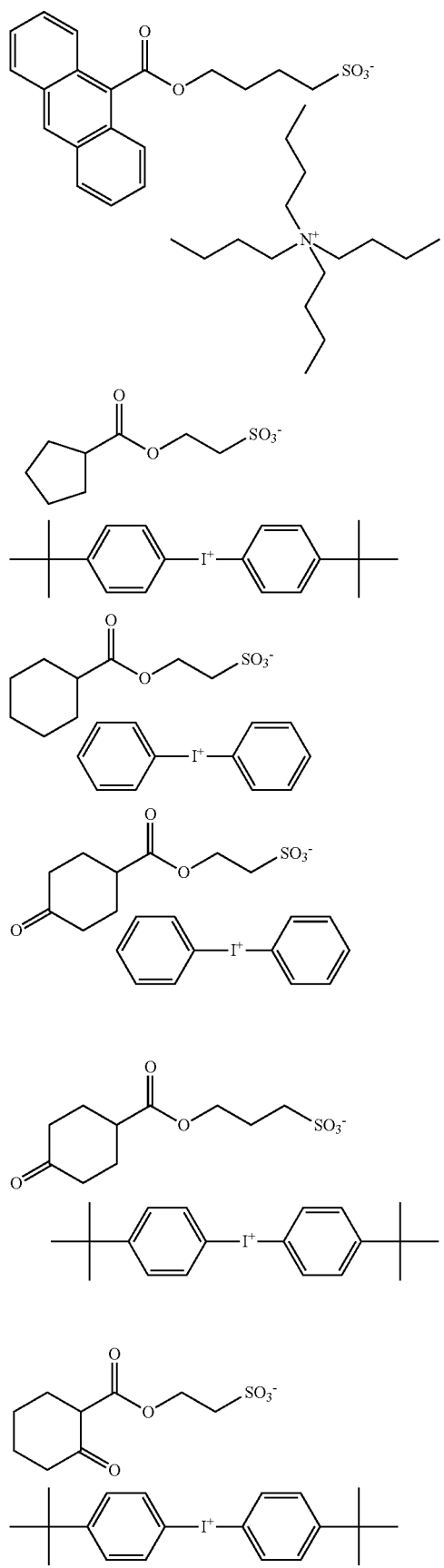
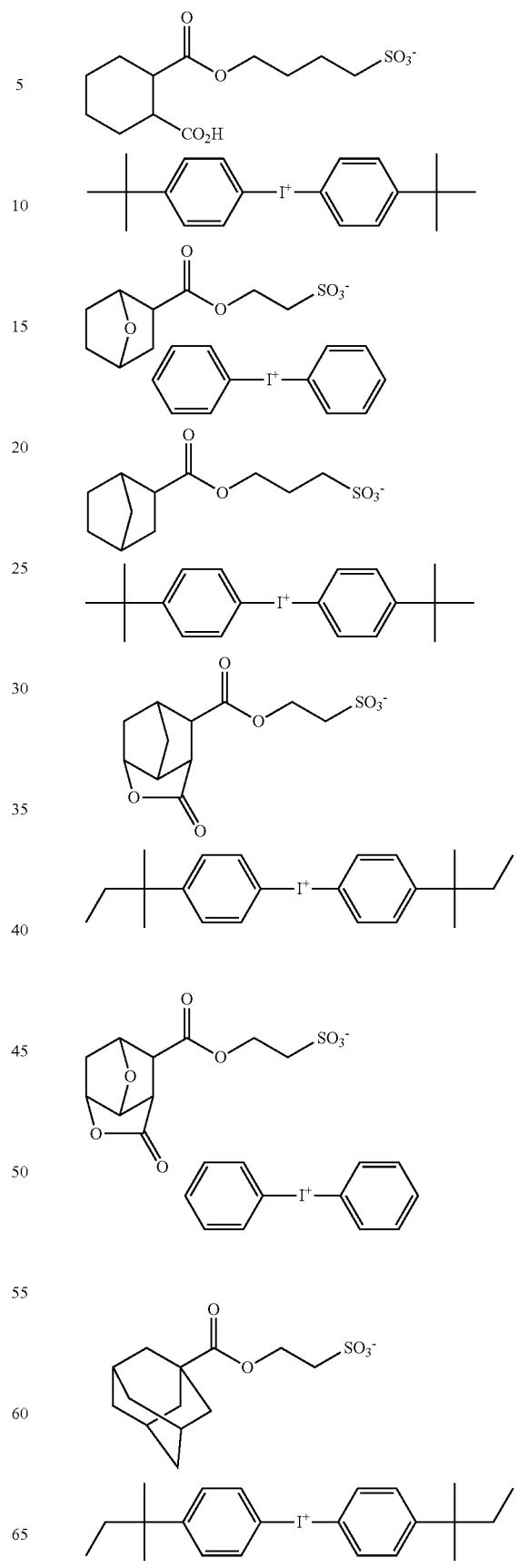

149
-continued
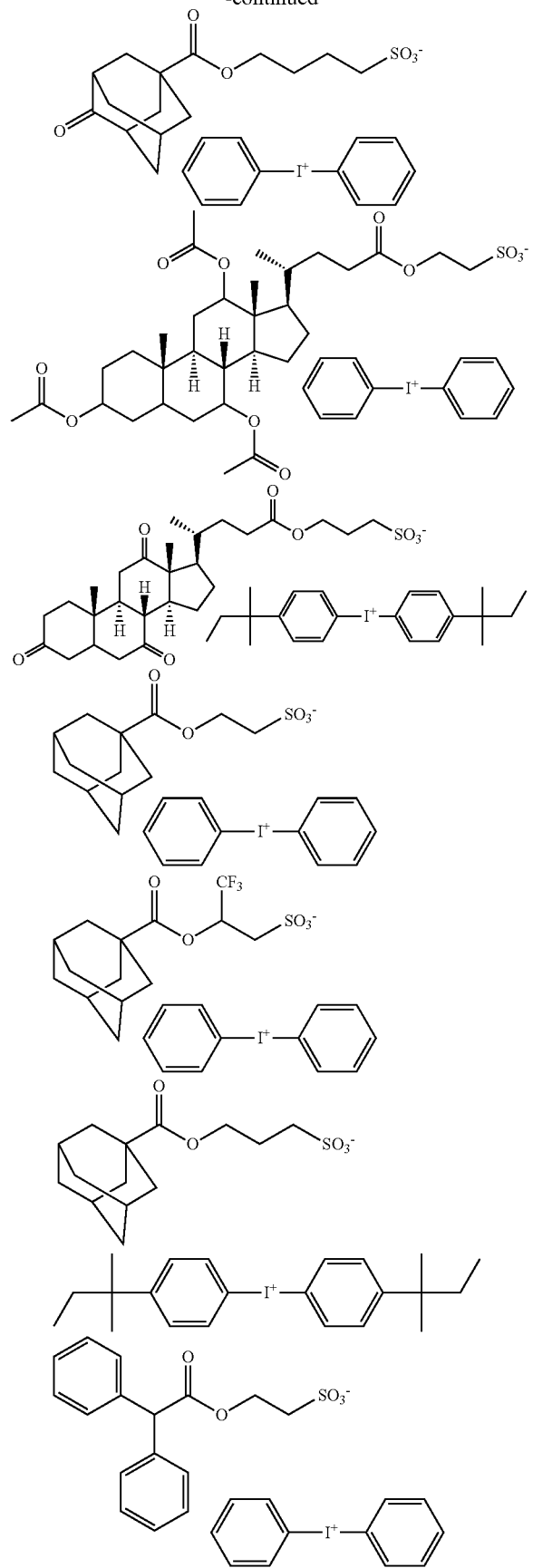
150
-continued
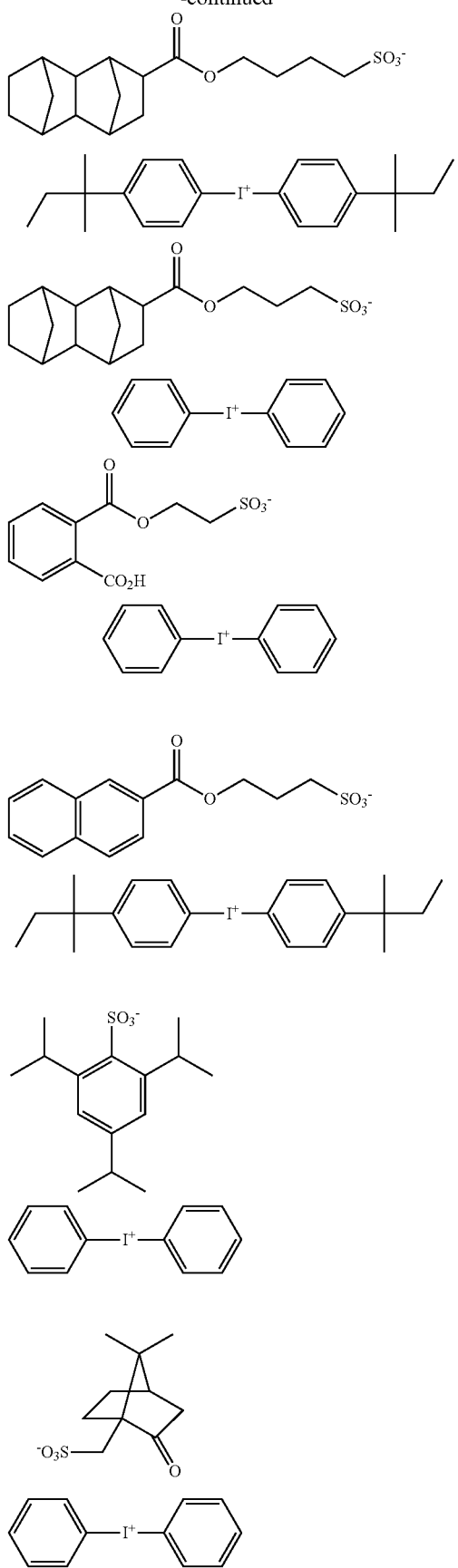

151
-continued
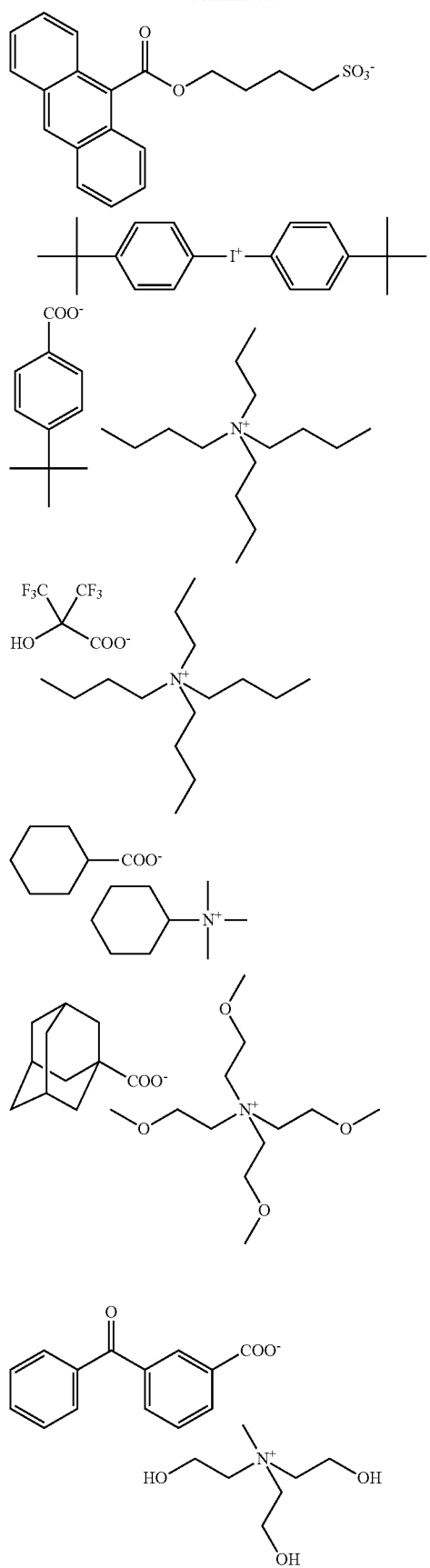
152
-continued
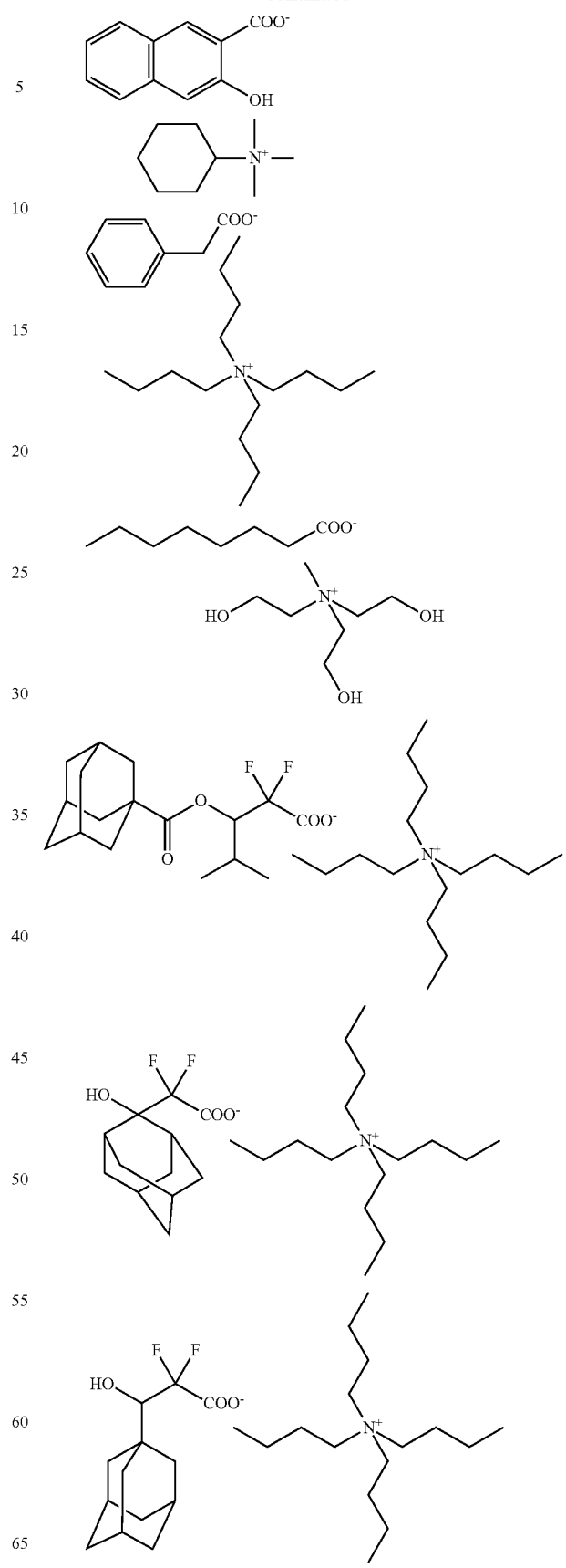

153
-continued
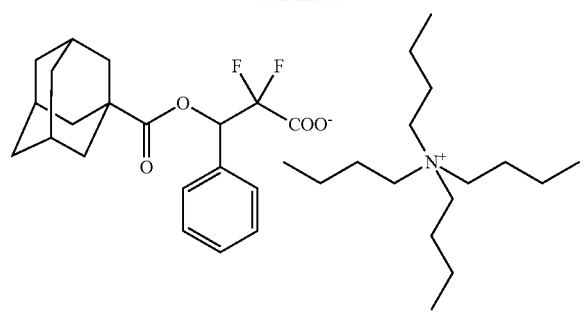
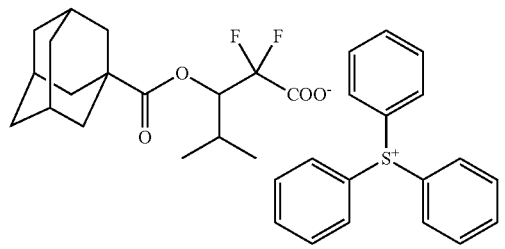
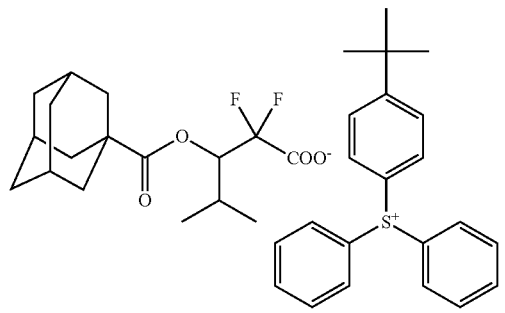
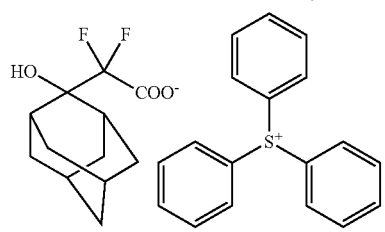
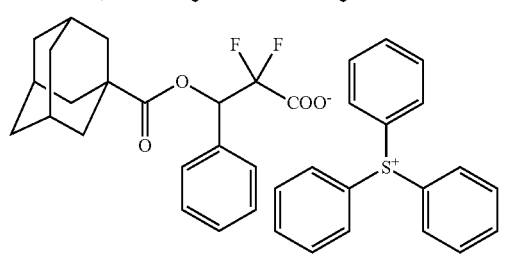
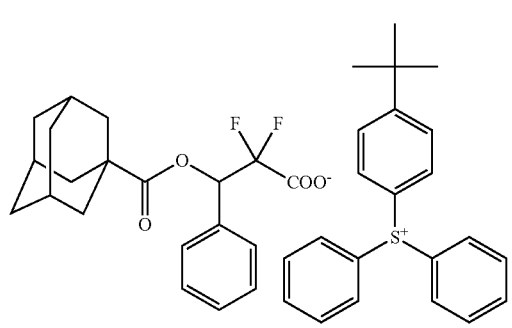
154
-continued
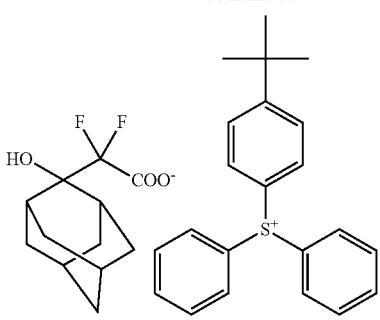
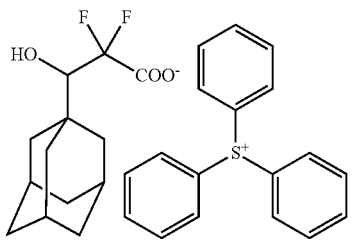
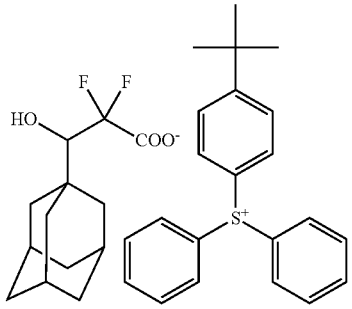
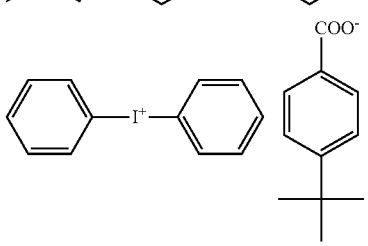
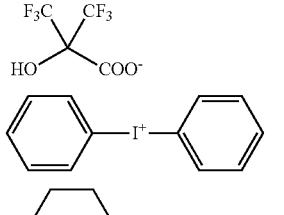
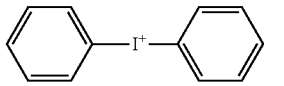
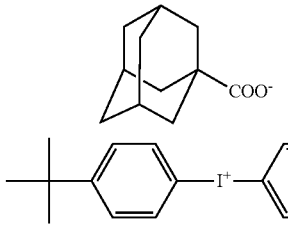

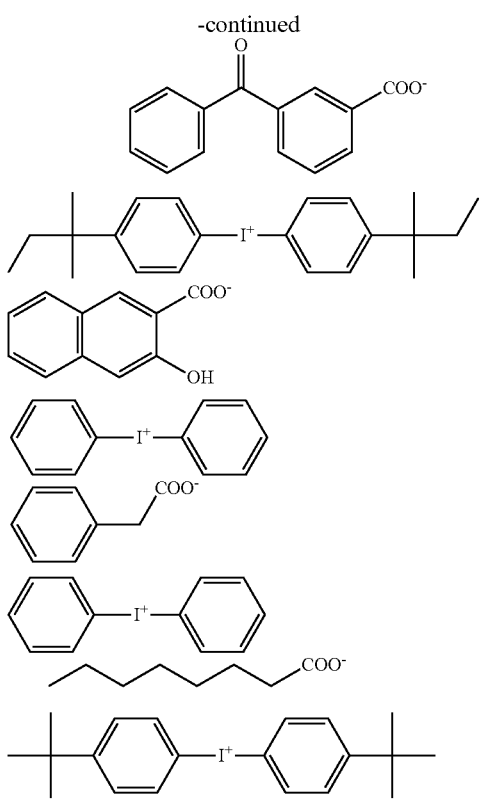

Also an onium salt having a nitrogen-containing substituent group may be used as the quencher. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and 2012-046501, for example.

The quencher (D) may be used alone or in admixture of two or more. An appropriate amount of the quencher is 0 to 50 parts by weight per 100 parts by weight of the base resin (A). When quencher (D) is added, the lower limit is preferably 0.001 part, more preferably 0.01 part by weight, and the upper limit is preferably 40 parts, more preferably 20 parts by weight. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

Component E

The resist composition may further comprise (E) a surfactant which is insoluble or substantially insoluble in water and soluble in alkaline developer, and/or a surfactant which is insoluble or substantially insoluble in water and alkaline developer (hydrophobic resin). For the surfactant (E) which can be added to the resist composition, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflone® S-381, Surfynol® E1004, KH-20 and KH-30, which may be used alone or in admixture. Partially fluorinated oxetane ring-opened polymers having the formula (surf-1) are also useful.

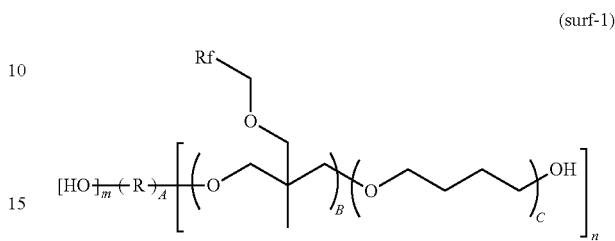

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

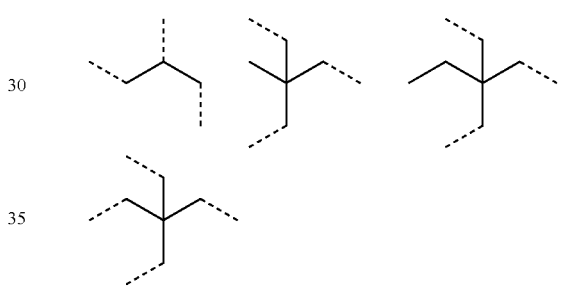

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

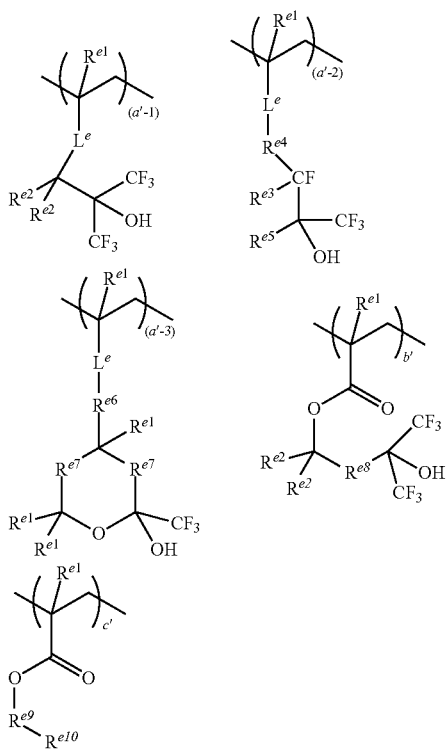

Herein $R^{e1}$ is each independently hydrogen, fluorine, methyl or trifluoromethyl. $R^{e2}$ is each independently hydrogen or a $C_1$-$C_{20}$ straight, branched or cyclic alkyl or fluoroalkyl group, or two $R^{e2}$ in a common monomer may bond together to form a ring with the carbon atom to which they are attached, and in this event, they together represent a $C_2$-$C_{20}$ straight, branched or cyclic alkylene or fluoroalkylene group. $R^3$ is fluorine or hydrogen, or $R^{e3}$ may bond with $R^{e4}$ to form a non-aromatic ring of 3 to 10 carbon atoms in total with the carbon atom to which they are attached. $R^{e4}$ is a $C_1$-$C_6$ straight, branched or cyclic alkylene group in which at least one hydrogen atom may be substituted by a fluorine atom. $R^{e5}$ is a $C_1$-$C_{14}$ straight or branched alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene. $R^{e7}$ is each independently a single bond, —O—, or —$CR^{e1}R^{a1}$—. $R^{e8}$ is a $C_1$-$C_4$ straight or $C_3$-$C_4$ branched alkylene group, or may bond with $R^{e2}$ within a common unit to form a $C_3$-$C_6$ non-aromatic ring with the carbon atom to which they are attached. $R^{e9}$ is a $C_1$-$C_{30}$ divalent hydrocarbon group which may contain a heteroatom. $R^{e10}$ is a linear perfluoroalkyl group of 3 to 6 carbon atoms, typically 3H-perfluoropropyl, 4H-perfluorobutyl, 5H-perfluoropentyl or 6H-perfluorohexyl. L is each independently —C(=O)—O—, —O—, or —C(=O)—$R^{a11}$—C(=O)—O—. $R^{e11}$ is a straight, branched or cyclic $C_1$-$C_{10}$ alkylene group. The subscripts are in the range: $0 \leq (a'-1) \leq 1$, $0 \leq (a'-2) \leq 1$, $0 \leq (a'-3) \leq 1$, $0 \leq b' \leq 1$, $0 \leq c' \leq 1$, and $0 < (a'-1)+(a'-2)+(a'-3)+b'+c' \leq 1$.

Examples of these units are shown below. Herein $R^{a1}$ is as defined above.

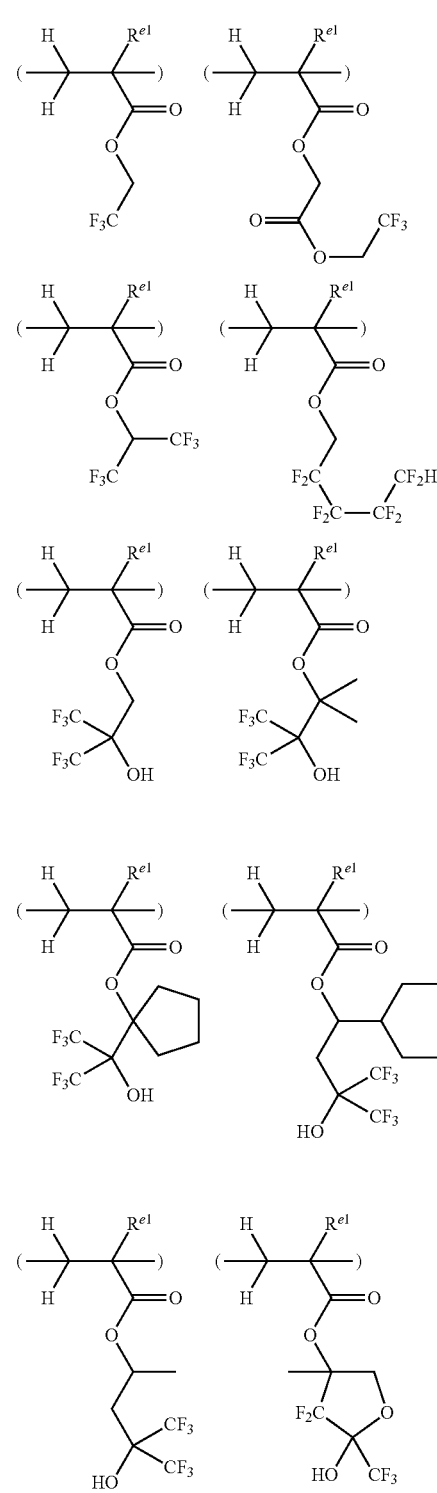

-continued

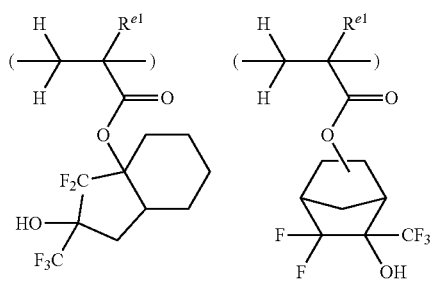
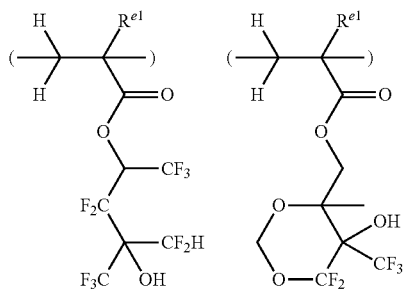
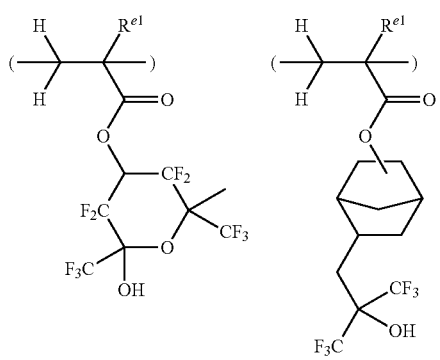
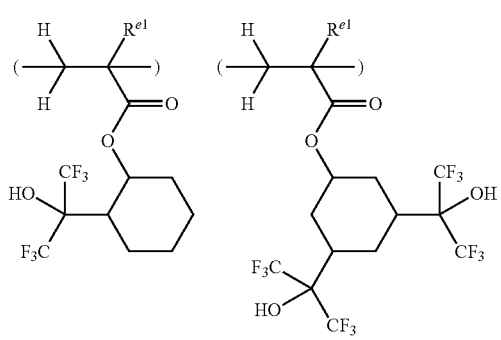
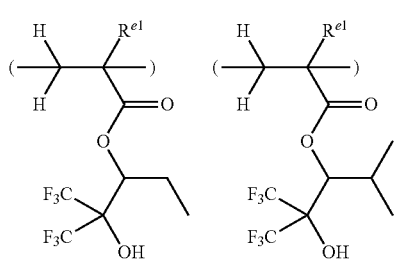

-continued

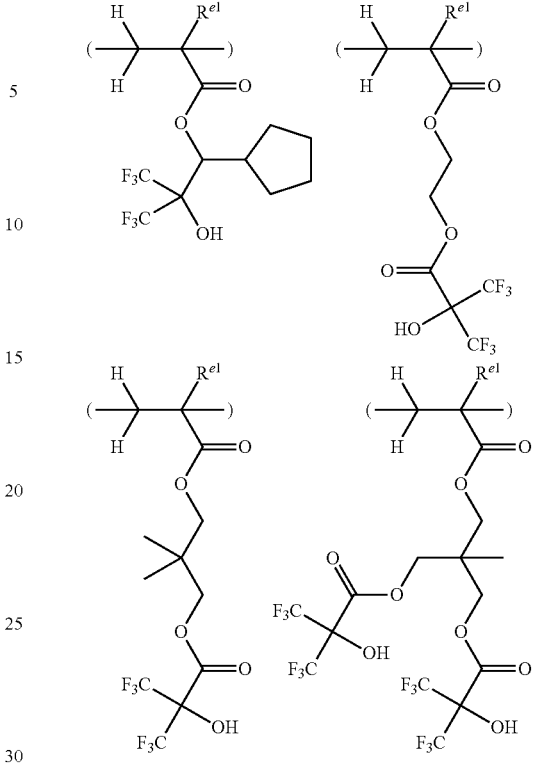

For the surfactant which is insoluble or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

The polymeric surfactant has a Mw of preferably 1,000 to 50,000, more preferably 2,000 to 20,000 as measured by GPC versus polystyrene standards. A surfactant with a Mw within the range may be effective for surface modification and cause few or no development defects.

An appropriate amount of component (E) is 0 to 20 parts by weight per 100 parts by weight of the base resin (A). When component (E) is added, the lower limit is preferably 0.001 part, and more preferably 0.01 part by weight, and the upper limit is preferably 15 parts, more preferably 10 parts by weight.

Other Components F

To the resist composition, a compound which is decomposed with an acid to generate another acid (acid amplifier compound), an organic acid derivative, a fluorinated alcohol, or a compound having a Mw of up to 3,000 which changes its solubility in alkaline developer under the action of an acid (dissolution inhibitor) may be added. For the acid amplifier compound, reference should be made to JP-A 2009-269953 and 2010-215608. In the resist composition, an appropriate amount of the acid amplifier compound is 0 to 5 parts, and especially 0 to 3 parts by weight per 100 parts by weight of the base resin (A). Excessive amounts of the acid amplifier compound make diffusion control difficult, leading to degradation of resolution and pattern profile. With respect to the organic acid derivative, fluorinated alcohol, and dissolution inhibitor, reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of applying the resist composition onto a substrate, prebaking to form a resist film, exposing a selected region of the resist film to high-energy radiation, PEB and developing the resist film in a developer to form a resist pattern. Several steps may be added if necessary.

The process of forming a positive resist pattern using an alkaline aqueous solution as the developer may be carried out with reference to U.S. Pat. No. 8,647,808 (JP-A 2011-231312, paragraphs [0138]-[0146]).

The process of forming a negative resist pattern using an organic solvent as the developer is described with reference to FIG. 1. First, the resist composition is coated on a substrate to form a resist film thereon. Specifically, a resist film 40 of a resist composition is formed on a processable layer 20 disposed on a substrate 10 directly or via an intermediate intervening layer 30 as shown in FIG. 1A. The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 600 seconds, especially 15 to 300 seconds.

The substrate 10 used herein is generally a silicon substrate. The processable layer (or target film) 20 used herein includes $SiO_2$, SiN, SiON, SiOC, p-Si, $\alpha$-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Next comes exposure depicted at 50 in FIG. 1B. In the exposure step, a photomask may be used if necessary. For the exposure, preference is given to high-energy radiation having a wavelength of 140 to 250 nm, EUV having a wavelength of 13.5 nm, and EB, and especially ArF excimer laser radiation of 193 nm. The exposure may be done either in a dry atmosphere such as air or nitrogen stream or by immersion lithography.

The immersion lithography uses deionized water or liquids having a refractive index of at least 1 and highly transparent to the exposure wavelength such as alkanes as the immersion solvent. In the immersion lithography, the resist film as prebaked is exposed to light through a projection lens while the liquid, typically water is introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer which is soluble in the developer, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue, for example. While the protective film must dissolve in the organic solvent developer, the polymer comprising recurring units having a 1,1,1,3,3,3-hexafluoro-2-propanol residue dissolves in organic solvent developers. In particular, protective film-forming polymers having 1,1,1,3,3,3-hexafluoro-2-propanol residues as described in JP-A 2007-025634, JP-A 2008-003569, JP-A 2008-081716 and JP-A 2008-111089 readily dissolve in organic solvent developers.

In the protective film-forming composition, an amine compound or amine salt may be added, or a polymer comprising recurring units containing an amino group or amine salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful polymers comprising recurring units having an amino group or amine salt are described in JP-A 2007-316448. The amine compound or amine salt may be selected from the compounds enumerated above as quencher (D). An appropriate amount of the amine compound or amine salt added is preferably 0.01 to 10 parts, more preferably 0.02 to 8 parts by weight per 100 parts by weight of the base resin (A).

After formation of the resist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface edges of holes or lines of a hole or line-and-space pattern after development are bridged. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

With respect to the recurring units having a 1,1,1,3,3,3-hexafluoro-2-propanol residue, those monomers having a —C(CF$_3$)(OH) group, i.e., a carbon atom having CF$_3$ and OH radicals bonded thereto are preferably selected among the exemplary monomers listed for the polymeric surfactant. The amino group-containing compound may be selected from the exemplary amine compounds described in JP-A 2008-111103, paragraphs [0146]-[0164]. As the amine salt-containing compound, salts of the foregoing amine compounds with carboxylic acid or sulfonic acid may be used.

The solvent in the protective film-forming composition is preferably selected from alcohols of at least 4 carbon atoms, ethers of 8 to 12 carbon atoms, and mixtures thereof. Suitable alcohols of at least 4 carbon atoms include 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether.

Exposure is preferably performed in an exposure dose of about 1 to 200 mJ/cm$^2$, more preferably about 10 to 100 mJ/cm$^2$. This is followed by baking (PEB) on a hot plate at 60 to 150° C. for 1 to 5 minutes, preferably at 80 to 140° C. for 1 to 3 minutes.

Thereafter the exposed resist film is developed in an organic solvent base developer for 0.1 to 3 minutes, preferably 0.5 to 2 minutes by any conventional techniques such as dip, puddle and spray techniques. In this way, the unexposed region of resist film is dissolved away, leaving a negative resist pattern 40 on the substrate 10 as shown in FIG. 1C.

The developer used herein is based on an organic solvent which is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

These solvents may be used alone or in admixture of two or more. The organic solvent or solvents are preferably present in a total amount of at least 60% by weight of the developer. More preferably the organic solvent(s) accounts for 80 to 100% by weight of the developer. A surfactant may be added to the developer while it may be selected from the same list of compounds as exemplified for the surfactant to be added to the resist composition. The surfactant is preferably added in an amount of 0 to 5%, more preferably 0 to 3% by weight of the developer.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. The solvents may be used alone or in admixture. Besides the foregoing solvents, aromatic solvents may be used, for example, toluene, xylene, ethylbenzene, isopropylbenzene, t-butylbenzene and mesitylene.

While rinsing is effective for mitigating collapse and defect formation in the resist pattern, rinsing is not essential. If the rinsing step is omitted, the amount of solvent used in the process may be reduced.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

In another embodiment, the hole pattern printed as the reversal pattern may be shrunk by the RELACS method. A shrink agent is coated on the hole pattern and baked. During bake, the acid catalyst diffuses from the resist layer to promote crosslinking of the shrink agent on the resist surface so that the shrink agent is attached to side walls of the hole pattern. The baking is preferably at a temperature of 70 to 180° C., more preferably 80 to 170° C. for a time of 10 to 300 seconds. Then the extra shrink agent is removed, and the hole pattern is reduced.

EXAMPLE

Examples and Comparative Examples are given below by way of illustration and not by way of limitation. The abbreviation "pbw" is parts by weight. For all polymers, Mw and Mn are determined by GPC versus polystyrene standards using tetrahydrofuran solvent. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.

1) Synthesis of Monomers

Example 1-1

Synthesis of PAG-1
PAG-1 was synthesized according to the following scheme.

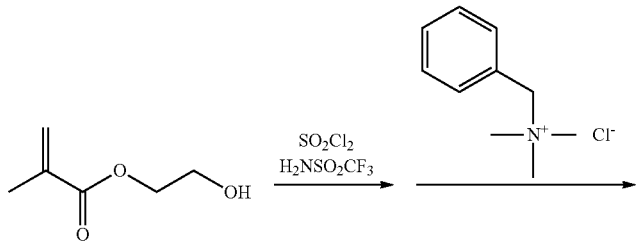

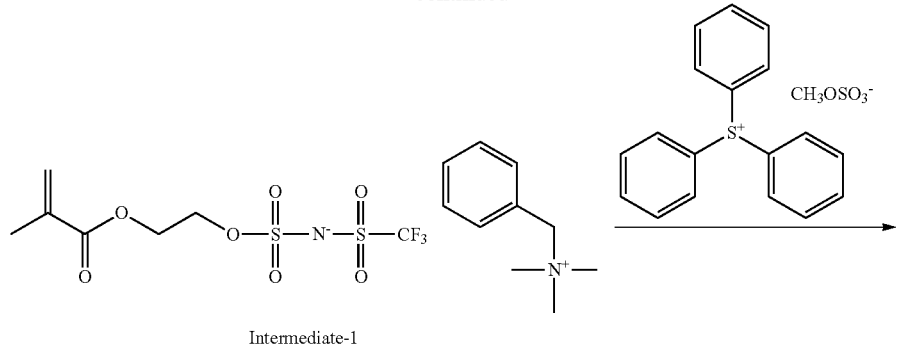

Intermediate-1

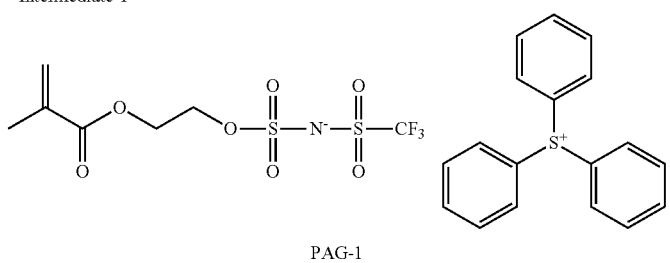

PAG-1

(1) Synthesis of Intermediate 1

Under ice cooling, a solution of 20.87 g of trifluoromethanesulfonamide and 38.76 g of pyridine in 70 g of acetonitrile was added dropwise to a mixture of 18.90 g of sulfuryl chloride and 70 g of acetonitrile. The reaction solution was warmed at room temperature, stirred for 90 minutes for aging, and ice cooled. Under ice cooling, a solution of 27.33 g of 2-hydroxyethyl methacrylate and 1.71 g of 4-dimethylaminopyridine in 140 g of acetonitrile was added dropwise to the reaction solution. The reaction solution was heated at 50° C. and stirred for 15 hours. Methanol, 10 g, was added to the reaction solution, which was stirred at 50° C. for 4 hours for aging and quenched. The reaction solution was cooled at room temperature, to which 560 g of methyl isobutyl ketone (MIBK) and 420 g of water were added. The organic layer was taken out and washed with 280 g of water, after which 26.00 g of benzyltrimethylammonium chloride and 280 g of water were added thereto. The mixture was stirred for 30 minutes. The organic layer was taken out, washed 3 times with 280 g of 2 wt % benzyltrimethylammonium chloride aqueous solution and twice with 280 g of water, and concentrated in vacuum. Steps of adding 200 g of diisopropyl ether to the concentrate, stirring for 5 minutes, and removing a supernatant were repeated five times. The residue was concentrated in vacuum, obtaining 39.3 g of the target Intermediate 1 as oily matter (yield 55%). Analytic results by IR, $^1$H-NMR and $^{19}$F-NMR are shown below.

IR (D-ATR):

ν=3039, 2960, 1717, 1637, 1490, 1479, 1457, 1368, 1338, 1321, 1186, 1142, 1070, 1032, 956, 923, 890, 802, 781, 762, 727, 703, 638, 610, 605, 569 cm$^{-1}$ $^1$H-NMR (500 MHz, DMSO-d$_6$):

δ=1.87 (3H, m), 3.01 (9H, s), 4.20 (2H, m), 4.29 (2H, m), 4.50 (2H, s), 5.69 (1H, m), 6.06 (1H, m), 7.51-7.56 (5H, m) ppm $^{19}$F-NMR (500 MHz, DMSO-d$_6$): δ=−78.9 (3F, s) ppm (2) Synthesis of PAG-1

Intermediate 1, 22.00 g, and 18.74 g of triphenylsulfonium methylsulfate were dissolved in a mixture of 200 g of dichloromethane and 100 g of water and stirred at room temperature for 20 minutes. The organic layer was taken out and washed 5 times with 100 g of water. The organic layer was concentrated in vacuum. Steps of adding 150 g of diisopropyl ether, stirring for 5 minutes and removing a supernatant were repeated twice. The residue was concentrated in vacuum, obtaining 22.66 g of the target PAG-1 as oily matter (yield 85%). Analytic results by $^1$H-NMR and $^{19}$F-NMR are shown below.

$^1$H-NMR (500 MHz, DMSO-d):

δ=1.87 (3H, m), 4.20 (2H, m), 4.29 (2H, m), 5.69 (1H, m), 6.06 (1H, m), 7.75-7.83 (15H, m) ppm $^{19}$F-NMR (500 MHz, DMSO-d$_6$): δ=−78.9 (3F, s) ppm Examples 1-2 to 1-7

Synthesis of PAG-2 to PAG-7

Monomers PAG-2 to PAG-7 were synthesized by the same procedure as in Example 1-1 aside from changing the type of reactants (sulfonamide and alcohol).

PAG-2

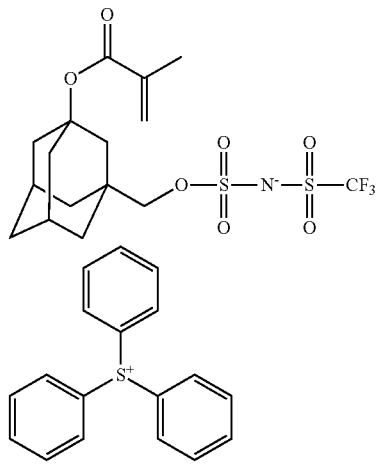

-continued

PAG-3

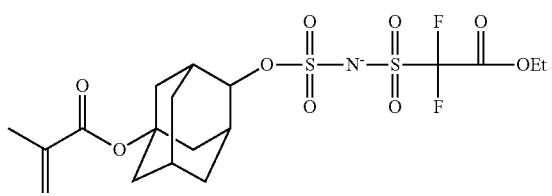

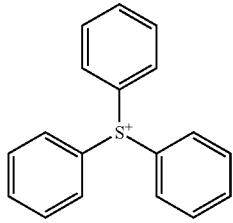

PAG-4

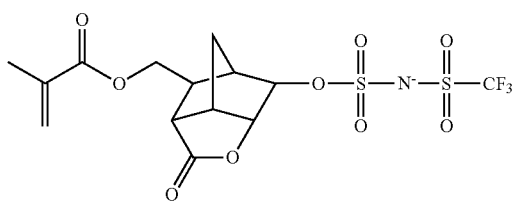

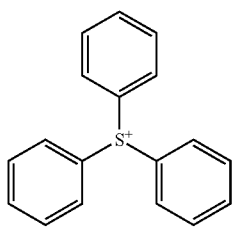

PAG-5

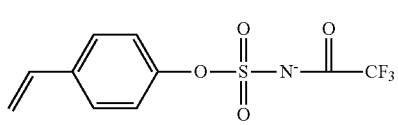

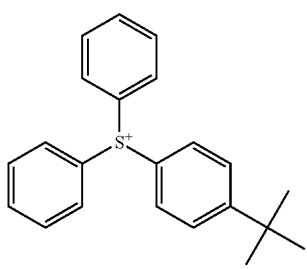

PAG-6

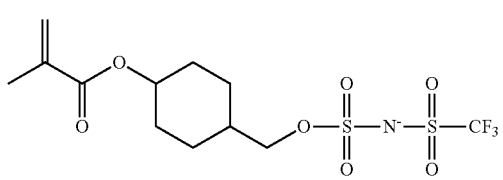

-continued

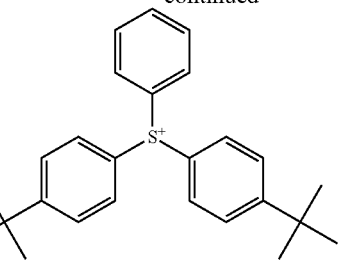

PAG-7

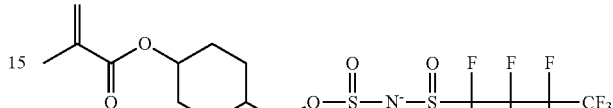

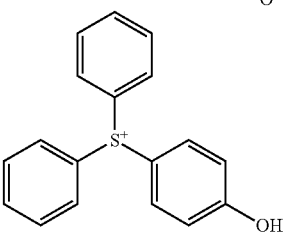

2) Synthesis of Base Resin

Example 2-1

Synthesis of Polymer P-1

In a flask under nitrogen atmosphere, 25.1 g of PAG-1, 43.8 g of 1-t-butylcyclopentyl methacrylate, 9.8 g of 3-hydroxyadamantyl-1-yl methacrylate, 21.3 g of 2-oxotetrahydrofuran-3-yl methacrylate, 4.79 g of dimethyl 2,2'-azobis (isobutyrate), and 175 g of methyl ethyl ketone (MEK) were combined to form a monomer solution. Another flask in nitrogen atmosphere was charged with 58 g of MEK, which was heated at 80° C. with stirring. With stirring, the monomer solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to a mixture of 100 g of MEK and 900 g of hexane. The precipitated copolymer was collected by filtration, washed twice with 600 g of hexane, and vacuum dried at 50° C. for 20 hours, obtaining Polymer P-1 in white powder solid form. Amount 91.2 g, yield 91%. The composition of Polymer 1 is shown in Table 1.

Examples 2-2 to 2-8

Synthesis of Polymers P-2 to P-8

Polymers P-2 to P-8 and Comparative Polymers P-9 to P-15 were synthesized by the same procedure as in Example 2-1 aside from changing the type and amount of monomers.

Table 1 shows the proportion (in molar ratio) of units incorporated in these polymers. The structure of recurring units is shown in Tables 2 to 4.

TABLE 1
| Polymer | Unit 1 (molar ratio) | Unit 2 (molar ratio) | Unit 3 (molar ratio) | Unit 4 (molar ratio) | Unit 5 (molar ratio) | Mw | Mw/Mn |
|---|---|---|---|---|---|---|---|
| P-1 | PAG-1 (0.10) | A-1 (0.50) | B-1 (0.30) | B-4 (0.10) | — | 9,200 | 1.57 |
| P-2 | PAG-1 (0.10) | A-1 (0.30) | A-2 (0.20) | B-1 (0.30) | B-4 (0.10) | 8,800 | 1.57 |
| P-3 | PAG-2 (0.10) | A-1 (0.50) | B-1 (0.30) | B-4 (0.10) | — | 8,900 | 1.60 |
| P-4 | PAG-3 (0.10) | A-1 (0.35) | A-2 (0.15) | B-2 (0.30) | B-4 (0.10) | 8,500 | 1.59 |
| P-5 | PAG-4 (0.10) | A-2 (0.30) | A-4 (0.20) | B-2 (0.20) | B-3 (0.20) | 9,100 | 1.57 |
| P-6 | PAG-5 (0.10) | A-1 (0.30) | A-3 (0.20) | B-3 (0.40) | — | 8,500 | 1.58 |
| P-7 | PAG-6 (0.10) | A-1 (0.50) | B-2 (0.20) | B-3 (0.20) | — | 8,800 | 1.60 |
| P-8 | PAG-7 (0.10) | A-2 (0.35) | A-4 (0.15) | B-2 (0.30) | B-3 (0.10) | 9,000 | 1.59 |
| P-9 | C-1 (0.10) | A-1 (0.50) | B-1 (0.30) | B-4 (0.10) | — | 8,900 | 1.58 |
| P-10 | C-2 (0.10) | A-1 (0.50) | B-1 (0.30) | B-4 (0.10) | — | 8,300 | 1.53 |
| P-11 | C-3 (0.10) | A-1 (0.50) | B-1 (0.30) | B-4 (0-10) | — | 9,300 | 1.61 |
| P-12 | C-4 (0.10) | A-1 (0.50) | B-1 (0.30) | B-4 (0.10) | — | 8,600 | 1.59 |
| P-13 | C-5 (0.10) | A-1 (0.50) | B-1 (0.30) | B-4 (0.10) | — | 8,600 | 1.56 |
| P-14 | C-6 (0.10) | A-1 (0.50) | B-1 (0.30) | B-4 (0.10) | — | 8,800 | 1.59 |
| P-15 | A-1 (0.50) | B-1 (0.30) | B-3 (0.10) | B-4 (0.10) | — | 9,100 | 1.57 |
TABLE 2
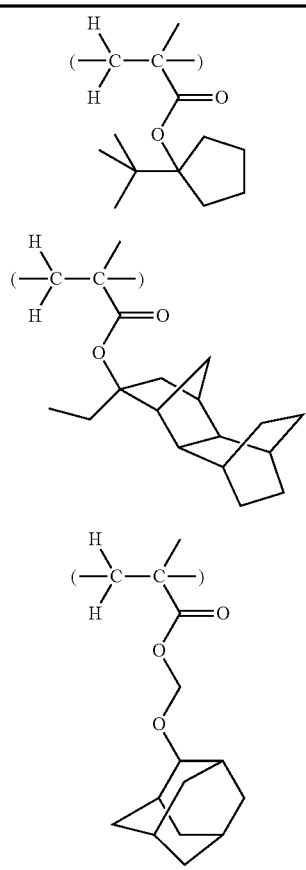
A-1
A-2
A-3
TABLE 2-continued
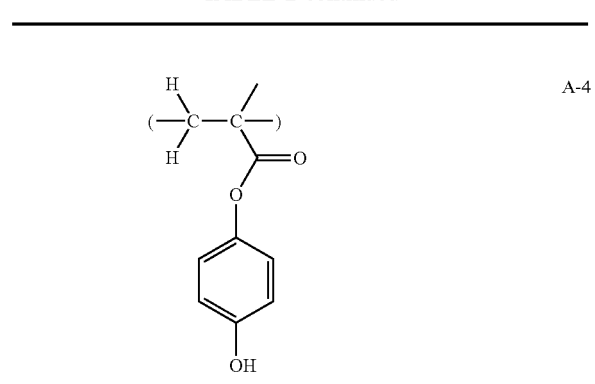
A-4
TABLE 3
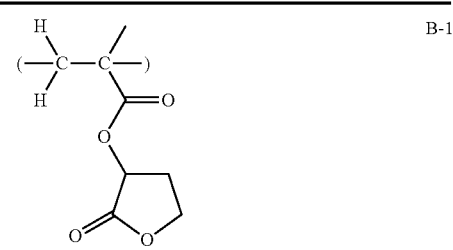
B-1
B-2
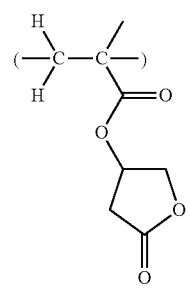
B-3
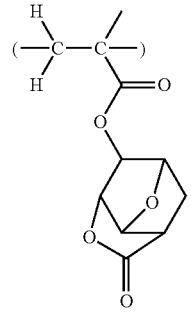
B-4
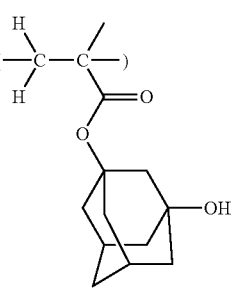

TABLE 4

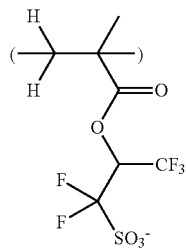 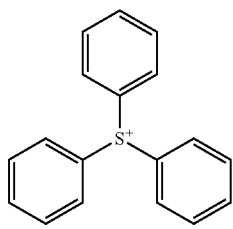 C-1

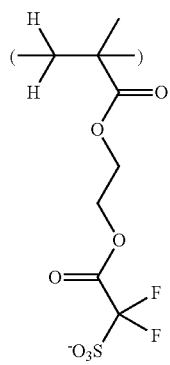 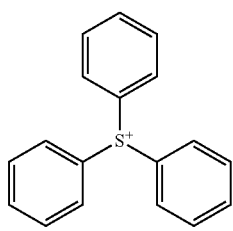 C-2

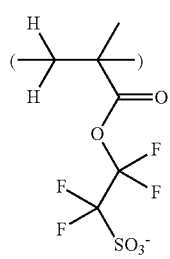 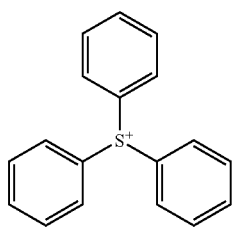 C-3

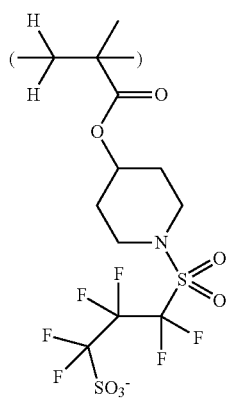 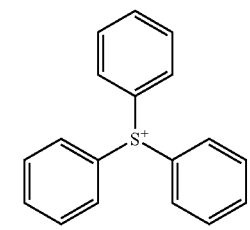 C-4

TABLE 4-continued

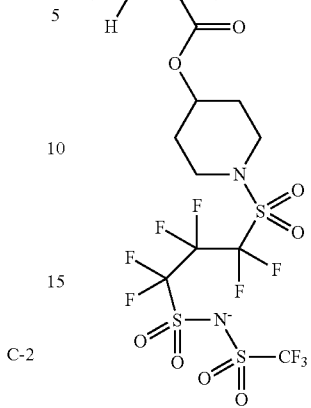 C-5

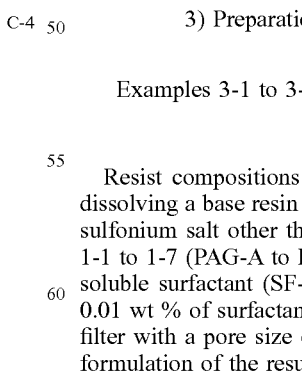 C-6

3) Preparation of Resist Composition

Examples 3-1 to 3-8 & Comparative Examples 1-1 to 1-7

Resist compositions in solution form were prepared by dissolving a base resin (Polymers P-1 to P-15), optionally a sulfonium salt other than the sulfonium salts of Examples 1-1 to 1-7 (PAG-A to PAG-C), quencher (Q-1), and alkali-soluble surfactant (SF-1) in an organic solvent containing 0.01 wt % of surfactant A, and filtering through a Teflon® filter with a pore size of 0.2 μm. Tables 5 and 6 show the formulation of the resulting resist compositions.

The solvent, quencher (Q-1), sulfonium salt other than the above-synthesized sulfonium salts (PAG-A to PAG-C), alkali-soluble surfactant (SF-1) and surfactant A used herein are identified below.

Quencher (Q-1):
   2-(4-morpholinyl)ethyl octadecanoate

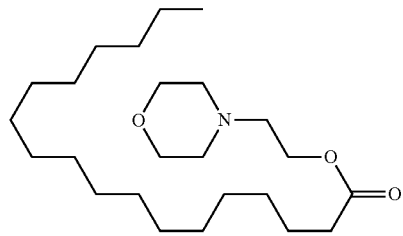

Solvent:
   PGMEA: propylene glycol monomethyl ether acetate
   GBL: γ-butyrolactone Other Photoacid Generators:
   PAG-A: triphenylsulfonium 2-(adamantane-1-carbonyloxy)-3,3,3-trifluoro-2-trifluoromethylpropane-1-sulfonate (described in JP-A 2010-215608)

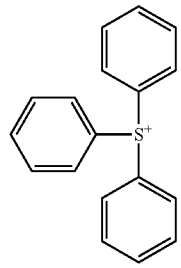 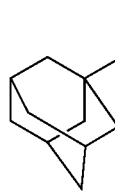

(PAG-A)

PAG-B: triphenylsulfonium 2-(adamantane-1-carbonyloxy)-ethanesulfonate (described in JP-A 2010-155824)

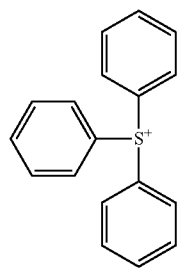 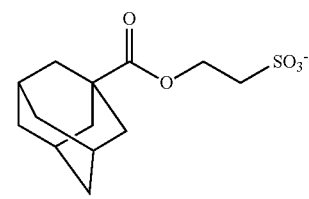

(PAG-B)

PAG-C: triphenylsulfonium bis(trifluoromethanesulfonyl)-imide

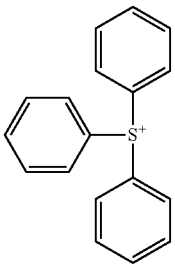 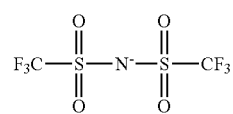

(PAG-C)

Alkali-Soluble Surfactant (SF-1):
   poly(2,2,3,3,4,4,4-heptafluoro-1-isobutyl-1-butyl methacrylate/9-(2,2,2-trifluoro-1-trifluoroethyloxy-carbonyl)-4-oxatricyclo[4.2.1.$^{3,7}$]nonan-5-on-2-yl methacrylate)
   Mw=7,700
   Mw/Mn=1.82

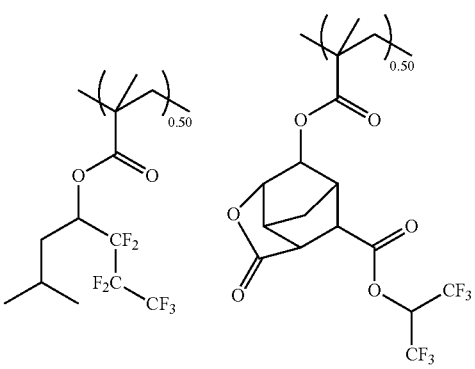

(SF-1)

Surfactant A:
   3-methyl-3-(2,2,2-trifluoroethoxymethyl)oxetane/tetrahydrofuran/2,2-dimethyl-1,3-propanediol copolymer (Omnova Solutions, Inc.)

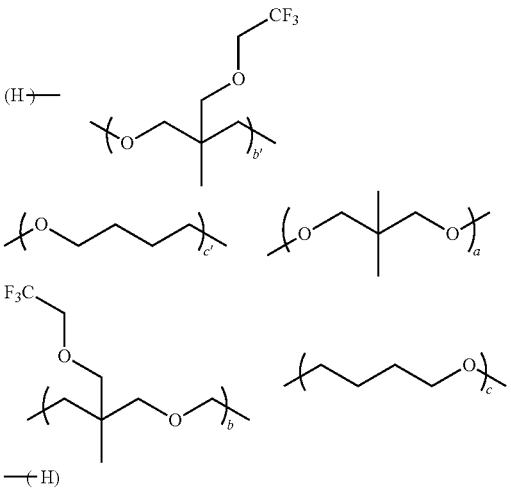

a:(b+b'):(c+c')=1:4-7:0.01-1 (molar ratio)
MW=1,500

TABLE 5

| Resist composition | | Resin (pbw) | Acid generator (pbw) | Quencher (pbw) | Surfactant (pbw) | Solvent 1 (pbw) | Solvent 2 (pbw) |
|---|---|---|---|---|---|---|---|
| Example | 3-1 | R-1 (80) | P-1 PAG-B (2.0) | — | SF-1 (3.0) | PGMEA (1,536) | GBL (384) |
| | 3-2 | R-2 (80) | P-2 PAG-A (2.0) | Q-1 (1.0) | SF-1 (3.0) | PGMEA (1,536) | GBL (384) |
| | 3-3 | R-3 (80) | P-3 PAG-B (2.0) | — | SF-1 (3.0) | PGMEA (1,536) | GBL (384) |
| | 3-4 | R-4 (80) | P-4 PAG-A (2.0) | Q-1 (1.0) | SF-1 (3.0) | PGMEA (1,536) | GBL (384) |
| | 3-5 | R-5 (80) | P-5 — | Q-1 (0.5) | SF-1 (3.0) | PGMEA (1,536) | GBL (384) |
| | 3-6 | R-6 (80) | P-6 PAG-A (2.0) PAG-B (1.0) | — | SF-1 (3.0) | PGMEA (1,536) | GBL (384) |
| | 3-7 | R-7 (80) | P-7 — | Q-1 (1.0) | SF-1 (3.0) | PGMEA (1,536) | GBL (384) |
| | 3-8 | R-8 (80) | P-8 PAG-A (1.5) PAG-B (1.5) | Q-1 (0.5) | SF-1 (3.0) | PGMEA (1,536) | GBL (384) |

TABLE 6

| Resist composition | | Resin (pbw) | Acid generator (pbw) | Quencher (pbw) | Surfactant (pbw) | Solvent 1 (pbw) | Solvent 2 (pbw) |
|---|---|---|---|---|---|---|---|
| Comparative Example | 1-1 | R-9 (80) | P-9 PAG-B (2.0) | — | SF-1 (3.0) | PGMEA (1,536) | GBL (384) |
| | 1-2 | R-10 (80) | P-10 PAG-B (2.0) | — | SF-1 (3.0) | PGMEA (1,536) | GBL (384) |
| | 1-3 | R-11 (80) | P-11 PAG-B (2.0) | — | SF-1 (3.0) | PGMEA (1,539) | GBL (384) |
| | 1-4 | R-12 (80) | P-12 PAG-B (2.0) | — | SF-1 (3.0) | PGMEA (1,536) | GBL (384) |
| | 1-5 | R-13 (80) | P-13 PAG-B (2.0) | — | SF-1 (3.0) | PGMEA (1,536) | GBL (384) |
| | 1-6 | R-14 (80) | P-14 PAG-B (2.0) | — | SF-1 (3.0) | PGMEA (1,536) | GBL (384) |
| | 1-7 | R-15 (80) | P-15 PAG-C (6.0) PAG-B (2.0) | — | SF-1 (3.0) | PGMEA (1,536) | GBL (384) |

4) ArF Lithography Patterning Test #1

Evaluation of Hole Pattern

Examples 4-1 to 4-8 and Comparative Examples 2-1 to 2-7

On a substrate, a spin-on carbon film ODL-50 (Shin-Etsu Chemical Co., Ltd.) having a carbon content of 80 wt % was deposited to a thickness of 200 nm, and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-8 or Comparative R-9 to R-15) was spin coated and baked on a hot plate at 100° C. for 60 seconds to form a resist film of 100 nm thick.

Using an ArF excimer laser immersion lithography stepper (NSR-610C by Nikon Corp., NA 1.30, σ 0.98/0.78, dipole opening 20 deg., azimuthally polarized illumination, dipole illumination, 6% halftone phase shift mask), the resist film was exposed through a first mask having X-axis direction lines with a pitch of 80 nm and a width of 40 nm (on-wafer size) and then through a second mask having Y-axis direction lines with a pitch of 80 nm and a width of 40 nm (on-wafer size). After exposure, the resist film was baked (PEB) at the temperature shown in Table 7 for 60 seconds and developed. Specifically, butyl acetate was injected from a development nozzle for 3 seconds while the wafer was spun at 30 rpm, which was followed by stationary puddle development for 27 seconds.

Evaluation of Sensitivity

The resist pattern thus formed was observed under an electron microscope. The optimum dose (Eop) is a dose (mJ/cm$^2$) which provides a hole pattern having a diameter of 40 nm at a pitch of 80 nm.

Evaluation of Mask Error Factor (MEF)

A pattern was formed by exposure in the optimum dose (determined in the sensitivity evaluation) through a mask with the pitch fixed and the line width varied. MEF was calculated from variations of the mask line width and the pattern space width according to the following equation:

$$MEF = (\text{pattern space width})/(\text{mask line width}) - b$$

wherein b is a constant. A value closer to unity (1) indicates better performance.

Evaluation of Critical Dimension Uniformity (CDU)

The hole pattern printed as above was observed under TD-SEM (CG-4000 by Hitachi Hitechnologies, Ltd.), and 125 holes were measured for diameter. A three-fold value (3σ) of a standard variation (σ) was computed therefrom as a variation of hole size and reported as CDU. A smaller value (3σ) indicates a smaller variation of hole size.

Evaluation of Defect Density

Further, defects in the pattern as developed were inspected by a flaw detector KLA2800 (KLA-Tencor). A defect density (count/cm$^2$) was computed by dividing the total number of detected defects by a detection area. The pattern formed was an iterated 40-nm 1:1 hole pattern. The defect inspection conditions included light source UV, inspected pixel size 0.28 μm, and cell-to-cell mode. In this test, the sample was rated good for a defect density of less than 0.05 defect/cm$^2$ and NG for a density of equal to or more than 0.05 defect/cm$^2$.

The results are shown in Table 7.

TABLE 7

|  |  | Resist composition | PEB temp. (° C.) | Eop (mJ/cm$^2$) | MEF | CDU | Defect density |
|---|---|---|---|---|---|---|---|
| Example | 4-1 | R-1 | 85 | 30 | 2.45 | 3.3 | good |
|  | 4-2 | R-2 | 90 | 34 | 2.88 | 3.3 | good |
|  | 4-3 | R-3 | 85 | 35 | 2.90 | 3.5 | good |
|  | 4-4 | R-4 | 90 | 29 | 2.67 | 3.2 | good |
|  | 4-5 | R-5 | 95 | 37 | 2.70 | 3.6 | good |
|  | 4-6 | R-6 | 85 | 35 | 2.66 | 3.7 | good |
|  | 4-7 | R-7 | 85 | 30 | 3.01 | 3.4 | good |
|  | 4-8 | R-8 | 90 | 29 | 3.15 | 3.6 | good |
| Comparative Example | 2-1 | R-9 | 85 | 47 | 3.89 | 4.2 | NG |
|  | 2-2 | R-10 | 85 | 51 | 3.75 | 4.3 | NG |
|  | 2-3 | R-11 | 85 | 25 | 3.90 | 4.4 | NG |
|  | 2-4 | R-12 | 85 | 44 | 4.12 | 4.1 | NG |
|  | 2-5 | R-13 | 85 | 29 | 3.84 | 4.2 | NG |
|  | 2-6 | R-14 | 85 | 39 | 3.50 | 3.9 | good |
|  | 2-7 | R-15 | 85 | 40 | 4.44 | 4.0 | good |

It is evident from Table 7 that when the inventive resist composition is processed by lithography and organic solvent development, a negative pattern with a good balance of sensitivity, MEF and CDU is formed. The number of defects after development is small. It is demonstrated that the resist composition within the scope of the invention is effective in the organic solvent development process.

5) ArF Lithography Patterning Test #2

Evaluation of L/S Pattern

Examples 5-1 to 5-8 and Comparative Examples 3-1 to 3-7

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-8 or Comparative R-9 to R-15) was spin coated and baked on a hot plate at 100° C. for 60 seconds to form a resist film of 100 nm thick.

Using an ArF excimer laser immersion lithography scanner NSR-610C (Nikon Corp., NA 1.30, σ 0.98/0.78, 4/5 annular illumination), pattern exposure was performed through a 6% halftone phase shift mask bearing a pattern with a pitch of 100 nm and a space width of 50 nm (on-wafer size). After exposure, the wafer was baked (PEB) at the temperature shown in Table 8 for 60 seconds and developed. Specifically, 2.38 wt % tetramethylammonium hydroxide aqueous solution was injected from a development nozzle for 3 seconds while the wafer was spun at 30 rpm, which was followed by stationary puddle development for 27 seconds. As a result, the exposed regions of the resist film were dissolved in the developer to form a line-and-space (L/S) pattern with a space width of 50 nm and a pitch of 100 nm.

Evaluation of Sensitivity

As an index of sensitivity, the optimum dose (Eop, mJ/cm$^2$) which provided a L/S pattern with a space width of 50 nm and a pitch of 100 nm on exposure through the mask was determined. A smaller value indicates a higher sensitivity.

Evaluation of MEF

A L/S pattern was formed by exposure in the optimum dose (determined in the sensitivity evaluation) through the mask with the pitch fixed and the line width varied. MEF was calculated from variations of the mask line width and the pattern space width according to the following equation:

$$MEF=(\text{pattern space width})/(\text{mask line width})-b$$

wherein b is a constant. A value closer to unity (1) indicates better performance.

Evaluation of Line Width Roughness (LWR)

The L/S pattern printed in the optimum dose in ArF lithography patterning test #1 was observed under TD-SEM (S-9380 by Hitachi Hitechnologies, Ltd.) and ten longitudinally spaced apart spaces were measured for width. A three-fold value (3σ) of a standard variation (σ) was computed therefrom and reported as LWR. A smaller value (3σ) indicates a smaller roughness and hence, a pattern of more uniform space width.

The results are shown in Table 8.

TABLE 8

|  |  | Resist composition | PEB temp. (° C.) | Eop (mJ/cm$^2$) | MEF | LWR | Pattern profile |
|---|---|---|---|---|---|---|---|
| Example | 5-1 | R-1 | 85 | 35 | 2.56 | 3.1 | rectangular |
|  | 5-2 | R-2 | 85 | 30 | 2.98 | 3.2 | rectangular |
|  | 5-3 | R-3 | 85 | 34 | 2.77 | 3.1 | rectangular |
|  | 5-4 | R-4 | 85 | 28 | 2.64 | 3.0 | rectangular |
|  | 5-5 | R-5 | 85 | 28 | 2.59 | 3.4 | rectangular |
|  | 5-6 | R-6 | 90 | 36 | 2.66 | 3.1 | rectangular |
|  | 5-7 | R-7 | 90 | 28 | 3.14 | 3.0 | rectangular |
|  | 5-8 | R-8 | 90 | 27 | 3.44 | 3.3 | rectangular |
| Comparative Example | 3-1 | R-9 | 85 | 45 | 4.12 | 3.8 | poor |
|  | 3-2 | R-10 | 85 | 49 | 4.44 | 3.9 | poor |
|  | 3-3 | R-11 | 85 | 24 | 4.12 | 4.1 | poor |
|  | 3-4 | R-12 | 85 | 41 | 4.10 | 4.0 | poor |
|  | 3-5 | R-13 | 85 | 27 | 3.99 | 4.3 | poor |
|  | 3-6 | R-14 | 85 | 40 | 3.52 | 4.1 | poor |
|  | 3-7 | R-15 | 85 | 32 | 4.51 | 4.5 | poor |

It is evident from Table 8 that when the inventive resist composition is processed by lithography and alkaline solvent development, a positive pattern with a good balance of sensitivity, MEF and LWR is formed. The pattern has a satisfactory profile. It is demonstrated that the resist composition within the scope of the invention is effective in the alkaline solvent development process.

Japanese Patent Application No. 2016-080899 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the formula (1):

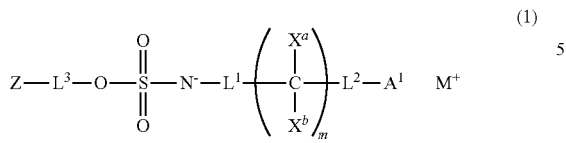
(1)

wherein Z is a polymerizable group, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond, $L^3$ is a single bond or a $C_1$-$C_{40}$ straight, branched or cyclic divalent hydrocarbon group which may contain a heteroatom, $A^1$ is hydrogen, halogen or a $C_{1-20}$ straight, branched or cyclic monovalent hydrocarbon group which may contain a heteroatom, $X^a$ and $X^b$ are each independently hydrogen, fluorine or trifluoromethyl, with the proviso that at least one of $X^a$ and $X^b$ is a substituent group other than hydrogen, m is an integer of 1 to 4, and $M^+$ is an onium cation.

2. The monomer of claim 1 wherein Z is a group having the formula (2) or (3):

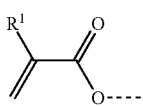
(2)

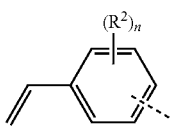
(3)

wherein $R^1$ is hydrogen, methyl, fluorine or trifluoromethyl, $R^2$ is a $C_1$-$C_{12}$ straight, branched or cyclic monovalent hydrocarbon group which may contain a heteroatom, where there are present a plurality of $R^2$, they may be the same or different and they may bond together to form a ring with carbon atoms on the benzene ring, n is an integer of 0 to 4, and the broken line designates a valence bond to $L^3$ in formula (1).

3. The monomer of claim 1 wherein $L^1$ is a sulfonyl bond.

4. The monomer of claim 1 wherein $L^2$ is a single bond and $A^1$ is hydrogen, fluorine or trifluoromethyl.

5. A polymer comprising recurring units derived from the monomer of claim 1.

6. A polymer comprising recurring units having the formula (4) or (5):

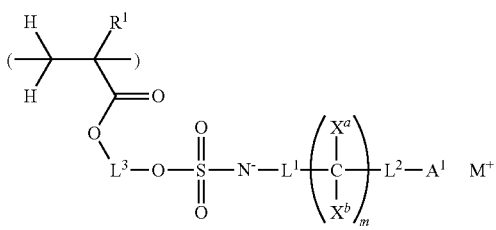
(4)

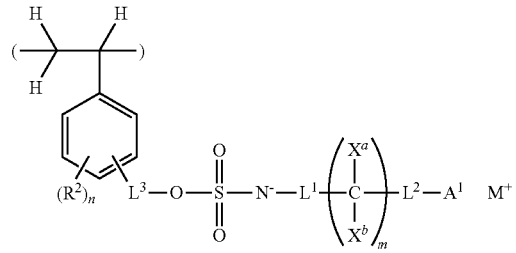
(5)

wherein $R^1$ is hydrogen, methyl, fluorine or trifluoromethyl, $R^2$ is a $C_1$-$C_{12}$ straight, branched or cyclic monovalent hydrocarbon group which may contain a heteroatom, where there are present a plurality of $R^2$, they may be the same or different and they may bond together to form a ring with carbon atoms on the benzene ring, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond, $L^3$ is a single bond or a $C_1$-$C_{40}$ straight, branched or cyclic divalent hydrocarbon group which may contain a heteroatom, $A^1$ is hydrogen, halogen or a $C_1$-$C_{20}$ straight, branched or cyclic monovalent hydrocarbon group which may contain a heteroatom, $X^a$ and $X^b$ are each independently hydrogen, fluorine or trifluoromethyl, with the proviso that at least one of $X^a$ and $X^b$ is fluorine or trifluoromethyl, m is an integer of 1 to 4, n is an integer of 0 to 4, and $M^+$ is an onium cation.

7. The polymer of claim 6 wherein $L^1$ is a sulfonyl bond.

8. The polymer of claim 6 wherein $L^2$ is a single bond and $A^1$ is hydrogen, fluorine or trifluoromethyl.

9. A resist composition comprising a base resin containing the polymer of claim 5 and an organic solvent.

10. The resist composition of claim 9 wherein the polymer further comprises recurring units of at least one type selected from recurring units having the formulae (6) and (7):

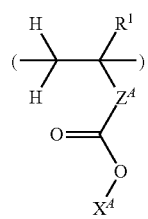
(6)

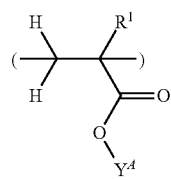
(7)

wherein $R^1$ is as defined above, $Z^A$ is a single bond, phenylene group, naphthylene group or (backbone)-C(=O)—O—Z'—, Z' is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

11. A resist composition comprising a base resin, an organic solvent, and a photoacid generator,
wherein the base resin contains a polymer comprising recurring units derived from a monomer having the formula (1):

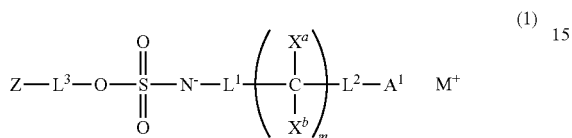
(1)

wherein Z is a polymerizable group, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond L; is a single bond or a $C_1$-$C_{40}$ straight, branched or cyclic divalent hydrocarbon group which may contain a heteroatom, $A^1$ is hydrogen, halogen or a $C_1$-$C_{20}$ straight, branched or cyclic monovalent hydrocarbon group which may contain a heteroatom, $X^a$ and $X^b$ are each independently hydrogen, fluorine or trifluoromethyl, with the proviso that at least one of $X^a$ and $X^b$ is a substituent group other than hydrogen, m is an integer of 1 to 4, and $M^+$ is an onium cation, and
the photoacid generator is a photoacid generator other than the compound having the formula (1):

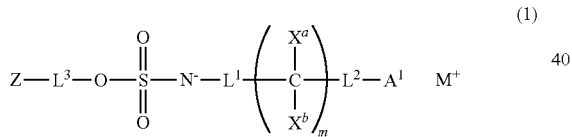
(1)

wherein $L^1$, $L^2$, $L^3$, $A^1$, $X^a$, $X^b$, m and $M^+$ are as defined above, and Z is a polymerizable group.

12. The resist composition of claim 11 wherein the photoacid generator has the formula (8) or (9):

(8)

wherein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, $X^-$ is an anion selected from the formulae (8A) to (8D):

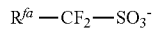
(8A)

(8B)

(8C)

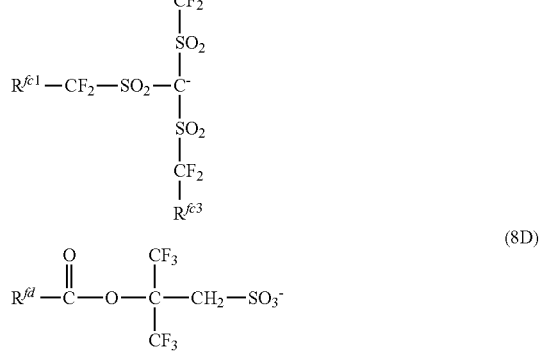
(8D)

wherein R, $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ straight, branched or cyclic monovalent hydrocarbon group which may contain a heteroatom,

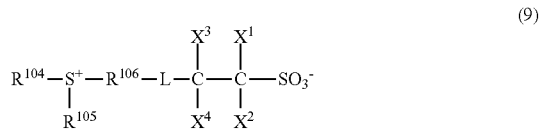
(9)

wherein $R^{104}$ and $R^{105}$ are each independently a $C_1$-$C_{30}$ straight, branched or cyclic monovalent hydrocarbon group which may contain a heteroatom, $R^{106}$ is a $C_1$-$C_{30}$ straight, branched or cyclic divalent hydrocarbon group which may contain a heteroatom, any two of $R^{104}$, $R^{105}$ and $R^{106}$ may bond together to form a ring with the sulfur atom to which they are attached, L is a single bond, ether bond or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl.

13. The resist composition of claim 9, further comprising an amine compound.

14. The resist composition of claim 9, further comprising a compound having the formula (10) or (11):

(10)

(11)

wherein $R^{151}$, $R^{152}$ and $R^{153}$ are each independently hydrogen, halogen exclusive of fluorine, or a $C_1$-$C_{40}$ straight, branched or cyclic monovalent hydrocarbon group which may contain a heteroatom, any two of $R^{151}$, $R^{152}$ and $R^{153}$ may bond together to form a ring with the carbon atom to which they are attached, $R^{154}$ is a $C_1$-$C_{40}$ straight, branched or cyclic monovalent hydrocarbon group which may contain a heteroatom, and $M^+$ is an onium cation.

15. The resist composition of claim 9, further comprising a surfactant which is insoluble or substantially insoluble in water and soluble in alkaline developer, and/or a surfactant which is insoluble or substantially insoluble in water and alkaline developer.

16. A pattern forming process comprising the steps of applying the resist composition of claim 9 onto a substrate, prebaking to form a resist film, exposing a selected region of the resist film to KrF excimer laser, ArF excimer laser, EB or EUV, baking, and developing the exposed resist film in a developer.

17. The pattern forming process of claim 16 wherein the developing step uses an alkaline aqueous solution as the developer, thereby forming a positive pattern in which an exposed region of the resist film is dissolved away and an unexposed region of the resist film is not dissolved.

18. The pattern forming process of claim 16 wherein the developing step uses an organic solvent as the developer, thereby forming a negative pattern in which an unexposed region of the resist film is dissolved away and an exposed region of the resist film is not dissolved.

19. The pattern forming process of claim 18 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

20. The process of claim 16 wherein the exposure step is carried out by immersion lithography while a liquid having a refractive index of at least 1.0 is held between the resist film and a projection lens.

21. The process of claim 20, further comprising the step of coating a protective film on the resist film prior to the exposure step, wherein immersion lithography is carried out while the liquid is held between the protective film and the projection lens.

* * * * *